United States Patent
Tanaka et al.

(12) 
(10) Patent No.: US 6,734,187 B1
(45) Date of Patent: May 11, 2004

(54) PURINE DERIVATIVES AND MEDICAMENTS COMPRISING THE SAME AS ACTIVE INGREDIENT

(75) Inventors: Toshihiko Tanaka, Yokohama (JP); Eiichirou Iwashita, Yokohama (JP); Akiko Tarao, Yokohama (JP); Akira Amenomori, Yokohama (JP); Yuya Ono, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/200,576

(22) Filed: Jul. 23, 2002

Related U.S. Application Data

(63) Continuation of application No. 09/554,077, filed as application No. PCT/JP98/05092 on Nov. 12, 1998.

(30) Foreign Application Priority Data

Nov. 12, 1997 (JP) .............................. 9-310365

(51) Int. Cl.[7] ................ C07D 473/32; C07D 473/28; C07D 473/18; A61K 31/52; A61K 31/522

(52) U.S. Cl. ............. 514/263.22; 514/234.2; 514/252.02; 514/263.2; 514/263.3; 514/263.33; 514/263.34; 514/263.35; 514/263.6; 514/263.37; 514/263.4; 544/118; 544/122; 544/264; 544/267; 544/269; 544/238; 544/270; 544/271; 544/276; 544/277; 544/319; 544/326; 544/329

(58) Field of Search ................. 544/118, 122, 544/264, 265, 267, 269, 238, 270, 271, 276, 277, 319, 326, 329; 514/234.2, 252.02, 263.2, 263.3, 263.33, 263.34, 263.35, 263.36, 263.22, 263.37, 263.4

(56) References Cited

U.S. PATENT DOCUMENTS

| | | |
|---|---|---|
| 3,862,189 A | 1/1975 | Schwender |
| 3,936,454 A | 2/1976 | Schwender |
| 4,012,495 A | 3/1977 | Schmiechen et al. |
| 4,193,926 A | 3/1980 | Schmiechen et al. |
| 5,124,455 A | 6/1992 | Lombardo |
| 5,770,611 A | 6/1998 | Brown |
| 5,861,404 A | 1/1999 | Niewöhner et al. |
| 5,948,913 A | 9/1999 | Yamamoto et al. |
| 2003/0045533 A1 * | 3/2003 | Liu et al. .................... 544/277 |

FOREIGN PATENT DOCUMENTS

| | | |
|---|---|---|
| CA | 2167353 | 7/1996 |
| JP | 08231545 | 9/1996 |
| WO | 92/12961 | 8/1992 |
| WO | 93/23401 | 11/1993 |
| WO | 94/11004 | 5/1994 |
| WO | 94/14742 | 7/1994 |
| WO | 94/12461 | 9/1994 |
| WO | 95/10525 | 4/1995 |
| WO | 95/00516 | 5/1995 |
| WO | 95/18815 | 7/1995 |
| WO | 96/26209 | 8/1996 |
| WO | 96/26942 | 9/1996 |
| WO | 96/36606 | 11/1996 |
| WO | 00/68231 | 11/2000 |

OTHER PUBLICATIONS

Makino, Ingternational Archives of Allergy and Immunology: Asthma Prevcention and Manegement Guidelines (KArger), p. 4,5,32,33,36–39 (1988).*

Angyal, A.M. et al., "Purines as Amplifiers of the Antibiotic Activity of Phleomycin Against *Escherichia coli* B", J. Gen. Microbiology, (1974), 85, 163–68.

Hidaka, H. and Shibuya, M., *A New Assay of Cyclic Nucleotide Phosphodiesterase; its Application to Human Serum*, Biochem. Med. 10, 301–311 (1974).

C.D. Nicholson, S.A. Jackman & R. Wilke, *The ability of denbufylline cyclic nucleotide phosphodiesterase and its affinity for adenosine receptors and the adenosine re–uptake site*, Br. J. Pharmacol, (1989), 97, 889–897.

(List continued on next page.)

Primary Examiner—Mark L. Berch
(74) Attorney, Agent, or Firm—Greenblum & Bernstein, P.L.C.

(57) ABSTRACT

Purine derivatives represented by the following formula and salts thereof:

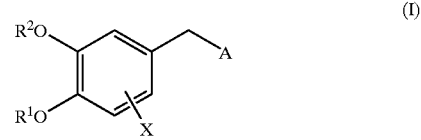

(I)

wherein $R^1$ represents a $C_1$–$C_4$ alkyl group or difluoromethyl group; $R^2$ represents tetrahydrofuranyl group, a $C_1$–$C_7$ alkyl group and the like; X represents hydrogen atom, a halogen atom or nitro group; and A represents a group represented by the following formula:

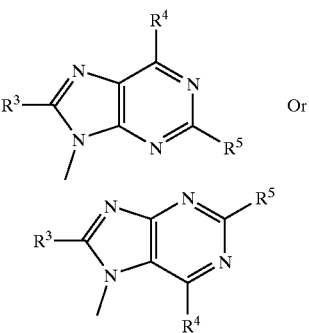

wherein $R^3$ represents hydrogen atom, a halogen atom and the like; $R^4$ and $R^5$ represent hydrogen atom, a halogen atom, a $C_1$–$C_4$ alkyl group, a $C_1$–$C_4$ alkoxyl group and the like, which are useful as active ingredients of medicaments such as antiasthmatic agents.

24 Claims, No Drawings

OTHER PUBLICATIONS

M.A. Giembycz, *Phosphodiesterase 4 Inhibitors and the Treatment of Asthma,* Drugs, 2000 Feb. 59 (2).
Abstract page of Japanese Patent No. 4–253945. 1992.
Abstract page of Japanese Patent No. 6–504782. 1994.
Abstract page of Japanese Patent No. 7–504442. 1995.
Abstract page of Japanese Patent No. 8–501318. 1996.
Abstract page of Japanese Patent No. 9–500376. 1997.
Abstract page of Japanese Patent No. 50–157360. 1975.
Beavo, J.A. Multiple Isozymes of Cyclic Nucleotide Phosphodiesterase, Adv. Second Messenger Phosphoprotein Res., 22, 1–38 (1988).
Beavo, J.A. and Reifsnyder, D.H., Primary Sequence of Cyclic Nucleotide Phosphodiesterase Isozymes and the design of Selective Inhibitors, Trends Pharm. Sci., 11, 150–155 (1990).
Torphy, T.J. and Undem, B.J., Phosphodiesterase Inhibitors: New Opportunities for the Treatment of Asthma, Thorax, 46, 512–523 (1991).

* cited by examiner

PURINE DERIVATIVES AND MEDICAMENTS COMPRISING THE SAME AS ACTIVE INGREDIENT

CROSS-REFERENCE TO RELATED APPLICATIONS

This application is a continuation of application Ser. No. 09/554,077, filed Nov. 12, 1998, which is a National Stage Application of International Application No. PCT/JP98/05092, filed Nov. 12, 1998, which was not published in English under PCT Article 21(2), entering the national stage on May 11, 2000, and which claims priority of Japanese Application No. 9/310365, filed Nov. 12, 1997. The entire disclosure of application Ser. No. 09/554,077 is considered as being part of the disclosure of this application, and the entire disclosure of application Ser. No. 09/554,077 is expressly incorporated by reference herein in its entirety.

TECHNICAL FIELD

The present invention relates to novel purine derivatives. More precisely, it relates to purine derivatives having inhibitory activity against phosphodiesterase IV. The present invention also relates to synthetic intermediates for the preparation of said novel purine derivatives.

BACKGROUND ART

Cyclic AMP (cAMP) is an important second messenger which is involved in relaxation of respiratory tract smooth muscles and control of inflammatory cells, and the messenger is decomposed by phosphodiesterase (hereinafter abbreviated as "PDE" in the specification) to be converted into inactive 5'-AMP. Therefore, it is believed that suppression of the decomposition of cAMP by PDE may increase the concentration of cAMP, thereby bronchodilatation and anti-inflammatory action can be achieved. For this reason, PDE inhibitors having inhibitory action against the decomposition of cAMP have been focused as medicaments for the treatment of asthma. In addition, five PDE isozymes (PDE I, II, III, IV and V) have recently been isolated, and their specific tissue distributions have been revealed (Adv. Second Messenger Phosphoprotein Res., 22, 1 (1988); Trends Pharm., Sci., 11, 150 (1990)).

Among inhibitors for these isozymes, in particular, inhibitors specific for PDE IV have been suggested to be possibly useful for the treatment of asthma (Thorax 46, 512 (1991)). As a compound having specific inhibitory activity against PDE IV, for example, the compound disclosed in Japanese Patent Unexamined Publication (Kokai) No. 50-157360/1975 (Rolipram) has been known.

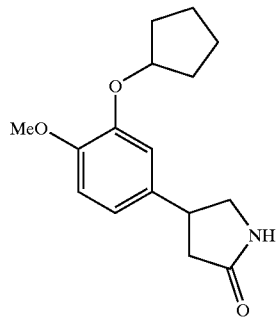

Although various compounds have been known as PDE IV inhibitors (for example, compounds disclosed in Japanese Patent Unexamined Publication (Kokai) No. 4-253945/1992, International Patent Publication in Japanese (Kohyo) Nos. 6-504782/1994, 7-504442/1995, 8-501318/1996 and 9-500376/1997 and so forth), they have not been used clinically so far, and development of novel compounds having PDE IV inhibitory activity has been desired.

DISCLOSURE OF THE INVENTION

An object of the present invention is to provide a novel compound having specific inhibitory activity against PDE IV, of which possible usefulness for treatment of asthma has been suggested. Another object of the present invention is to provide a medicament comprising a compound that has the aforementioned characteristic as an active ingredient. A further object of the present invention is to provide a synthetic intermediate useful for efficient preparation of the aforementioned compound.

The inventors of the present invention earnestly conducted researches to achieve the foregoing objects. As a result, they found that particular class of purine derivatives represented by the following formula had excellent inhibitory activity against PDE IV. They also found that these compounds were useful as active ingredients of medicaments, and they were extremely useful as, for example, as active ingredients of antiasthmatic agents. The present invention was achieved on the basis of these findings.

The present invention thus provides purine derivatives represented by the following formula (I), salts thereof, or N-oxides thereof, or hydrates thereof or solvates thereof:

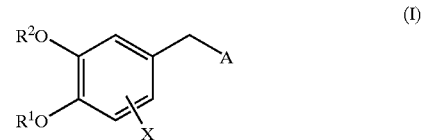

wherein $R^1$ represents a $C_1$–$C_4$ alkyl group or difluoromethyl group; $R^2$ represents tetrahydrofuranyl group, a $C_1$–$C_7$ alkyl group, a $C_1$–$C_1$ haloalkyl group, a $C_2$–$C_7$ alkenyl group, bicyclo[2,2,1]hept-2-yl group, or a $C_3$–$C_8$ cycloalkyl group; X represents hydrogen atom, a halogen atom, or nitro group; and A represents a group represented by the following formula:

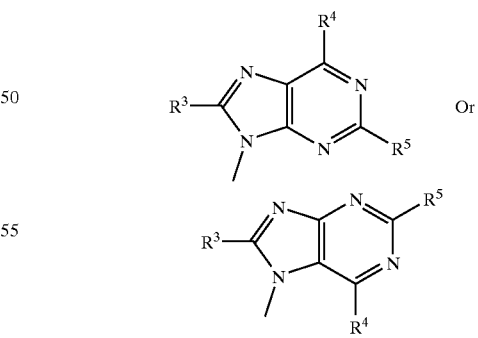

wherein $R^3$ represents hydrogen atom, a halogen atom, hydroxyl group, a $C_1$–$C_4$ alkyl group, a $C_1$–$C_4$ alkoxyl group, amino group, a $C_1$–$C_4$ alkylamino group, or a $C_2$–$C_8$ dialkylamino group; $R^4$ and $R^5$ each independently represent hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, a $C_2$–$C_8$ dialkylamino group, or a group represented by —Y—(CH$_2$)$_n$—B {Y represents —O—, —S—, —NHCO—, or —N(R$^6$)— (R$^6$ represents hydrogen atom or a C$_1$–C$_4$ alkyl group), n represents an integer of from 0 to 4, and B represents a phenyl group, a naphthyl group, or a heterocyclic residue, each of which may be substituted}, provided that either R$^4$ or R$^5$ represents —Y—(CH$_2$)$_n$—B {Y represents —O—, —S—, —NHCO—, or —N(R$^6$)— (R$^6$ represents hydrogen atom or a C$_1$–C$_4$ alkyl group)} when X represents hydrogen atom, and
(i) n represents an integer of from 0 to 4, and B represents a phenyl group, a naphthyl group, or a heterocyclic residue, each of which may be substituted when Y represents —O—, —S—, or —NHCO—, or
(ii) n represents an integer of from 1 to 4, and B represents a heterocyclic residue when Y represents —N(R$^6$)—.

According to preferred embodiments of the present invention, there are provided the aforementioned purine derivatives, salts thereof, or N-oxides thereof, or hydrates thereof or solvates thereof, wherein A is a group represented by the following formula:

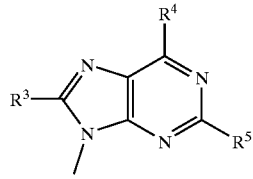

wherein R$^3$ is hydrogen atom, a halogen atom, hydroxyl group, a C$_1$–C$_4$ alkyl group, a C$_1$–C$_4$ alkoxyl group, amino group, a C$_1$–C$_4$ alkylamino group or a C$_2$–C$_8$ dialkylamino group; one of R$^4$ and R$^5$ is hydrogen atom, a halogen atom, a C$_1$–C$_4$ alkyl group, a C$_1$–C$_4$ alkoxyl group, amino group, a C$_1$–C$_4$ alkylamino group, pyrrolidinyl group, morpholino group, or a C$_2$–C$_8$ dialkylamino group, and the other is —Y—(CH$_2$)$_n$—B (Y is —O—, —S—, —NHCO—, or —N(R$^6$)— (R$^6$ represents hydrogen atom or a C$_1$–C$_4$ alkyl group), n is an integer of from 0 to 4, and B represents a phenyl group, a naphthyl group, or a heterocyclic residue, each of which may be substituted);

the aforementioned purine derivatives, salts thereof, or N-oxides thereof, or hydrates thereof or solvates thereof, wherein R$^1$ is a C$_1$–C$_4$ alkyl group; R$^2$ is tetrahydrofuranyl group, a C$_1$–C$_6$ alkyl group, a C$_1$–C$_3$ haloalkyl group or a C$_3$–C$_8$ cycloalkyl group, and A is a group represented by the following formula:

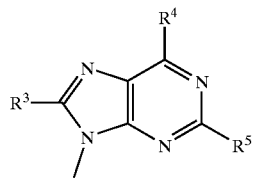

wherein R$^3$ is hydrogen atom, a halogen atom, hydroxyl group, a C$_1$–C$_4$ alkyl group, or a C$_1$–C$_4$ alkoxyl group; R$^4$ is hydrogen atom, a halogen atom, a C$_1$–C$_4$ alkyl group, a C$_1$–C$_4$ alkoxyl group, a C$_1$–C$_4$ alkylamino group, or a C$_2$–C$_8$ dialkylamino group, R$^5$ is —Y—(CH$_2$)$_n$—B (Y is —O—, —S—, or —NHCO—, n is an integer of from 1 to 4, and B represents a heterocyclic residue which may be substituted); and the aforementioned purine derivatives, salts thereof, or N-oxides thereof, or hydrates thereof or solvates thereof, wherein R$^1$ is a C$_1$–C$_3$ alkyl group; R$^2$ is a C$_3$–C$_8$ cycloalkyl group, and A is a group represented by the following formula:

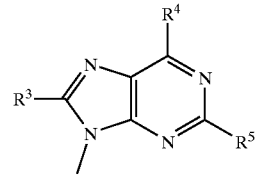

wherein R$^3$ is hydrogen atom, a C$_1$–C$_3$ alkyl group, or a C$_1$–C$_3$ alkoxyl group; R$^4$ is a C$_1$–C$_3$ alkyl group, a C$_1$–C$_3$ alkoxyl group or a C$_1$–C$_3$ alkylamino group; R$^5$ is —Y—(CH$_2$)$_n$—B (Y is —O—, n is an integer of from 1 to 4, and B is a heterocyclic residue which may be substituted).

According to another aspect of the present invention, medicaments are provided which contain a substance selected from the group consisting of the aforementioned purine derivatives, salts thereof, and N-oxide compounds thereof, and hydrates thereof and solvates thereof as an active ingredient. These medicaments are preferably provided as pharmaceutical compositions which contain the aforementioned active ingredient and an additive for pharmaceutical preparation, and they can be used as, for example, antiasthmatic agents for preventive and/or therapeutic treatment of asthma.

According to further aspects of the present invention, there are provided use of a substance selected from the group consisting of the aforementioned purine derivatives, salts thereof, and N-oxide compounds thereof, and hydrates thereof and solvates thereof for the manufacture of the aforementioned medicaments; methods for preventive and/or therapeutic treatment of asthma which comprise the step of administering an effective amount of a substance selected from the group consisting of the aforementioned purine derivatives, salts thereof, and N-oxide compounds thereof, and hydrates thereof and solvates thereof to a mammal including human; and phosphodiesterase IV inhibitors which comprise a substance selected from the group consisting of the aforementioned purine derivatives, salts thereof, and N-oxide compounds thereof, and hydrates thereof and solvates thereof.

According to further aspects of the present invention, there are provided compounds represented by the following formula (A):

(A)

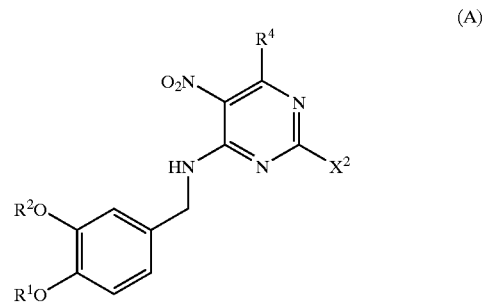

wherein R$^1$ represents a C$_1$–C$_4$ alkyl group or difluoromethyl group; R$^2$ represents tetrahydrofuranyl group, a C$_1$–C$_7$ alkyl group, a C$_1$–C$_7$ haloalkyl group, a C$_2$–C$_7$ alkenyl group, bicyclo[2,2,1]hept-2-yl group or a C$_3$–C$_8$ cycloalkyl group; $R^4$ represents hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, a $C_2$–$C_8$ dialkylamino group or —Y—$(CH_2)_n$—B {Y represents —O—, —S—, —NHCO—, or —N($R^6$)— ($R^6$ represents hydrogen atom or a $C_1$–$C_4$ alkyl group), n represents an integer of from 0 to 4, B represents a phenyl group, a naphthyl group, or a heterocyclic residue, each of which may be substituted, and $X^2$ represents a halogen atom, and compounds represented by the following formula (B):

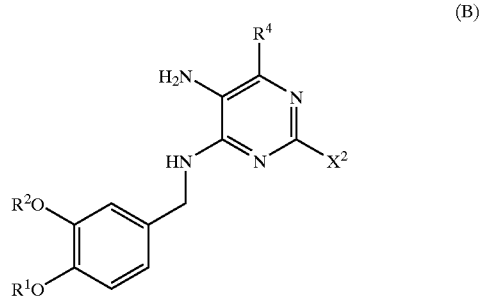

wherein $R^1$ represents a $C_1$–$C_4$ alkyl group or difluoromethyl group; $R^2$ represents tetrahydrofuranyl group, a $C_1$–$C_7$ alkyl group, a $C_1$–$C_7$ haloalkyl group, a $C_2$–$C_7$ alkenyl group, bicyclo[2,2,1]hept-2-yl group, or a $C_3$–$C_8$ cycloalkyl group; $R^4$ represents hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, a $C_2$–$C_8$ dialkylamino group, or —Y—$(CH_2)_n$—B {Y represents —O—, —S—, —NHCO—, or —N($R^6$)— ($R^6$ represents hydrogen atom or a $C_1$–$C_4$ alkyl group), n represents an integer of from 0 to 4, B represents a phenyl group, a naphthyl group, or a heterocyclic residue, each of which may be substituted, and $X^2$ represents a halogen atom. These compounds are useful as synthetic intermediates for preparation of the compounds represented by the aforementioned formula (I).

According to preferred embodiments of the synthetic intermediates represented by the formula (A) or (B), there are provided those wherein $R^1$ is a $C_1$–$C_4$ alkyl group, $R^2$ is tetrahydrofuranyl group, a $C_1$–$C_6$ alkyl group, a $C_1$–$C_3$ haloalkyl group, or a $C_3$–$C_8$ cycloalkyl group, $R^4$ is hydrogen atom, a halogen atom, a $C_1$–$C_4$ alkyl group, a $C_1$–$C_4$ alkoxyl group, a $C_1$–$C_4$ alkylamino group or a $C_2$–$C_8$ dialkylamino group.

BEST MODE FOR CARRYING OUT THE INVENTION $R^1$ represents a linear or branched $C_1$–$C_4$ alkyl group (methyl group, ethyl group, n-propyl group, isopropyl group, n-butyl group, isobutyl group, sec-butyl group, t-butyl group and the like), or difluoromethyl group. $R^1$ preferably represents a $C_1$–$C_4$ alkyl group, more preferably a $C_1$–$C_3$ alkyl group, further preferably methyl group or ethyl group, and most preferably methyl group.

$R^2$ represents tetrahydrofuranyl group, a $C_1$–$C_7$ linear or branched alkyl group (methyl group $R^2$ represents, ethyl group, n-propyl group, isopropyl group, n-butyl group, isobutyl group, sec-butyl group, t-butyl group, n-pentyl group, 1,2-dimethylpropyl group, 1,1-dimethylpropyl group, n-hexyl group, 1-methylpentyl group, 2-methylpentyl group, 3-methylpentyl group, 4-methylpentyl group, 1,1-dimethylbutyl group, 2,2-dimethylbutyl group, 3,3-dimethylbutyl group, 1,2-dimethylbutyl group, 1,3-dimethylbutyl group, 1,2,2-trimethylpropyl group, heptyl group, 5-methylhexyl group, 2,2-dimethylpentyl group, 3,3-dimethylpentyl group, 4,4-dimethylpentyl group, 1,2-dimethylpentyl group, 1,3-dimethylpentyl group, 1,4-dimethylpentyl group, 1,2,3-trimethylbutyl group, 1,1,2-trimethylbutyl group, 1,1,3-trimethylbutyl group and the like), a $C_1$–$C_7$ haloalkyl group (chloromethyl group, bromomethyl group, dichloromethyl group, 1-chloroethyl group, 2-chloroethyl group, 3-chloropropyl group, 3-chlorobutyl group, 5-chloropentyl group, 6-chlorohexyl group, difluoromethyl group, trifluoromethyl group and the like), a $C_2$–$C_7$ alkenyl group (vinyl group, allyl group, 2-propenyl group, isopropenyl group, 3-butenyl group, 4-pentenyl group, 5-hexenyl group and the like), bicyclo[2,2,1]hept-2-yl group, or a $C_3$–$C_8$ cycloalkyl group (cyclopropyl group, cyclobutyl group, cyclopentyl group, cyclohexyl group, cycloheptyl group and the like). $R^2$ preferably represents tetrahydrofuranyl group, a $C_1$–$C_6$ alkyl group, a $C_1$–$C_3$ haloalkyl group, or a $C_3$–$C_8$ cycloalkyl group, more preferably a $C_3$–$C_8$ cycloalkyl group, further preferably a $C_4$–$C_6$ cycloalkyl group, and most preferably cyclopentyl group.

X represents hydrogen atom, a halogen atom (when a halogen is referred to in the specification, the halogen may be any of fluorine, chlorine, bromine, and iodine), or nitro group, preferably hydrogen atom. As symbol "A", a group represented by the following formula is preferred.

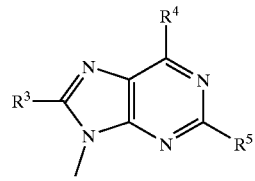

In the above formula, $R^3$ represents hydrogen atom, a halogen atom, hydroxyl group, a linear or branched $C_1$–$C_4$ alkyl group (methyl group, ethyl group, n-propyl group, isopropyl group, n-butyl group, isobutyl group, sec-butyl group, t-butyl group and the like), a linear or branched $C_1$–$C_4$ alkoxyl group (methoxy group, isopropoxy group, butoxy group and the like), amino group, a linear or branched $C_1$–$C_4$ alkylamino group (methylamino group, n-propylamino group, isopropylamino group, butylamino group and the like) or a linear or branched $C_2$–$C_8$ dialkylamino group (dimethyl amino group, diethylamino group, dipropylamino group, dibutylamino group and the like). $R^3$ preferably represents hydrogen atom, a halogen atom, hydroxyl group, a linear or branched $C_1$–$C_4$ alkyl group, a $C_1$–$C_4$ linear or branched alkoxyl group, more preferably hydrogen atom, a $C_1$–$C_3$ alkyl group or a $C_1$–$C_3$ alkoxyl group.

In the aforementioned formula, $R^4$ and $R^5$ each independently represent hydrogen atom, halogen atom, a linear or branched $C_1$–$C_4$ alkyl group (methyl group, ethyl group, n-propyl group, isopropyl group, n-butyl group, isobutyl group, sec-butyl group, t-butyl group and the like), a linear or branched $C_1$–$C_4$ alkoxyl group (methoxy group, isopropoxy group, butoxy group and the like), amino group, a linear or branched $C_1$–$C_4$ alkylamino group (methylamino group, n-propylamino group, isopropylamino group, butylamino group and the like), pyrrolidinyl group, morpholino group, a linear or branched $C_2$–$C_8$ dialkylamino groups (dimethylamino group, diethylamino group, dipropylamino group, dibutylamino group and the like) or —Y—$(CH_2)_n$—B {Y is —O—, —S—, —NHCO—, or —N($R^6$)— ($R^6$ is hydrogen atom or a linear or branched $C_1$–$C_4$ alkyl group (methyl group, ethyl group, n-propyl group, isopropyl group, n-butyl group, isobutyl group, sec-butyl group, t-butyl group and the like), and Y is preferably —O—)}. Symbol "n" represents an integer of from 0 to 4, preferably an integer of from 1 to 3.

B represents a phenyl group, a naphthyl group, or a heterocyclic residue. Each of these groups may have, on their rings, one or more substituents selected from the group consisting of a halogen atom, a linear or branched $C_1$–$C_4$ alkyl groups (methyl group, ethyl group, n-propyl group, isopropyl group, n-butyl group, isobutyl group, sec-butyl group, t-butyl group and the like), a $C_1$–$C_4$ haloalkyl group (chloromethyl group, bromomethyl group, dichloromethyl group, 1-chloroethyl group, 2-chloroethyl group, 3-chloropropyl group, 4-chlorobutyl group, difluoromethyl group, trifluoromethyl group and the like), a linear or branched $C_1$–$C_4$ alkoxyl group (methoxy group, isopropoxy group, butoxy group and the like), a linear or branched $C_1$–$C_4$ haloalkoxyl group (trifluoromethoxy group, difluoromethoxy group, 2,2,2-trifluoromethoxy group, 3-chloropropoxy group and the like), cyano group, nitro group, amino group, hydroxy group, carboxy group, a $C_1$–$C_4$ acyl groups (formyl group, acetyl group, propionyl group and the like), a $C_2$–$C_4$ alkoxycarbonyl group (methoxycarbonyl group, ethoxycarbonyl group and the like), a linear or branched $C_1$–$C_4$ alkylamino group (methylamino group, isopropylamino group, butylamino group etc.), and a linear or branched $C_2$–$C_6$ dialkylamino group (dimethylamino group, diethylamino group and the like), preferably one or more substituents selected from the group consisting of a halogen atom, a $C_1$–$C_4$ alkyl group, a $C_1$–$C_4$ alkoxyl group, a $C_1$–$C_4$ haloalkoxyl group, carboxy group, and a $C_2$–$C_4$ alkoxycarbonyl group.

As the heterocyclic residue, a heterocyclic residue having 1 to 5 hetero atoms selected from oxygen atom, sulfur atom and nitrogen atom and having 5 to 10 ring-constituting atoms may be used, such as thienyl group, furyl group, pyrrolyl group, imidazolyl group, pyrazolyl group, triazolyl group tetrazolyl group, oxazolyl group, isooxazolyl group, thiazolyl group, isothiazolyl group, pyrrolidinyl group pyridyl group, pyridazinyl group, pyrazinyl group, pyrimidinyl group, triazinyl group, piperidyl group, piperidino group, morpholinyl group, morpholino group, piperazinyl group, benzimidazolyl group, indolyl group, quinolyl group, naphthylidinyl group, quinazolinyl group and the like, preferably thienyl group, furyl group, pyrrolyl group, imidazolyl group, pyrazolyl group, pyridyl group, pyridazinyl group, pyrazinyl group, pyrimidinyl group, triazinyl group, piperidyl group, piperidino group, morpholinyl group, morpholino group, piperazinyl group, benzimidazolyl group and the like, more preferably a 6-membered heterocyclic residue having one or two nitrogen atoms as the hetero atom(s), for example, pyridyl group, pyridazinyl group, pyrazinyl group, pyrimidinyl group, triazinyl group, piperidyl group, piperidino group, morpholinyl group, morpholino group, piperazinyl group and the like. B represents a heterocyclic residue which may be substituted, and most preferably an unsubstituted heterocyclic residue.

As for $R^4$ and $R^5$, $R^4$ preferably represents hydrogen atom, a halogen atom, a $C_1$–$C_4$ alkyl group, a $C_1$–$C_4$ alkoxyl group, a $C_1$–$C_4$ alkylamino group, or a $C_2$–$C_8$ dialkylamino group, more preferably a $C_1$–$C_3$ alkyl group, a $C_1$–$C_3$ alkoxyl group, or a $C_1$–$C_3$ alkylamino group, and $R^5$ represents —Y—$(CH_2)_n$—B (Y, n, and B have the same meanings as already defined above).

When X represents hydrogen atom, either of $R^4$ or $R^5$ represents —Y—$(CH_2)_n$—B. In this case, Y represents —O—, —S—, —NHCO—, or —N($R^6$)— ($R^6$ represents hydrogen atom or a $C_1$–$C_4$ alkyl group), and (i) when Y represents —O—, —S—, or —NHCO—, n represents an integer of from 0 to 4, and B represents a phenyl group, a naphthyl group, or a heterocyclic residue, each of which may be substituted, or (ii) when Y represents —N($R^6$)—, n represents an integer of from 1 to 4, and B represents a heterocyclic residue.

When $R^4$ or $R^5$ in the compounds represented by the aforementioned formula (I) represents —Y$(CH_2)_n$—B wherein B is a heterocyclic residue which has at least one nitrogen atom as the hetero atom, the compounds may exist as N-oxide compounds. The N-oxide compounds also fall within the scope of the present invention.

Specific examples of the compounds of the present invention are shown in Table 1 below. In the table, Me represents methyl group, Et represents ethyl group, and n-Pr represents normal propyl group.

TABLE 1

| Compound No | X | R1 | R2 | R3 | R4 | R5 |
|---|---|---|---|---|---|---|
| 1 | H | Me | | cyclopentyl | H | H | H |
| 2 | H | Me | | cyclopentyl | H | H | OMe |
| 3 | H | Me | | cyclopentyl | H | H | F |
| 4 | H | Me | | cyclopentyl | H | H | Cl |

TABLE 1-continued

| Compound No | X | R1 | R2 | R3 | R4 | R5 |
|---|---|---|---|---|---|---|
| 5 | H | Me | cyclopentyl | H | H | Br |
| 6 | H | Me | cyclopentyl | H | H | I |
| 7 | H | Me | cyclopentyl | H | H | 2-methoxypyridin-yl |
| 8 | H | Me | cyclopentyl | H | H | 2-methoxypyridin-yl N-oxide |
| 9 | H | Me | cyclopentyl | H | H | 3-methoxypyridin-yl |
| 10 | H | Me | cyclopentyl | H | H | 3-methoxypyridin-yl N-oxide |
| 11 | H | Me | cyclopentyl | H | H | 4-methoxypyridin-yl |
| 12 | H | Me | cyclopentyl | H | H | 4-methoxypyridin-yl N-oxide |
| 13 | H | Me | cyclopentyl | H | H | 2-(methoxymethyl)pyridin-yl |
| 14 | H | Me | cyclopentyl | H | H | 2-(methoxymethyl)pyridin-yl N-oxide |
| 15 | H | Me | cyclopentyl | H | H | 3-(methoxymethyl)pyridin-yl |
| 16 | H | Me | cyclopentyl | H | H | 3-(methoxymethyl)pyridin-yl N-oxide |

TABLE 1-continued

| Compound No | X | R1 | R2 | R3 | R4 | R5 |
|---|---|---|---|---|---|---|
| 17 | H | Me | cyclopentyl | H | H | -OCH2-(pyridin-4-yl) (methoxymethyl-4-pyridine) |
| 18 | H | Me | cyclopentyl | H | H | -OCH2-(pyridin-4-yl N-oxide) |
| 19 | H | Me | cyclopentyl | H | H | -OCH2CH2-(pyridin-2-yl) |
| 20 | H | Me | cyclopentyl | H | H | -OCH2CH2-(pyridin-2-yl N-oxide) |
| 21 | H | Me | cyclopentyl | H | H | -OCH2CH2-(pyridin-3-yl) |
| 22 | H | Me | cyclopentyl | H | H | -OCH2CH2-(pyridin-3-yl N-oxide) |
| 23 | H | Me | cyclopentyl | H | H | -OCH2CH2-(pyridin-4-yl) |
| 24 | H | Me | cyclopentyl | H | H | -OCH2CH2-(pyridin-4-yl N-oxide) |
| 25 | H | Me | cyclopentyl | H | H | -OCH2CH2CH2-(pyridin-2-yl) |
| 26 | H | Me | cyclopentyl | H | H | -OCH2CH2CH2-(pyridin-2-yl N-oxide) |
| 27 | H | Me | cyclopentyl | H | H | -OCH2CH2CH2-(pyridin-3-yl) |
| 28 | H | Me | cyclopentyl | H | H | -OCH2CH2CH2-(pyridin-3-yl N-oxide) |

TABLE 1-continued

| Compound No | X | R1 | R2 | R3 | R4 | R5 |
|---|---|---|---|---|---|---|
| 29 | H | Me | cyclopentyl | H | H | methoxypropyl-(pyridin-4-yl) |
| 30 | H | Me | cyclopentyl | H | H | methoxypropyl-(pyridin-4-yl N-oxide) |
| 31 | H | Me | cyclopentyl | H | H | NH-CH2-CH2-phenyl |
| 32 | H | Me | cyclopentyl | H | H | N(Me)-CH2-CH2-phenyl |
| 33 | H | Me | cyclopentyl | H | H | NH-CH2-CH2-(pyridin-2-yl) |
| 34 | H | Me | cyclopentyl | H | H | N(Me)-CH2-CH2-(pyridin-2-yl) |
| 35 | H | Me | cyclopentyl | H | H | NH-CH2-CH2-(pyridin-3-yl) |
| 36 | H | Me | cyclopentyl | H | H | N(Me)-CH2-CH2-(pyridin-3-yl) |
| 37 | H | Me | cyclopentyl | H | H | NH-CH2-CH2-(pyridin-4-yl) |
| 38 | H | Me | cyclopentyl | H | H | N(Me)-CH2-CH2-(pyridin-4-yl) |
| 39 | H | Me | cyclopentyl | H | H | methoxymethyl-(pyridazin-3-yl) |

TABLE 1-continued
| Compound No | X | R1 | R2 | R3 | R4 | R5 |
|---|---|---|---|---|---|---|
| 40 | H | Me |  | H | H | 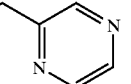 |
| 41 | H | Me |  | H | H | 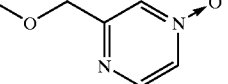 |
| 42 | H | Me |  | H | H | 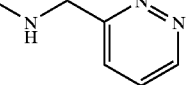 |
| 43 | H | Me |  | H | H | 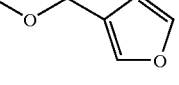 |
| 44 | H | Me |  | H | H | 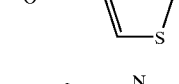 |
| 45 | H | Me |  | H | H | 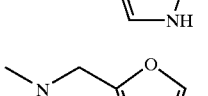 |
| 46 | H | Me |  | H | H | 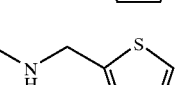 |
| 47 | H | Me |  | H | H | 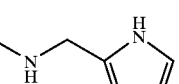 |
| 48 | H | Me |  | H | H | 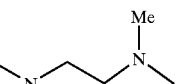 |
| 49 | H | Me |  | H | H | 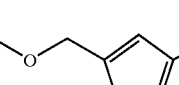 |
| 50 | H | Me |  | H | H | 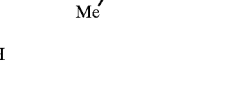 |
| 51 | H | Me |  | H | Me | H |
| 52 | H | Me |  | H | Me | OMe |
| 53 | H | Me |  | H | Me | F |

TABLE 1-continued

| Compound No | X | R1 | R2 | R3 | R4 | R5 |
|---|---|---|---|---|---|---|
| 54 | H | Me | cyclopentyl | H | Me | Cl |
| 55 | H | Me | cyclopentyl | H | Me | Br |
| 56 | H | Me | cyclopentyl | H | Me | I |
| 57 | H | Me | cyclopentyl | H | Me | 2-methoxypyridin-yl |
| 58 | H | Me | cyclopentyl | H | Me | 2-methoxypyridine N-oxide |
| 59 | H | Me | cyclopentyl | H | Me | 3-methoxypyridin-yl |
| 60 | H | Me | cyclopentyl | H | Me | 3-methoxypyridine N-oxide |
| 61 | H | Me | cyclopentyl | H | Me | 4-methoxypyridin-yl |
| 62 | H | Me | cyclopentyl | H | Me | 4-methoxypyridine N-oxide |
| 63 | H | Me | cyclopentyl | H | Me | 2-(methoxymethyl)pyridin-yl |
| 64 | H | Me | cyclopentyl | H | Me | 2-(methoxymethyl)pyridine N-oxide |
| 65 | H | Me | cyclopentyl | H | Me | 3-(methoxymethyl)pyridin-yl |
| 66 | H | Me | cyclopentyl | H | Me | 3-(methoxymethyl)pyridine N-oxide |

TABLE 1-continued

| Compound No | X | R1 | R2 | R3 | R4 | R5 |
|---|---|---|---|---|---|---|
| 67 | H | Me | cyclopentyl | H | Me | methoxymethyl-4-pyridyl |
| 68 | H | Me | cyclopentyl | H | Me | methoxymethyl-4-pyridyl N-oxide |
| 69 | H | Me | cyclopentyl | H | Me | 2-(2-methoxyethyl)pyridine |
| 70 | H | Me | cyclopentyl | H | Me | 2-(2-methoxyethyl)pyridine N-oxide |
| 71 | H | Me | cyclopentyl | H | Me | 3-(2-methoxyethyl)pyridine |
| 72 | H | Me | cyclopentyl | H | Me | 3-(2-methoxyethyl)pyridine N-oxide |
| 73 | H | Me | cyclopentyl | H | Me | 4-(2-methoxyethyl)pyridine |
| 74 | H | Me | cyclopentyl | H | Me | 4-(2-methoxyethyl)pyridine N-oxide |
| 75 | H | Me | cyclopentyl | H | Me | 2-(3-methoxypropyl)pyridine |
| 76 | H | Me | cyclopentyl | H | Me | 2-(3-methoxypropyl)pyridine N-oxide |
| 77 | H | Me | cyclopentyl | H | Me | 3-(3-methoxypropyl)pyridine |
| 78 | H | Me | cyclopentyl | H | Me | 3-(3-methoxypropyl)pyridine N-oxide |

TABLE 1-continued

| Compound No | X | R1 | R2 | R3 | R4 | R5 |
|---|---|---|---|---|---|---|
| 79 | H | Me | cyclopentyl | H | Me | 3-(4-pyridyl)propyl methyl ether |
| 80 | H | Me | cyclopentyl | H | Me | 3-(4-pyridyl N-oxide)propyl methyl ether |
| 81 | H | Me | cyclopentyl | H | Me | N-(2-phenylethyl)amino |
| 82 | H | Me | cyclopentyl | H | Me | N-methyl-N-(2-phenylethyl)amino |
| 83 | H | Me | cyclopentyl | H | Me | N-[2-(2-pyridyl)ethyl]amino |
| 84 | H | Me | cyclopentyl | H | Me | N-methyl-N-[2-(2-pyridyl)ethyl]amino |
| 85 | H | Me | cyclopentyl | H | Me | N-[2-(3-pyridyl)ethyl]amino |
| 86 | H | Me | cyclopentyl | H | Me | N-methyl-N-[2-(3-pyridyl)ethyl]amino |
| 87 | H | Me | cyclopentyl | H | Me | N-[2-(4-pyridyl)ethyl]amino |
| 88 | H | Me | cyclopentyl | H | Me | N-methyl-N-[2-(4-pyridyl)ethyl]amino |
| 89 | H | Me | cyclopentyl | H | Me | (3-pyridazinyl)methyl methyl ether |

TABLE 1-continued
| Compound No | X | R1 | R2 | R3 | R4 | R5 |
|---|---|---|---|---|---|---|
| 90 | H | Me |  | H | Me | 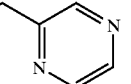 |
| 91 | H | Me |  | H | Me | 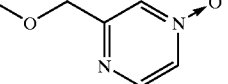 |
| 92 | H | Me |  | H | Me | 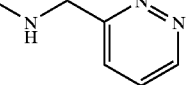 |
| 93 | H | Me |  | H | Me | 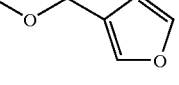 |
| 94 | H | Me |  | H | Me | 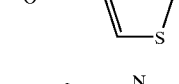 |
| 95 | H | Me |  | H | Me | 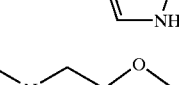 |
| 96 | H | Me |  | H | Me | 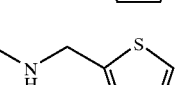 |
| 97 | H | Me |  | H | Me | 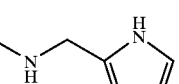 |
| 98 | H | Me |  | H | Me | 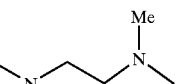 |
| 99 | H | Me |  | H | Me | 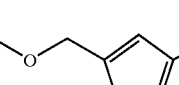 |
| 100 | H | Me |  | H | Me | 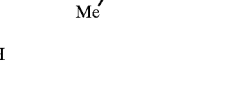 |
| 101 | H | Me |  | H | Et | H |
| 102 | H | Me |  | H | Et | OMe |
| 103 | H | Me |  | H | Et | F |

TABLE 1-continued

| Compound No | X | R1 | R2 | R3 | R4 | R5 |
|---|---|---|---|---|---|---|
| 104 | H | Me | cyclopentyl | H | Et | Cl |
| 105 | H | Me | cyclopentyl | H | Et | Br |
| 106 | H | Me | cyclopentyl | H | Et | I |
| 107 | H | Me | cyclopentyl | H | Et | 2-methoxypyridine |
| 108 | H | Me | cyclopentyl | H | Et | 2-methoxypyridine N-oxide |
| 109 | H | Me | cyclopentyl | H | Et | 3-methoxypyridine |
| 110 | H | Me | cyclopentyl | H | Et | 3-methoxypyridine N-oxide |
| 111 | H | Me | cyclopentyl | H | Et | 4-methoxypyridine |
| 112 | H | Me | cyclopentyl | H | Et | 4-methoxypyridine N-oxide |
| 113 | H | Me | cyclopentyl | H | Et | 2-(methoxymethyl)pyridine |
| 114 | H | Me | cyclopentyl | H | Et | 2-(methoxymethyl)pyridine N-oxide |
| 115 | H | Me | cyclopentyl | H | Et | 3-(methoxymethyl)pyridine |
| 116 | H | Me | cyclopentyl | H | Et | 3-(methoxymethyl)pyridine N-oxide |

TABLE 1-continued

| Compound No | X | R1 | R2 | R3 | R4 | R5 |
|---|---|---|---|---|---|---|
| 117 | H | Me | cyclopentyl | H | Et | methoxymethyl-4-pyridine |
| 118 | H | Me | cyclopentyl | H | Et | methoxymethyl-4-pyridine N-oxide |
| 119 | H | Me | cyclopentyl | H | Et | 2-(2-methoxyethyl)pyridine |
| 120 | H | Me | cyclopentyl | H | Et | 2-(2-methoxyethyl)pyridine N-oxide |
| 121 | H | Me | cyclopentyl | H | Et | 3-(2-methoxyethyl)pyridine |
| 122 | H | Me | cyclopentyl | H | Et | 3-(2-methoxyethyl)pyridine N-oxide |
| 123 | H | Me | cyclopentyl | H | Et | 4-(2-methoxyethyl)pyridine |
| 124 | H | Me | cyclopentyl | H | Et | 4-(2-methoxyethyl)pyridine N-oxide |
| 125 | H | Me | cyclopentyl | H | Et | 2-(3-methoxypropyl)pyridine |
| 126 | H | Me | cyclopentyl | H | Et | 2-(3-methoxypropyl)pyridine N-oxide |
| 127 | H | Me | cyclopentyl | H | Et | 3-(3-methoxypropyl)pyridine |
| 128 | H | Me | cyclopentyl | H | Et | 3-(3-methoxypropyl)pyridine N-oxide |

TABLE 1-continued

| Compound No | X | R1 | R2 | R3 | R4 | R5 |
|---|---|---|---|---|---|---|
| 129 | H | Me | cyclopentyl | H | Et | 3-(4-pyridyl)propyl methyl ether |
| 130 | H | Me | cyclopentyl | H | Et | 3-(4-pyridyl N-oxide)propyl methyl ether |
| 131 | H | Me | cyclopentyl | H | Et | N-H, phenethylamine |
| 132 | H | Me | cyclopentyl | H | Et | N-Me, phenethylamine |
| 133 | H | Me | cyclopentyl | H | Et | N-H, 2-(2-pyridyl)ethylamine |
| 134 | H | Me | cyclopentyl | H | Et | N-Me, 2-(2-pyridyl)ethylamine |
| 135 | H | Me | cyclopentyl | H | Et | N-H, 2-(3-pyridyl)ethylamine |
| 136 | H | Me | cyclopentyl | H | Et | N-Me, 2-(3-pyridyl)ethylamine |
| 137 | H | Me | cyclopentyl | H | Et | N-H, 2-(4-pyridyl)ethylamine |
| 138 | H | Me | cyclopentyl | H | Et | N-Me, 2-(4-pyridyl)ethylamine |
| 139 | H | Me | cyclopentyl | H | Et | (3-pyridazinyl)methyl methyl ether |

TABLE 1-continued
| Compound No | X | R1 | R2 | R3 | R4 | R5 |
|---|---|---|---|---|---|---|
| 140 | H | Me |  | H | Et | 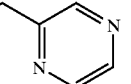 |
| 141 | H | Me |  | H | Et | 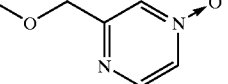 |
| 142 | H | Me |  | H | Et | 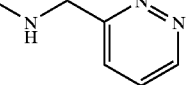 |
| 143 | H | Me |  | H | Et | 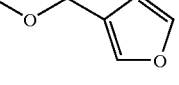 |
| 144 | H | Me |  | H | Et | 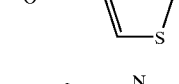 |
| 145 | H | Me |  | H | Et | 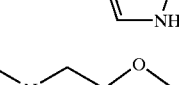 |
| 146 | H | Me |  | H | Et | 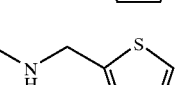 |
| 147 | H | Me |  | H | Et | 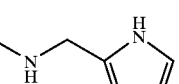 |
| 148 | H | Me |  | H | Et | 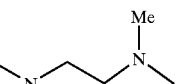 |
| 149 | H | Me |  | H | Et | 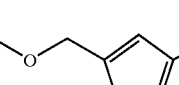 |
| 150 | H | Me |  | H | Et | 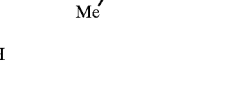 |
| 151 | H | Me |  | H | OMe | H |
| 152 | H | Me |  | H | OMe | OMe |
| 153 | H | Me |  | H | OMe | F |

TABLE 1-continued
| Compound No | X | R1 | R2 | R3 | R4 | R5 |
|---|---|---|---|---|---|---|
| 154 | H | Me |  | H | OMe | Cl |
| 155 | H | Me |  | H | OMe | Br |
| 156 | H | Me |  | H | OMe | I |
| 157 | H | Me |  | H | OMe | 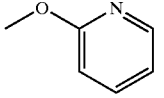 |
| 158 | H | Me |  | H | OMe | 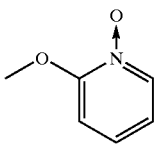 |
| 159 | H | Me |  | H | OMe | 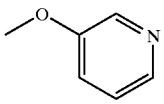 |
| 160 | H | Me |  | H | OMe | 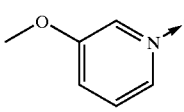 |
| 161 | H | Me |  | H | OMe | 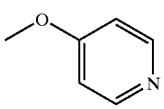 |
| 162 | H | Me |  | H | OMe | 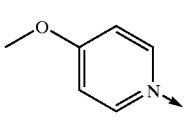 |
| 163 | H | Me |  | H | OMe | 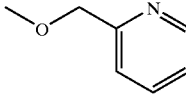 |
| 164 | H | Me |  | H | OMe | 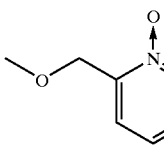 |
| 165 | H | Me |  | H | OMe | 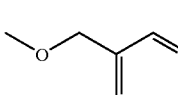 |
| 166 | H | Me |  | H | OMe | 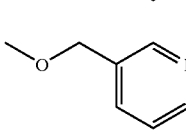 |

TABLE 1-continued

| Compound No | X | R1 | R2 | R3 | R4 | R5 |
|---|---|---|---|---|---|---|
| 167 | H | Me | cyclopentyl | H | OMe | 4-(methoxymethyl)pyridine |
| 168 | H | Me | cyclopentyl | H | OMe | 4-(methoxymethyl)pyridine N-oxide |
| 169 | H | Me | cyclopentyl | H | OMe | 2-(2-methoxyethyl)pyridine |
| 170 | H | Me | cyclopentyl | H | OMe | 2-(2-methoxyethyl)pyridine N-oxide |
| 171 | H | Me | cyclopentyl | H | OMe | 3-(2-methoxyethyl)pyridine |
| 172 | H | Me | cyclopentyl | H | OMe | 3-(2-methoxyethyl)pyridine N-oxide |
| 173 | H | Me | cyclopentyl | H | OMe | 4-(2-methoxyethyl)pyridine |
| 174 | H | Me | cyclopentyl | H | OMe | 4-(2-methoxyethyl)pyridine N-oxide |
| 175 | H | Me | cyclopentyl | H | OMe | 2-(3-methoxypropyl)pyridine |
| 176 | H | Me | cyclopentyl | H | OMe | 2-(3-methoxypropyl)pyridine N-oxide |
| 177 | H | Me | cyclopentyl | H | OMe | 3-(3-methoxypropyl)pyridine |
| 178 | H | Me | cyclopentyl | H | OMe | 3-(3-methoxypropyl)pyridine N-oxide |

TABLE 1-continued
| Compound No | X | R1 | R2 | R3 | R4 | R5 |
|---|---|---|---|---|---|---|
| 179 | H | Me |  | H | OMe | 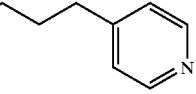 |
| 180 | H | Me |  | H | OMe | 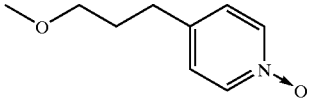 |
| 181 | H | Me |  | H | OMe | 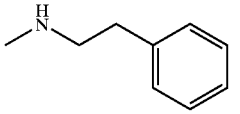 |
| 182 | H | Me |  | H | OMe | 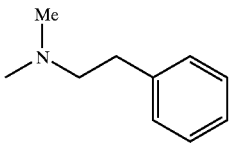 |
| 183 | H | Me |  | H | OMe | 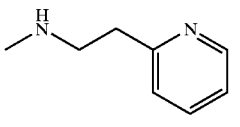 |
| 184 | H | Me |  | H | OMe | 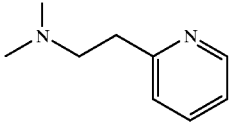 |
| 185 | H | Me |  | H | OMe | 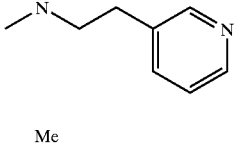 |
| 186 | H | Me |  | H | OMe | 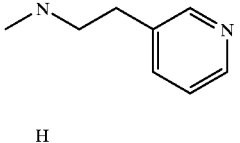 |
| 187 | H | Me |  | H | OMe | 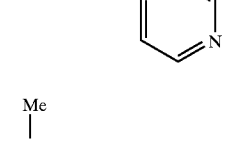 |
| 188 | H | Me |  | H | OMe | 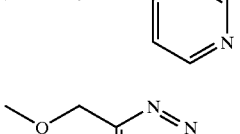 |
| 189 | H | Me |  | H | OMe | 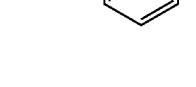 |

TABLE 1-continued

| Compound No | X | R1 | R2 | R3 | R4 | R5 |
|---|---|---|---|---|---|---|
| 190 | H | Me | cyclopentyl | H | OMe | CH2OCH2-pyrazine |
| 191 | H | Me | cyclopentyl | H | OMe | CH2OCH2-pyrazine N-oxide |
| 192 | H | Me | cyclopentyl | H | OMe | CH2NH-pyridazin-3-yl |
| 193 | H | Me | cyclopentyl | H | OMe | CH2OCH2-furan-3-yl |
| 194 | H | Me | cyclopentyl | H | OMe | CH2OCH2-thiophen-3-yl |
| 195 | H | Me | cyclopentyl | H | OMe | CH2OCH2-imidazol-4-yl |
| 196 | H | Me | cyclopentyl | H | OMe | CH2NH-furan-2-yl |
| 197 | H | Me | cyclopentyl | H | OMe | CH2NH-thiophen-2-yl |
| 198 | H | Me | cyclopentyl | H | OMe | CH2NH-pyrrol-2-yl |
| 199 | H | Me | cyclopentyl | H | OMe | CH2NH-(1-methylpyrrol-2-yl) |
| 200 | H | Me | cyclopentyl | H | OMe | CH2OCH2-(1,3-dimethylpyrazol-5-yl) |
| 201 | H | Me | cyclopentyl | H | NH2 | H |
| 202 | H | Me | cyclopentyl | H | NH2 | OMe |
| 203 | H | Me | cyclopentyl | H | NH2 | F |

TABLE 1-continued

| Compound No | X | R1 | R2 | R3 | R4 | R5 |
|---|---|---|---|---|---|---|
| 204 | H | Me | cyclopentyl | H | NH$_2$ | Cl |
| 205 | H | Me | cyclopentyl | H | NH$_2$ | Br |
| 206 | H | Me | cyclopentyl | H | NH$_2$ | I |
| 207 | H | Me | cyclopentyl | H | NH$_2$ | 2-methoxypyridin-yl (O-linked) |
| 208 | H | Me | cyclopentyl | H | NH$_2$ | 2-methoxypyridine N-oxide (O-linked) |
| 209 | H | Me | cyclopentyl | H | NH$_2$ | 3-methoxypyridin-yl (O-linked) |
| 210 | H | Me | cyclopentyl | H | NH$_2$ | 3-methoxypyridine N-oxide (O-linked) |
| 211 | H | Me | cyclopentyl | H | NH$_2$ | 4-methoxypyridin-yl (O-linked) |
| 212 | H | Me | cyclopentyl | H | NH$_2$ | 4-methoxypyridine N-oxide (O-linked) |
| 213 | H | Me | cyclopentyl | H | NH$_2$ | 2-(methoxymethyl)pyridine |
| 214 | H | Me | cyclopentyl | H | NH$_2$ | 2-(methoxymethyl)pyridine N-oxide |
| 215 | H | Me | cyclopentyl | H | NH$_2$ | 3-(methoxymethyl)pyridine |
| 216 | H | Me | cyclopentyl | H | NH$_2$ | 3-(methoxymethyl)pyridine N-oxide |

TABLE 1-continued

| Compound No | X | R1 | R2 | R3 | R4 | R5 |
|---|---|---|---|---|---|---|
| 217 | H | Me | cyclopentyl | H | NH$_2$ | -OCH$_2$-(4-pyridyl) |
| 218 | H | Me | cyclopentyl | H | NH$_2$ | -OCH$_2$-(4-pyridyl N-oxide) |
| 219 | H | Me | cyclopentyl | H | NH$_2$ | -OCH$_2$CH$_2$-(2-pyridyl) |
| 220 | H | Me | cyclopentyl | H | NH$_2$ | -OCH$_2$CH$_2$-(2-pyridyl N-oxide) |
| 221 | H | Me | cyclopentyl | H | NH$_2$ | -OCH$_2$CH$_2$-(3-pyridyl) |
| 222 | H | Me | cyclopentyl | H | NH$_2$ | -OCH$_2$CH$_2$-(3-pyridyl N-oxide) |
| 223 | H | Me | cyclopentyl | H | NH$_2$ | -OCH$_2$CH$_2$-(4-pyridyl) |
| 224 | H | Me | cyclopentyl | H | NH$_2$ | -OCH$_2$CH$_2$-(4-pyridyl N-oxide) |
| 225 | H | Me | cyclopentyl | H | NH$_2$ | -OCH$_2$CH$_2$CH$_2$-(2-pyridyl) |
| 226 | H | Me | cyclopentyl | H | NH$_2$ | -OCH$_2$CH$_2$CH$_2$-(2-pyridyl N-oxide) |
| 227 | H | Me | cyclopentyl | H | NH$_2$ | -OCH$_2$CH$_2$CH$_2$-(3-pyridyl) |
| 228 | H | Me | cyclopentyl | H | NH$_2$ | -OCH$_2$CH$_2$CH$_2$-(3-pyridyl N-oxide) |

TABLE 1-continued

| Compound No | X | R1 | R2 | R3 | R4 | R5 |
|---|---|---|---|---|---|---|
| 229 | H | Me | cyclopentyl | H | NH$_2$ | 3-(pyridin-4-yl)propyl methyl ether |
| 230 | H | Me | cyclopentyl | H | NH$_2$ | 3-(pyridin-4-yl N-oxide)propyl methyl ether |
| 231 | H | Me | cyclopentyl | H | NH$_2$ | N-methyl-2-phenylethylamine |
| 232 | H | Me | cyclopentyl | H | NH$_2$ | N,N-dimethyl-2-phenylethylamine |
| 233 | H | Me | cyclopentyl | H | NH$_2$ | N-methyl-2-(pyridin-2-yl)ethylamine |
| 234 | H | Me | cyclopentyl | H | NH$_2$ | N,N-dimethyl-2-(pyridin-2-yl)ethylamine |
| 235 | H | Me | cyclopentyl | H | NH$_2$ | N-methyl-2-(pyridin-3-yl)ethylamine |
| 236 | H | Me | cyclopentyl | H | NH$_2$ | N,N-dimethyl-2-(pyridin-3-yl)ethylamine |
| 237 | H | Me | cyclopentyl | H | NH$_2$ | N-methyl-2-(pyridin-4-yl)ethylamine |
| 238 | H | Me | cyclopentyl | H | NH$_2$ | N,N-dimethyl-2-(pyridin-4-yl)ethylamine |
| 239 | H | Me | cyclopentyl | H | NH$_2$ | (pyridazin-3-yl)methyl methyl ether |

TABLE 1-continued

| Compound No | X | R1 | R2 | R3 | R4 | R5 |
|---|---|---|---|---|---|---|
| 240 | H | Me | cyclopentyl | H | NH$_2$ | -OCH$_2$-(pyrazine) |
| 241 | H | Me | cyclopentyl | H | NH$_2$ | -OCH$_2$-(pyrazine N-oxide) |
| 242 | H | Me | cyclopentyl | H | NH$_2$ | -NHCH$_2$-(pyridazine) |
| 243 | H | Me | cyclopentyl | H | NH$_2$ | -OCH$_2$-(furan-3-yl) |
| 244 | H | Me | cyclopentyl | H | NH$_2$ | -OCH$_2$-(thiophen-3-yl) |
| 245 | H | Me | cyclopentyl | H | NH$_2$ | -OCH$_2$-(imidazol-4-yl) |
| 246 | H | Me | cyclopentyl | H | NH$_2$ | -NHCH$_2$-(furan-2-yl) |
| 247 | H | Me | cyclopentyl | H | NH$_2$ | -NHCH$_2$-(thiophen-2-yl) |
| 248 | H | Me | cyclopentyl | H | NH$_2$ | -NHCH$_2$-(1H-pyrrol-2-yl) |
| 249 | H | Me | cyclopentyl | H | NH$_2$ | -NHCH$_2$-(1-methyl-pyrrol-2-yl) |
| 250 | H | Me | cyclopentyl | H | NH$_2$ | -OCH$_2$-(1,3-dimethyl-pyrazol-5-yl) |
| 251 | H | Me | cyclopentyl | H | NHMe | H |
| 252 | H | Me | cyclopentyl | H | NHMe | OMe |
| 253 | H | Me | cyclopentyl | H | NHMe | F |

TABLE 1-continued

| Compound No | X | R1 | R2 | R3 | R4 | R5 |
|---|---|---|---|---|---|---|
| 254 | H | Me | cyclopentyl | H | NHMe | Cl |
| 255 | H | Me | cyclopentyl | H | NHMe | Br |
| 256 | H | Me | cyclopentyl | H | NHMe | I |
| 257 | H | Me | cyclopentyl | H | NHMe | 2-methoxypyridin-yl |
| 258 | H | Me | cyclopentyl | H | NHMe | 2-methoxypyridine N-oxide |
| 259 | H | Me | cyclopentyl | H | NHMe | 3-methoxypyridin-yl |
| 260 | H | Me | cyclopentyl | H | NHMe | 3-methoxypyridine N-oxide |
| 261 | H | Me | cyclopentyl | H | NHMe | 4-methoxypyridin-yl |
| 262 | H | Me | cyclopentyl | H | NHMe | 4-methoxypyridine N-oxide |
| 263 | H | Me | cyclopentyl | H | NHMe | 2-(methoxymethyl)pyridine |
| 264 | H | Me | cyclopentyl | H | NHMe | 2-(methoxymethyl)pyridine N-oxide |
| 265 | H | Me | cyclopentyl | H | NHMe | 3-(methoxymethyl)pyridine |
| 266 | H | Me | cyclopentyl | H | NHMe | 3-(methoxymethyl)pyridine N-oxide |

TABLE 1-continued

| Compound No | X | R1 | R2 | R3 | R4 | R5 |
|---|---|---|---|---|---|---|
| 267 | H | Me | cyclopentyl | H | NHMe | 4-(methoxymethyl)pyridine |
| 268 | H | Me | cyclopentyl | H | NHMe | 4-(methoxymethyl)pyridine N-oxide |
| 269 | H | Me | cyclopentyl | H | NHMe | 2-(2-methoxyethyl)pyridine |
| 270 | H | Me | cyclopentyl | H | NHMe | 2-(2-methoxyethyl)pyridine N-oxide |
| 271 | H | Me | cyclopentyl | H | NHMe | 3-(2-methoxyethyl)pyridine |
| 272 | H | Me | cyclopentyl | H | NHMe | 3-(2-methoxyethyl)pyridine N-oxide |
| 273 | H | Me | cyclopentyl | H | NHMe | 4-(2-methoxyethyl)pyridine |
| 274 | H | Me | cyclopentyl | H | NHMe | 4-(2-methoxyethyl)pyridine N-oxide |
| 275 | H | Me | cyclopentyl | H | NHMe | 2-(3-methoxypropyl)pyridine |
| 276 | H | Me | cyclopentyl | H | NHMe | 2-(3-methoxypropyl)pyridine N-oxide |
| 277 | H | Me | cyclopentyl | H | NHMe | 3-(3-methoxypropyl)pyridine |
| 278 | H | Me | cyclopentyl | H | NHMe | 3-(3-methoxypropyl)pyridine N-oxide |

TABLE 1-continued
| Compound No | X | R1 | R2 | R3 | R4 | R5 |
|---|---|---|---|---|---|---|
| 279 | H | Me |  | H | NHMe | 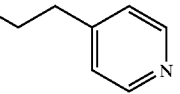 |
| 280 | H | Me |  | H | NHMe | 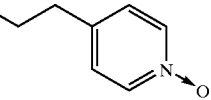 |
| 281 | H | Me |  | H | NHMe | 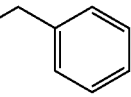 |
| 282 | H | Me |  | H | NHMe | 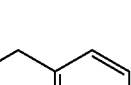 |
| 283 | H | Me |  | H | NHMe | 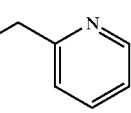 |
| 284 | H | Me |  | H | NHMe | 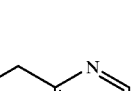 |
| 285 | H | Me |  | H | NHMe | 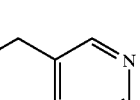 |
| 286 | H | Me |  | H | NHMe |  |
| 287 | H | Me |  | H | NHMe | 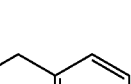 |
| 288 | H | Me |  | H | NHMe | 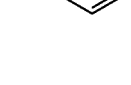 |
| 289 | H | Me |  | H | NHMe |  |

TABLE 1-continued

| Compound No | X | R1 | R2 | R3 | R4 | R5 |
|---|---|---|---|---|---|---|
| 290 | H | Me | cyclopentyl | H | NHMe | -OCH2-pyrazine |
| 291 | H | Me | cyclopentyl | H | NHMe | -OCH2-pyrazine N-oxide |
| 292 | H | Me | cyclopentyl | H | NHMe | -NHCH2-pyridazine |
| 293 | H | Me | cyclopentyl | H | NHMe | -OCH2-furan (3-yl) |
| 294 | H | Me | cyclopentyl | H | NHMe | -OCH2-thiophene (3-yl) |
| 295 | H | Me | cyclopentyl | H | NHMe | -OCH2-imidazole |
| 296 | H | Me | cyclopentyl | H | NHMe | -NHCH2-furan (2-yl) |
| 297 | H | Me | cyclopentyl | H | NHMe | -NHCH2-thiophene (2-yl) |
| 298 | H | Me | cyclopentyl | H | NHMe | -NHCH2-pyrrole |
| 299 | H | Me | cyclopentyl | H | NHMe | -NHCH2-(N-Me-pyrrole) |
| 300 | H | Me | cyclopentyl | H | NHMe | -OCH2-(1,3-dimethylpyrazole) |
| 301 | H | Me | cyclopentyl | H | NHEt | H |
| 302 | H | Me | cyclopentyl | H | NHEt | OMe |
| 303 | H | Me | cyclopentyl | H | NHEt | F |

TABLE 1-continued

| Compound No | X | R1 | R2 | R3 | R4 | R5 |
|---|---|---|---|---|---|---|
| 304 | H | Me | cyclopentyl | H | NHEt | Cl |
| 305 | H | Me | cyclopentyl | H | NHEt | Br |
| 306 | H | Me | cyclopentyl | H | NHEt | I |
| 307 | H | Me | cyclopentyl | H | NHEt | 2-methoxypyridin-yl |
| 308 | H | Me | cyclopentyl | H | NHEt | 2-methoxypyridin-yl N-oxide |
| 309 | H | Me | cyclopentyl | H | NHEt | 3-methoxypyridin-yl |
| 310 | H | Me | cyclopentyl | H | NHEt | 3-methoxypyridin-yl N-oxide |
| 311 | H | Me | cyclopentyl | H | NHEt | 4-methoxypyridin-yl |
| 312 | H | Me | cyclopentyl | H | NHEt | 4-methoxypyridin-yl N-oxide |
| 313 | H | Me | cyclopentyl | H | NHEt | 2-(methoxymethyl)pyridin-yl |
| 314 | H | Me | cyclopentyl | H | NHEt | 2-(methoxymethyl)pyridin-yl N-oxide |
| 315 | H | Me | cyclopentyl | H | NHEt | 3-(methoxymethyl)pyridin-yl |
| 316 | H | Me | cyclopentyl | H | NHEt | 3-(methoxymethyl)pyridin-yl N-oxide |

TABLE 1-continued

| Compound No | X | R1 | R2 | R3 | R4 | R5 |
|---|---|---|---|---|---|---|
| 317 | H | Me | cyclopentyl | H | NHEt | MeOCH2-(pyridin-4-yl) |
| 318 | H | Me | cyclopentyl | H | NHEt | MeOCH2-(pyridin-4-yl) N-oxide |
| 319 | H | Me | cyclopentyl | H | NHEt | MeO(CH2)2-(pyridin-2-yl) |
| 320 | H | Me | cyclopentyl | H | NHEt | MeO(CH2)2-(pyridin-2-yl) N-oxide |
| 321 | H | Me | cyclopentyl | H | NHEt | MeO(CH2)2-(pyridin-3-yl) |
| 322 | H | Me | cyclopentyl | H | NHEt | MeO(CH2)2-(pyridin-3-yl) N-oxide |
| 323 | H | Me | cyclopentyl | H | NHEt | MeO(CH2)2-(pyridin-4-yl) |
| 324 | H | Me | cyclopentyl | H | NHEt | MeO(CH2)2-(pyridin-4-yl) N-oxide |
| 325 | H | Me | cyclopentyl | H | NHEt | MeO(CH2)3-(pyridin-2-yl) |
| 326 | H | Me | cyclopentyl | H | NHEt | MeO(CH2)3-(pyridin-2-yl) N-oxide |
| 327 | H | Me | cyclopentyl | H | NHEt | MeO(CH2)3-(pyridin-3-yl) |
| 328 | H | Me | cyclopentyl | H | NHEt | MeO(CH2)3-(pyridin-3-yl) N-oxide |

TABLE 1-continued

| Compound No | X | R1 | R2 | R3 | R4 | R5 |
|---|---|---|---|---|---|---|
| 329 | H | Me | cyclopentyl | H | NHEt | methoxypropyl-(4-pyridyl) |
| 330 | H | Me | cyclopentyl | H | NHEt | methoxypropyl-(4-pyridyl N-oxide) |
| 331 | H | Me | cyclopentyl | H | NHEt | NH-CH2-CH2-phenyl |
| 332 | H | Me | cyclopentyl | H | NHEt | N(Me)-CH2-CH2-phenyl |
| 333 | H | Me | cyclopentyl | H | NHEt | NH-CH2-CH2-(2-pyridyl) |
| 334 | H | Me | cyclopentyl | H | NHEt | N(Me)-CH2-CH2-(2-pyridyl) |
| 335 | H | Me | cyclopentyl | H | NHEt | NH-CH2-CH2-(3-pyridyl) |
| 336 | H | Me | cyclopentyl | H | NHEt | N(Me)-CH2-CH2-(3-pyridyl) |
| 337 | H | Me | cyclopentyl | H | NHEt | NH-CH2-CH2-(4-pyridyl) |
| 338 | H | Me | cyclopentyl | H | NHEt | N(Me)-CH2-CH2-(4-pyridyl) |
| 339 | H | Me | cyclopentyl | H | NHEt | methoxymethyl-pyridazinyl |

TABLE 1-continued

| Compound No | X | R1 | R2 | R3 | R4 | R5 |
|---|---|---|---|---|---|---|
| 340 | H | Me | cyclopentyl | H | NHEt | methoxymethyl-pyrazine |
| 341 | H | Me | cyclopentyl | H | NHEt | methoxymethyl-pyrazine N-oxide |
| 342 | H | Me | cyclopentyl | H | NHEt | NH-methyl-pyridazine |
| 343 | H | Me | cyclopentyl | H | NHEt | methoxymethyl-furan |
| 344 | H | Me | cyclopentyl | H | NHEt | methoxymethyl-thiophene |
| 345 | H | Me | cyclopentyl | H | NHEt | methoxymethyl-imidazole |
| 346 | H | Me | cyclopentyl | H | NHEt | NH-methyl-furan |
| 347 | H | Me | cyclopentyl | H | NHEt | NH-methyl-thiophene |
| 348 | H | Me | cyclopentyl | H | NHEt | NH-methyl-pyrrole |
| 349 | H | Me | cyclopentyl | H | NHEt | NH-methyl-(N-Me)pyrrole |
| 350 | H | Me | cyclopentyl | H | NHEt | methoxymethyl-(1,3-diMe)pyrazole |
| 351 | H | Me | cyclopentyl | H | NHn-Pr | H |
| 352 | H | Me | cyclopentyl | H | NHn-Pr | OMe |
| 353 | H | Me | cyclopentyl | H | NHn-Pr | F |

TABLE 1-continued

| Compound No | X | R1 | R2 | R3 | R4 | R5 |
|---|---|---|---|---|---|---|
| 354 | H | Me | cyclopentyl | H | NHn-Pr | Cl |
| 355 | H | Me | cyclopentyl | H | NHn-Pr | Br |
| 356 | H | Me | cyclopentyl | H | NHn-Pr | I |
| 357 | H | Me | cyclopentyl | H | NHn-Pr | 2-methoxypyridin-yl |
| 358 | H | Me | cyclopentyl | H | NHn-Pr | 2-methoxypyridine N-oxide |
| 359 | H | Me | cyclopentyl | H | NHn-Pr | 3-methoxypyridin-yl |
| 360 | H | Me | cyclopentyl | H | NHn-Pr | 3-methoxypyridine N-oxide |
| 361 | H | Me | cyclopentyl | H | NHn-Pr | 4-methoxypyridin-yl |
| 362 | H | Me | cyclopentyl | H | NHn-Pr | 4-methoxypyridine N-oxide |
| 363 | H | Me | cyclopentyl | H | NHn-Pr | 2-(methoxymethyl)pyridin-yl |
| 364 | H | Me | cyclopentyl | H | NHn-Pr | 2-(methoxymethyl)pyridine N-oxide |
| 365 | H | Me | cyclopentyl | H | NHn-Pr | 3-(methoxymethyl)pyridin-yl |
| 366 | H | Me | cyclopentyl | H | NHn-Pr | 3-(methoxymethyl)pyridine N-oxide |

TABLE 1-continued

| Compound No | X | R1 | R2 | R3 | R4 | R5 |
|---|---|---|---|---|---|---|
| 367 | H | Me | cyclopentyl | H | NHn-Pr | CH₂O-CH₂-(4-pyridyl) |
| 368 | H | Me | cyclopentyl | H | NHn-Pr | CH₂O-CH₂-(4-pyridyl N-oxide) |
| 369 | H | Me | cyclopentyl | H | NHn-Pr | CH₂O-(CH₂)₂-(2-pyridyl) |
| 370 | H | Me | cyclopentyl | H | NHn-Pr | CH₂O-(CH₂)₂-(2-pyridyl N-oxide) |
| 371 | H | Me | cyclopentyl | H | NHn-Pr | CH₂O-(CH₂)₂-(3-pyridyl) |
| 372 | H | Me | cyclopentyl | H | NHn-Pr | CH₂O-(CH₂)₂-(3-pyridyl N-oxide) |
| 373 | H | Me | cyclopentyl | H | NHn-Pr | CH₂O-(CH₂)₂-(4-pyridyl) |
| 374 | H | Me | cyclopentyl | H | NHn-Pr | CH₂O-(CH₂)₂-(4-pyridyl N-oxide) |
| 375 | H | Me | cyclopentyl | H | NHn-Pr | CH₂O-(CH₂)₃-(2-pyridyl) |
| 376 | H | Me | cyclopentyl | H | NHn-Pr | CH₂O-(CH₂)₃-(2-pyridyl N-oxide) |
| 377 | H | Me | cyclopentyl | H | NHn-Pr | CH₂O-(CH₂)₃-(3-pyridyl) |
| 378 | H | Me | cyclopentyl | H | NHn-Pr | CH₂O-(CH₂)₃-(3-pyridyl N-oxide) |

TABLE 1-continued

| Compound No | X | R1 | R2 | R3 | R4 | R5 |
|---|---|---|---|---|---|---|
| 379 | H | Me | cyclopentyl | H | NHn-Pr | methoxypropyl-(pyridin-4-yl) |
| 380 | H | Me | cyclopentyl | H | NHn-Pr | methoxypropyl-(pyridin-4-yl N-oxide) |
| 381 | H | Me | cyclopentyl | H | NHn-Pr | NH-CH2-CH2-phenyl |
| 382 | H | Me | cyclopentyl | H | NHn-Pr | N(Me)-CH2-CH2-phenyl |
| 383 | H | Me | cyclopentyl | H | NHn-Pr | NH-CH2-CH2-(pyridin-2-yl) |
| 384 | H | Me | cyclopentyl | H | NHn-Pr | N(Me)-CH2-CH2-(pyridin-2-yl) |
| 385 | H | Me | cyclopentyl | H | NHn-Pr | NH-CH2-CH2-(pyridin-3-yl) |
| 386 | H | Me | cyclopentyl | H | NHn-Pr | N(Me)-CH2-CH2-(pyridin-3-yl) |
| 387 | H | Me | cyclopentyl | H | NHn-Pr | NH-CH2-CH2-(pyridin-4-yl) |
| 388 | H | Me | cyclopentyl | H | NHn-Pr | N(Me)-CH2-CH2-(pyridin-4-yl) |
| 389 | H | Me | cyclopentyl | H | NHn-Pr | methoxymethyl-(pyridazin-3-yl) |

TABLE 1-continued

| Compound No | X | R1 | R2 | R3 | R4 | R5 |
|---|---|---|---|---|---|---|
| 390 | H | Me | cyclopentyl | H | NHn-Pr | methoxymethyl-pyrazine |
| 391 | H | Me | cyclopentyl | H | NHn-Pr | methoxymethyl-pyrazine N-oxide |
| 392 | H | Me | cyclopentyl | H | NHn-Pr | NH-CH2-pyridazine |
| 393 | H | Me | cyclopentyl | H | NHn-Pr | methoxymethyl-furan |
| 394 | H | Me | cyclopentyl | H | NHn-Pr | methoxymethyl-thiophene |
| 395 | H | Me | cyclopentyl | H | NHn-Pr | methoxymethyl-imidazole |
| 396 | H | Me | cyclopentyl | H | NHn-Pr | NH-CH2-furan |
| 397 | H | Me | cyclopentyl | H | NHn-Pr | NH-CH2-thiophene |
| 398 | H | Me | cyclopentyl | H | NHn-Pr | NH-CH2-pyrrole |
| 399 | H | Me | cyclopentyl | H | NHn-Pr | NH-CH2-(N-Me-pyrrole) |
| 400 | H | Me | cyclopentyl | H | NHn-Pr | methoxymethyl-(1,3-dimethylpyrazole) |
| 401 | H | Me | cyclopentyl | H | NMe2 | H |
| 402 | H | Me | cyclopentyl | H | NMe2 | OMe |
| 403 | H | Me | cyclopentyl | H | NMe2 | F |

TABLE 1-continued

| Compound No | X | R1 | R2 | R3 | R4 | R5 |
|---|---|---|---|---|---|---|
| 404 | H | Me | cyclopentyl | H | NMe$_2$ | Cl |
| 405 | H | Me | cyclopentyl | H | NMe$_2$ | Br |
| 406 | H | Me | cyclopentyl | H | NMe$_2$ | I |
| 407 | H | Me | cyclopentyl | H | NMe$_2$ | 2-methoxypyridin-yl |
| 408 | H | Me | cyclopentyl | H | NMe$_2$ | 2-methoxypyridine N-oxide |
| 409 | H | Me | cyclopentyl | H | NMe$_2$ | 3-methoxypyridin-yl |
| 410 | H | Me | cyclopentyl | H | NMe$_2$ | 3-methoxypyridine N-oxide |
| 411 | H | Me | cyclopentyl | H | NMe$_2$ | 4-methoxypyridin-yl |
| 412 | H | Me | cyclopentyl | H | NMe$_2$ | 4-methoxypyridine N-oxide |
| 413 | H | Me | cyclopentyl | H | NMe$_2$ | 2-(methoxymethyl)pyridine |
| 414 | H | Me | cyclopentyl | H | NMe$_2$ | 2-(methoxymethyl)pyridine N-oxide |
| 415 | H | Me | cyclopentyl | H | NMe$_2$ | 3-(methoxymethyl)pyridine |
| 416 | H | Me | cyclopentyl | H | NMe$_2$ | 3-(methoxymethyl)pyridine N-oxide |

TABLE 1-continued

| Compound No | X | R1 | R2 | R3 | R4 | R5 |
|---|---|---|---|---|---|---|
| 417 | H | Me | cyclopentyl | H | NMe$_2$ | -OCH$_2$-(pyridin-4-yl) |
| 418 | H | Me | cyclopentyl | H | NMe$_2$ | -OCH$_2$-(pyridin-4-yl N-oxide) |
| 419 | H | Me | cyclopentyl | H | NMe$_2$ | -OCH$_2$CH$_2$-(pyridin-2-yl) |
| 420 | H | Me | cyclopentyl | H | NMe$_2$ | -OCH$_2$CH$_2$-(pyridin-2-yl N-oxide) |
| 421 | H | Me | cyclopentyl | H | NMe$_2$ | -OCH$_2$CH$_2$-(pyridin-3-yl) |
| 422 | H | Me | cyclopentyl | H | NMe$_2$ | -OCH$_2$CH$_2$-(pyridin-3-yl N-oxide) |
| 423 | H | Me | cyclopentyl | H | NMe$_2$ | -OCH$_2$CH$_2$-(pyridin-4-yl) |
| 424 | H | Me | cyclopentyl | H | NMe$_2$ | -OCH$_2$CH$_2$-(pyridin-4-yl N-oxide) |
| 425 | H | Me | cyclopentyl | H | NMe$_2$ | -OCH$_2$CH$_2$CH$_2$-(pyridin-2-yl) |
| 426 | H | Me | cyclopentyl | H | NMe$_2$ | -OCH$_2$CH$_2$CH$_2$-(pyridin-2-yl N-oxide) |
| 427 | H | Me | cyclopentyl | H | NMe$_2$ | -OCH$_2$CH$_2$CH$_2$-(pyridin-3-yl) |
| 428 | H | Me | cyclopentyl | H | NMe$_2$ | -OCH$_2$CH$_2$CH$_2$-(pyridin-3-yl N-oxide) |

TABLE 1-continued

| Compound No | X | R1 | R2 | R3 | R4 | R5 |
|---|---|---|---|---|---|---|
| 429 | H | Me | cyclopentyl | H | NMe$_2$ | -O-CH$_2$CH$_2$CH$_2$-(4-pyridyl), methoxy linker |
| 430 | H | Me | cyclopentyl | H | NMe$_2$ | -O-CH$_2$CH$_2$CH$_2$-(4-pyridyl N-oxide) |
| 431 | H | Me | cyclopentyl | H | NMe$_2$ | -NH-CH$_2$CH$_2$-phenyl |
| 432 | H | Me | cyclopentyl | H | NMe$_2$ | -N(Me)-CH$_2$CH$_2$-phenyl |
| 433 | H | Me | cyclopentyl | H | NMe$_2$ | -NH-CH$_2$CH$_2$-(2-pyridyl) |
| 434 | H | Me | cyclopentyl | H | NMe$_2$ | -N(Me)-CH$_2$CH$_2$-(2-pyridyl) |
| 435 | H | Me | cyclopentyl | H | NMe$_2$ | -NH-CH$_2$CH$_2$-(3-pyridyl) |
| 436 | H | Me | cyclopentyl | H | NMe$_2$ | -N(Me)-CH$_2$CH$_2$-(3-pyridyl) |
| 437 | H | Me | cyclopentyl | H | NMe$_2$ | -NH-CH$_2$CH$_2$-(4-pyridyl) |
| 438 | H | Me | cyclopentyl | H | NMe$_2$ | -N(Me)-CH$_2$CH$_2$-(4-pyridyl) |
| 439 | H | Me | cyclopentyl | H | NMe$_2$ | -O-CH$_2$-(3-pyridazinyl) |

TABLE 1-continued

| Compound No | X | R1 | R2 | R3 | R4 | R5 |
|---|---|---|---|---|---|---|
| 440 | H | Me | cyclopentyl | H | NMe$_2$ | -OCH$_2$-pyrazinyl |
| 441 | H | Me | cyclopentyl | H | NMe$_2$ | -OCH$_2$-pyrazinyl N-oxide |
| 442 | H | Me | cyclopentyl | H | NMe$_2$ | -NHCH$_2$-pyridazinyl |
| 443 | H | Me | cyclopentyl | H | NMe$_2$ | -OCH$_2$-furyl |
| 444 | H | Me | cyclopentyl | H | NMe$_2$ | -OCH$_2$-thienyl |
| 445 | H | Me | cyclopentyl | H | NMe$_2$ | -OCH$_2$-imidazolyl |
| 446 | H | Me | cyclopentyl | H | NMe$_2$ | -NHCH$_2$-furyl |
| 447 | H | Me | cyclopentyl | H | NMe$_2$ | -NHCH$_2$-thienyl |
| 448 | H | Me | cyclopentyl | H | NMe$_2$ | -NHCH$_2$-pyrrolyl |
| 449 | H | Me | cyclopentyl | H | NMe$_2$ | -NHCH$_2$-(N-Me-pyrrolyl) |
| 450 | H | Me | cyclopentyl | H | NMe$_2$ | -OCH$_2$-(1,3-diMe-pyrazolyl) |
| 451 | H | Me | cyclopentyl | H | Cl | H |
| 452 | H | Me | cyclopentyl | H | Cl | OMe |
| 453 | H | Me | cyclopentyl | H | Cl | F |

TABLE 1-continued

| Compound No | X | R1 | R2 | R3 | R4 | R5 |
|---|---|---|---|---|---|---|
| 454 | H | Me | cyclopentyl | H | Cl | Cl |
| 455 | H | Me | cyclopentyl | H | Cl | Br |
| 456 | H | Me | cyclopentyl | H | Cl | I |
| 457 | H | Me | cyclopentyl | H | Cl | 2-methoxypyridin-yl |
| 458 | H | Me | cyclopentyl | H | Cl | 2-methoxypyridin-yl N-oxide |
| 459 | H | Me | cyclopentyl | H | Cl | 3-methoxypyridin-yl |
| 460 | H | Me | cyclopentyl | H | Cl | 3-methoxypyridin-yl N-oxide |
| 461 | H | Me | cyclopentyl | H | Cl | 4-methoxypyridin-yl |
| 462 | H | Me | cyclopentyl | H | Cl | 4-methoxypyridin-yl N-oxide |
| 463 | H | Me | cyclopentyl | H | Cl | 2-(methoxymethyl)pyridin-yl |
| 464 | H | Me | cyclopentyl | H | Cl | 2-(methoxymethyl)pyridin-yl N-oxide |
| 465 | H | Me | cyclopentyl | H | Cl | 3-(methoxymethyl)pyridin-yl |
| 466 | H | Me | cyclopentyl | H | Cl | 3-(methoxymethyl)pyridin-yl N-oxide |

TABLE 1-continued

| Compound No | X | R1 | R2 | R3 | R4 | R5 |
|---|---|---|---|---|---|---|
| 467 | H | Me | cyclopentyl | H | Cl | 4-(methoxymethyl)pyridine |
| 468 | H | Me | cyclopentyl | H | Cl | 4-(methoxymethyl)pyridine N-oxide |
| 469 | H | Me | cyclopentyl | H | Cl | 2-(2-methoxyethyl)pyridine |
| 470 | H | Me | cyclopentyl | H | Cl | 2-(2-methoxyethyl)pyridine N-oxide |
| 471 | H | Me | cyclopentyl | H | Cl | 3-(2-methoxyethyl)pyridine |
| 472 | H | Me | cyclopentyl | H | Cl | 3-(2-methoxyethyl)pyridine N-oxide |
| 473 | H | Me | cyclopentyl | H | Cl | 4-(2-methoxyethyl)pyridine |
| 474 | H | Me | cyclopentyl | H | Cl | 4-(2-methoxyethyl)pyridine N-oxide |
| 475 | H | Me | cyclopentyl | H | Cl | 2-(3-methoxypropyl)pyridine |
| 476 | H | Me | cyclopentyl | H | Cl | 2-(3-methoxypropyl)pyridine N-oxide |
| 477 | H | Me | cyclopentyl | H | Cl | 3-(3-methoxypropyl)pyridine |
| 478 | H | Me | cyclopentyl | H | Cl | 3-(3-methoxypropyl)pyridine N-oxide |

TABLE 1-continued

| Compound No | X | R1 | R2 | R3 | R4 | R5 |
|---|---|---|---|---|---|---|
| 479 | H | Me | cyclopentyl | H | Cl | 3-(4-pyridyl)propoxymethyl (OCH2CH2CH2-4-pyridyl with OMe) |
| 480 | H | Me | cyclopentyl | H | Cl | 3-(4-pyridyl N-oxide)propoxymethyl |
| 481 | H | Me | cyclopentyl | H | Cl | NH-CH2CH2-phenyl |
| 482 | H | Me | cyclopentyl | H | Cl | N(Me)-CH2CH2-phenyl |
| 483 | H | Me | cyclopentyl | H | Cl | NH-CH2CH2-(2-pyridyl) |
| 484 | H | Me | cyclopentyl | H | Cl | N(Me)-CH2CH2-(2-pyridyl) |
| 485 | H | Me | cyclopentyl | H | Cl | NH-CH2CH2-(3-pyridyl) |
| 486 | H | Me | cyclopentyl | H | Cl | N(Me)-CH2CH2-(3-pyridyl) |
| 487 | H | Me | cyclopentyl | H | Cl | NH-CH2CH2-(4-pyridyl) |
| 488 | H | Me | cyclopentyl | H | Cl | N(Me)-CH2CH2-(4-pyridyl) |
| 489 | H | Me | cyclopentyl | H | Cl | (3-pyridazinyl)methoxymethyl |

TABLE 1-continued

| Compound No | X | R1 | R2 | R3 | R4 | R5 |
|---|---|---|---|---|---|---|
| 490 | H | Me | cyclopentyl | H | Cl | -OCH2-pyrazinyl |
| 491 | H | Me | cyclopentyl | H | Cl | -OCH2-pyrazinyl N-oxide |
| 492 | H | Me | cyclopentyl | H | Cl | -NHCH2-pyridazinyl |
| 493 | H | Me | cyclopentyl | H | Cl | -OCH2-furanyl |
| 494 | H | Me | cyclopentyl | H | Cl | -OCH2-thienyl |
| 495 | H | Me | cyclopentyl | H | Cl | -OCH2-imidazolyl |
| 496 | H | Me | cyclopentyl | H | Cl | -NHCH2-furanyl |
| 497 | H | Me | cyclopentyl | H | Cl | -NHCH2-thienyl |
| 498 | H | Me | cyclopentyl | H | Cl | -NHCH2-pyrrolyl |
| 499 | H | Me | cyclopentyl | H | Cl | -NHCH2-(N-Me-pyrrolyl) |
| 500 | H | Me | cyclopentyl | H | Cl | -OCH2-(1,3-diMe-pyrazolyl) |
| 501 | H | Me | cyclopentyl | H | pyrrolidinyl | H |
| 502 | H | Me | cyclopentyl | H | pyrrolidinyl | OMe |
| 503 | H | Me | cyclopentyl | H | pyrrolidinyl | F |

TABLE 1-continued

| Compound No | X | R1 | R2 | R3 | R4 | R5 |
|---|---|---|---|---|---|---|
| 504 | H | Me | cyclopentyl | H | pyrrolidinyl | Cl |
| 505 | H | Me | cyclopentyl | H | pyrrolidinyl | Br |
| 506 | H | Me | cyclopentyl | H | pyrrolidinyl | I |
| 507 | H | Me | cyclopentyl | H | pyrrolidinyl | 2-methoxypyridine (O-linked) |
| 508 | H | Me | cyclopentyl | H | pyrrolidinyl | 2-methoxypyridine N-oxide (O-linked) |
| 509 | H | Me | cyclopentyl | H | pyrrolidinyl | 3-methoxypyridine (O-linked) |
| 510 | H | Me | cyclopentyl | H | pyrrolidinyl | 3-methoxypyridine N-oxide (O-linked) |
| 511 | H | Me | cyclopentyl | H | pyrrolidinyl | 4-methoxypyridine (O-linked) |
| 512 | H | Me | cyclopentyl | H | pyrrolidinyl | 4-methoxypyridine N-oxide (O-linked) |
| 513 | H | Me | cyclopentyl | H | pyrrolidinyl | 2-(methoxymethyl)pyridine |
| 514 | H | Me | cyclopentyl | H | pyrrolidinyl | 2-(methoxymethyl)pyridine N-oxide |
| 515 | H | Me | cyclopentyl | H | pyrrolidinyl | 3-(methoxymethyl)pyridine |
| 516 | H | Me | cyclopentyl | H | pyrrolidinyl | 3-(methoxymethyl)pyridine N-oxide |

TABLE 1-continued

| Compound No | X | R1 | R2 | R3 | R4 | R5 |
|---|---|---|---|---|---|---|
| 517 | H | Me | cyclopentyl | H | pyrrolidinyl | -OCH2-(4-pyridyl) |
| 518 | H | Me | cyclopentyl | H | pyrrolidinyl | -OCH2-(4-pyridyl N-oxide) |
| 519 | H | Me | cyclopentyl | H | pyrrolidinyl | -O-CH2CH2-(2-pyridyl) |
| 520 | H | Me | cyclopentyl | H | pyrrolidinyl | -O-CH2CH2-(2-pyridyl N-oxide) |
| 521 | H | Me | cyclopentyl | H | pyrrolidinyl | -O-CH2CH2-(3-pyridyl) |
| 522 | H | Me | cyclopentyl | H | pyrrolidinyl | -O-CH2CH2-(3-pyridyl N-oxide) |
| 523 | H | Me | cyclopentyl | H | pyrrolidinyl | -O-CH2CH2-(4-pyridyl) |
| 524 | H | Me | cyclopentyl | H | pyrrolidinyl | -O-CH2CH2-(4-pyridyl N-oxide) |
| 525 | H | Me | cyclopentyl | H | pyrrolidinyl | -O-CH2CH2CH2-(2-pyridyl) |
| 526 | H | Me | cyclopentyl | H | pyrrolidinyl | -O-CH2CH2CH2-(2-pyridyl N-oxide) |
| 527 | H | Me | cyclopentyl | H | pyrrolidinyl | -O-CH2CH2CH2-(3-pyridyl) |
| 528 | H | Me | cyclopentyl | H | pyrrolidinyl | -O-CH2CH2CH2-(3-pyridyl N-oxide) |

TABLE 1-continued

| Compound No | X | R1 | R2 | R3 | R4 | R5 |
|---|---|---|---|---|---|---|
| 529 | H | Me | cyclopentyl | H | pyrrolidin-1-yl | 3-(pyridin-4-yl)propoxymethyl (CH₂OCH₂CH₂CH₂-(4-pyridyl)) |
| 530 | H | Me | cyclopentyl | H | pyrrolidin-1-yl | 3-(pyridin-4-yl N-oxide)propoxymethyl |
| 531 | H | Me | cyclopentyl | H | pyrrolidin-1-yl | NH-CH₂-CH₂-phenyl |
| 532 | H | Me | cyclopentyl | H | pyrrolidin-1-yl | N(Me)-CH₂-CH₂-phenyl |
| 533 | H | Me | cyclopentyl | H | pyrrolidin-1-yl | NH-CH₂-CH₂-(2-pyridyl) |
| 534 | H | Me | cyclopentyl | H | pyrrolidin-1-yl | N(Me)-CH₂-CH₂-(2-pyridyl) |
| 535 | H | Me | cyclopentyl | H | pyrrolidin-1-yl | NH-CH₂-CH₂-(3-pyridyl) |
| 536 | H | Me | cyclopentyl | H | pyrrolidin-1-yl | N(Me)-CH₂-CH₂-(3-pyridyl) |
| 537 | H | Me | cyclopentyl | H | pyrrolidin-1-yl | NH-CH₂-CH₂-(4-pyridyl) |
| 538 | H | Me | cyclopentyl | H | pyrrolidin-1-yl | N(Me)-CH₂-CH₂-(4-pyridyl) |
| 539 | H | Me | cyclopentyl | H | pyrrolidin-1-yl | (pyridazin-3-yl)methoxymethyl |

TABLE 1-continued
| Compound No | X | R1 | R2 | R3 | R4 | R5 |
|---|---|---|---|---|---|---|
| 540 | H | Me | 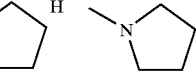 | H | 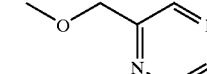 |  |
| 541 | H | Me | 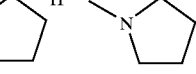 | H | 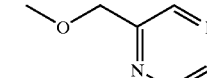 |  |
| 542 | H | Me | 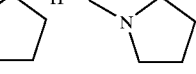 | H | 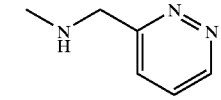 |  |
| 543 | H | Me | 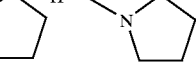 | H | 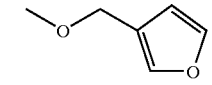 |  |
| 544 | H | Me | 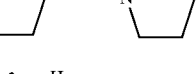 | H |  |  |
| 545 | H | Me | 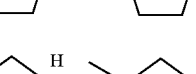 | H | 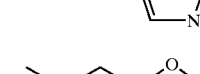 |  |
| 546 | H | Me | 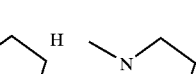 | H | 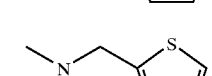 |  |
| 547 | H | Me | 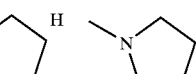 | H | 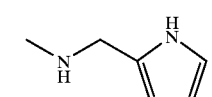 |  |
| 548 | H | Me | 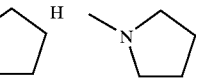 | H | 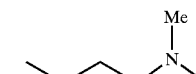 |  |
| 549 | H | Me | 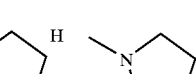 | H | 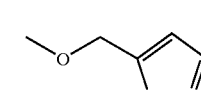 |  |
| 550 | H | Me |  | H | 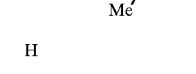 |  |
| 551 | H | Me | 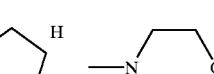 | H |  | H |
| 552 | H | Me |  | H | 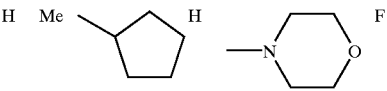 | OMe |
| 553 | H | Me |  | H |  | F |

TABLE 1-continued

| Compound No | X | R1 | R2 | R3 | R4 | R5 |
|---|---|---|---|---|---|---|
| 554 | H | Me | cyclopentyl | H | morpholino | Cl |
| 555 | H | Me | cyclopentyl | H | morpholino | Br |
| 556 | H | Me | cyclopentyl | H | morpholino | I |
| 557 | H | Me | cyclopentyl | H | morpholino | —O-(pyridin-2-yl) |
| 558 | H | Me | cyclopentyl | H | morpholino | —O-(pyridin-2-yl N-oxide) |
| 559 | H | Me | cyclopentyl | H | morpholino | —O-(pyridin-3-yl) |
| 560 | H | Me | cyclopentyl | H | morpholino | —O-(pyridin-3-yl N-oxide) |
| 561 | H | Me | cyclopentyl | H | morpholino | —O-(pyridin-4-yl) |
| 562 | H | Me | cyclopentyl | H | morpholino | —O-(pyridin-4-yl N-oxide) |
| 563 | H | Me | cyclopentyl | H | morpholino | —OCH$_2$-(pyridin-2-yl) |
| 564 | H | Me | cyclopentyl | H | morpholino | —OCH$_2$-(pyridin-2-yl N-oxide) |
| 565 | H | Me | cyclopentyl | H | morpholino | —OCH$_2$-(pyridin-3-yl) |

TABLE 1-continued

| Compound No | X | R1 | R2 | R3 | R4 | R5 |
|---|---|---|---|---|---|---|
| 566 | H | Me | cyclopentyl | H | morpholino | —OCH₂-(pyridin-3-yl N-oxide) |
| 567 | H | Me | cyclopentyl | H | morpholino | —OCH₂-(pyridin-4-yl) |
| 568 | H | Me | cyclopentyl | H | morpholino | —OCH₂-(pyridin-4-yl N-oxide) |
| 569 | H | Me | cyclopentyl | H | morpholino | —OCH₂CH₂-(pyridin-2-yl) |
| 570 | H | Me | cyclopentyl | H | morpholino | —OCH₂CH₂-(pyridin-2-yl N-oxide) |
| 571 | H | Me | cyclopentyl | H | morpholino | —OCH₂CH₂-(pyridin-3-yl) |
| 572 | H | Me | cyclopentyl | H | morpholino | —OCH₂CH₂-(pyridin-3-yl N-oxide) |
| 573 | H | Me | cyclopentyl | H | morpholino | —OCH₂CH₂-(pyridin-4-yl) |
| 574 | H | Me | cyclopentyl | H | morpholino | —OCH₂CH₂-(pyridin-4-yl N-oxide) |
| 575 | H | Me | cyclopentyl | H | morpholino | —OCH₂CH₂CH₂-(pyridin-2-yl) |
| 576 | H | Me | cyclopentyl | H | morpholino | —OCH₂CH₂CH₂-(pyridin-2-yl N-oxide) |
| 577 | H | Me | cyclopentyl | H | morpholino | —OCH₂CH₂CH₂-(pyridin-3-yl) |

TABLE 1-continued

| Compound No | X | R1 | R2 | R3 | R4 | R5 |
|---|---|---|---|---|---|---|
| 578 | H | Me | cyclopentyl | H | morpholinyl | 3-(3-methoxypropyl)pyridine N-oxide |
| 579 | H | Me | cyclopentyl | H | morpholinyl | 4-(3-methoxypropyl)pyridine |
| 580 | H | Me | cyclopentyl | H | morpholinyl | 4-(3-methoxypropyl)pyridine N-oxide |
| 581 | H | Me | cyclopentyl | H | morpholinyl | -NH-CH2CH2-phenyl |
| 582 | H | Me | cyclopentyl | H | morpholinyl | -N(Me)-CH2CH2-phenyl |
| 583 | H | Me | cyclopentyl | H | morpholinyl | -NH-CH2CH2-(2-pyridyl) |
| 584 | H | Me | cyclopentyl | H | morpholinyl | -N(Me)-CH2CH2-(2-pyridyl) |
| 585 | H | Me | cyclopentyl | H | morpholinyl | -NH-CH2CH2-(3-pyridyl) |
| 586 | H | Me | cyclopentyl | H | morpholinyl | -N(Me)-CH2CH2-(3-pyridyl) |
| 587 | H | Me | cyclopentyl | H | morpholinyl | -NH-CH2CH2-(4-pyridyl) |
| 588 | H | Me | cyclopentyl | H | morpholinyl | -N(Me)-CH2CH2-(4-pyridyl) |

TABLE 1-continued

| Compound No | X | R1 | R2 | R3 | R4 | R5 |
|---|---|---|---|---|---|---|
| 589 | H | Me | cyclopentyl | H | morpholine | -O-CH2-pyridazin-3-yl |
| 590 | H | Me | cyclopentyl | H | morpholine | -O-CH2-pyrazinyl |
| 591 | H | Me | cyclopentyl | H | morpholine | -O-CH2-pyridazin-3-yl N-oxide |
| 592 | H | Me | cyclopentyl | H | morpholine | -NH-CH2-pyridazin-3-yl |
| 593 | H | Me | cyclopentyl | H | morpholine | -O-CH2-furan-3-yl |
| 594 | H | Me | cyclopentyl | H | morpholine | -O-CH2-thiophen-3-yl |
| 595 | H | Me | cyclopentyl | H | morpholine | -O-CH2-imidazol-4-yl |
| 596 | H | Me | cyclopentyl | H | morpholine | -NH-CH2-furan-2-yl |
| 597 | H | Me | cyclopentyl | H | morpholine | -NH-CH2-thiophen-2-yl |
| 598 | H | Me | cyclopentyl | H | morpholine | -NH-CH2-pyrrol-2-yl |
| 599 | H | Me | cyclopentyl | H | morpholine | -NH-CH2-(1-methyl-pyrrol-2-yl) |
| 600 | H | Me | cyclopentyl | H | morpholine | -O-CH2-(1,3-dimethyl-pyrazol-5-yl) |
| 601 | H | Me | cyclopentyl | Me | H | H |

TABLE 1-continued

| Compound No | X | R1 | R2 | R3 | R4 | R5 |
|---|---|---|---|---|---|---|
| 602 | H | Me | cyclopentyl | Me | H | OMe |
| 603 | H | Me | cyclopentyl | Me | H | F |
| 604 | H | Me | cyclopentyl | Me | H | Cl |
| 605 | H | Me | cyclopentyl | Me | H | Br |
| 606 | H | Me | cyclopentyl | Me | H | I |
| 607 | H | Me | cyclopentyl | Me | H | 2-methoxypyridin-yl |
| 608 | H | Me | cyclopentyl | Me | H | 2-methoxypyridin-yl N-oxide |
| 609 | H | Me | cyclopentyl | Me | H | 3-methoxypyridin-yl |
| 610 | H | Me | cyclopentyl | Me | H | 3-methoxypyridin-yl N-oxide |
| 611 | H | Me | cyclopentyl | Me | H | 4-methoxypyridin-yl |
| 612 | H | Me | cyclopentyl | Me | H | 4-methoxypyridin-yl N-oxide |
| 613 | H | Me | cyclopentyl | Me | H | (pyridin-2-ylmethoxy) |
| 614 | H | Me | cyclopentyl | Me | H | (pyridin-2-ylmethoxy) N-oxide |

TABLE 1-continued

| Compound No | X | R1 | R2 | R3 | R4 | R5 |
|---|---|---|---|---|---|---|
| 615 | H | Me | cyclopentyl | Me | H | methoxymethyl-3-pyridinyl |
| 616 | H | Me | cyclopentyl | Me | H | methoxymethyl-3-pyridinyl N-oxide |
| 617 | H | Me | cyclopentyl | Me | H | methoxymethyl-4-pyridinyl |
| 618 | H | Me | cyclopentyl | Me | H | methoxymethyl-4-pyridinyl N-oxide |
| 619 | H | Me | cyclopentyl | Me | H | methoxyethyl-2-pyridinyl |
| 620 | H | Me | cyclopentyl | Me | H | methoxyethyl-2-pyridinyl N-oxide |
| 621 | H | Me | cyclopentyl | Me | H | methoxyethyl-3-pyridinyl |
| 622 | H | Me | cyclopentyl | Me | H | methoxyethyl-3-pyridinyl N-oxide |
| 623 | H | Me | cyclopentyl | Me | H | methoxyethyl-4-pyridinyl |
| 624 | H | Me | cyclopentyl | Me | H | methoxyethyl-4-pyridinyl N-oxide |
| 625 | H | Me | cyclopentyl | Me | H | methoxypropyl-2-pyridinyl |
| 626 | H | Me | cyclopentyl | Me | H | methoxypropyl-2-pyridinyl N-oxide |

TABLE 1-continued

| Compound No | X | R1 | R2 | R3 | R4 | R5 |
|---|---|---|---|---|---|---|
| 627 | H | Me | cyclopentyl | Me | H | 3-(3-pyridyl)propyl methyl ether |
| 628 | H | Me | cyclopentyl | Me | H | 3-(3-pyridyl N-oxide)propyl methyl ether |
| 629 | H | Me | cyclopentyl | Me | H | 3-(4-pyridyl)propyl methyl ether |
| 630 | H | Me | cyclopentyl | Me | H | 3-(4-pyridyl N-oxide)propyl methyl ether |
| 631 | H | Me | cyclopentyl | Me | H | N-methyl-2-phenylethylamine |
| 632 | H | Me | cyclopentyl | Me | H | N,N-dimethyl-2-phenylethylamine |
| 633 | H | Me | cyclopentyl | Me | H | N-methyl-2-(2-pyridyl)ethylamine |
| 634 | H | Me | cyclopentyl | Me | H | N,N-dimethyl-2-(2-pyridyl)ethylamine |
| 635 | H | Me | cyclopentyl | Me | H | N-methyl-2-(3-pyridyl)ethylamine |
| 636 | H | Me | cyclopentyl | Me | H | N,N-dimethyl-2-(3-pyridyl)ethylamine |
| 637 | H | Me | cyclopentyl | Me | H | N-methyl-2-(4-pyridyl)ethylamine |

TABLE 1-continued

| Compound No | X | R1 | R2 | R3 | R4 | R5 |
|---|---|---|---|---|---|---|
| 638 | H | Me | cyclopentyl | Me | H | CH2CH2-(4-pyridyl) with N(Me) |
| 639 | H | Me | cyclopentyl | Me | H | CH2O-pyridazin-3-yl |
| 640 | H | Me | cyclopentyl | Me | H | CH2O-pyrazin-2-yl |
| 641 | H | Me | cyclopentyl | Me | H | CH2O-pyrimidinyl N-oxide |
| 642 | H | Me | cyclopentyl | Me | H | CH2NH-pyridazin-3-yl |
| 643 | H | Me | cyclopentyl | Me | H | CH2O-furan-3-yl |
| 644 | H | Me | cyclopentyl | Me | H | CH2O-thiophen-3-yl |
| 645 | H | Me | cyclopentyl | Me | H | CH2O-imidazol-4-yl |
| 646 | H | Me | cyclopentyl | Me | H | CH2NH-furan-2-yl |
| 647 | H | Me | cyclopentyl | Me | H | CH2NH-thiophen-2-yl |
| 648 | H | Me | cyclopentyl | Me | H | CH2NH-pyrrol-2-yl |
| 649 | H | Me | cyclopentyl | Me | H | CH2NH-(1-methylpyrrol-2-yl) |
| 650 | H | Me | cyclopentyl | Me | H | CH2O-(1,3-dimethylpyrazol-5-yl) |

TABLE 1-continued
| Compound No | X | R1 | R2 | R3 | R4 | R5 |
|---|---|---|---|---|---|---|
| 651 | H | Me |  | Me | Me | H |
| 652 | H | Me |  | Me | Me | OMe |
| 653 | H | Me |  | Me | Me | F |
| 654 | H | Me |  | Me | Me | Cl |
| 655 | H | Me |  | Me | Me | Br |
| 656 | H | Me |  | Me | Me | I |
| 657 | H | Me |  | Me | Me | 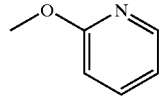 |
| 658 | H | Me |  | Me | Me | 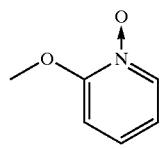 |
| 659 | H | Me |  | Me | Me | 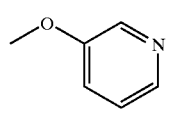 |
| 660 | H | Me |  | Me | Me | 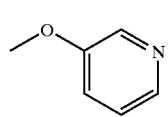 |
| 661 | H | Me |  | Me | Me | 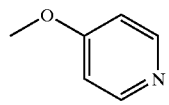 |
| 662 | H | Me |  | Me | Me | 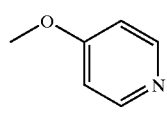 |
| 663 | H | Me |  | Me | Me | 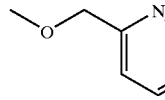 |

TABLE 1-continued

| Compound No | X | R1 | R2 | R3 | R4 | R5 |
|---|---|---|---|---|---|---|
| 664 | H | Me | cyclopentyl | Me | Me | methoxymethyl-2-pyridinyl N-oxide |
| 665 | H | Me | cyclopentyl | Me | Me | methoxymethyl-3-pyridinyl |
| 666 | H | Me | cyclopentyl | Me | Me | methoxymethyl-3-pyridinyl N-oxide |
| 667 | H | Me | cyclopentyl | Me | Me | methoxymethyl-4-pyridinyl |
| 668 | H | Me | cyclopentyl | Me | Me | methoxymethyl-4-pyridinyl N-oxide |
| 669 | H | Me | cyclopentyl | Me | Me | 2-methoxyethyl-2-pyridinyl |
| 670 | H | Me | cyclopentyl | Me | Me | 2-methoxyethyl-2-pyridinyl N-oxide |
| 671 | H | Me | cyclopentyl | Me | Me | 2-methoxyethyl-3-pyridinyl |
| 672 | H | Me | cyclopentyl | Me | Me | 2-methoxyethyl-3-pyridinyl N-oxide |
| 673 | H | Me | cyclopentyl | Me | Me | 2-methoxyethyl-4-pyridinyl |
| 674 | H | Me | cyclopentyl | Me | Me | 2-methoxyethyl-4-pyridinyl N-oxide |
| 675 | H | Me | cyclopentyl | Me | Me | 3-methoxypropyl-2-pyridinyl |

TABLE 1-continued
| Compound No | X | R1 | R2 | R3 | R4 | R5 |
|---|---|---|---|---|---|---|
| 676 | H | Me |  | Me | Me | 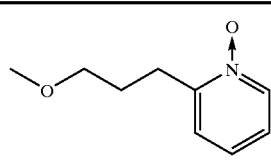 |
| 677 | H | Me |  | Me | Me | 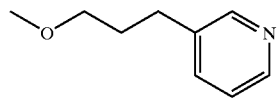 |
| 678 | H | Me |  | Me | Me | 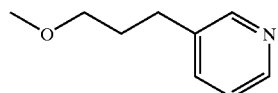 |
| 679 | H | Me |  | Me | Me | 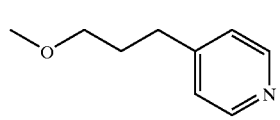 |
| 680 | H | Me |  | Me | Me | 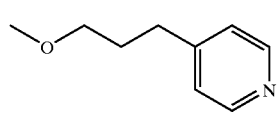 |
| 681 | H | Me |  | Me | Me | 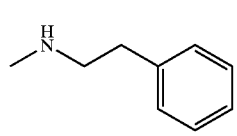 |
| 682 | H | Me |  | Me | Me | 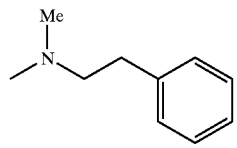 |
| 683 | H | Me |  | Me | Me | 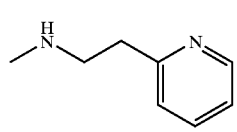 |
| 684 | H | Me |  | Me | Me | 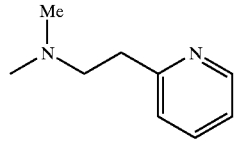 |
| 685 | H | Me |  | Me | Me | 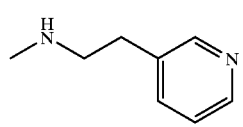 |
| 686 | H | Me |  | Me | Me | 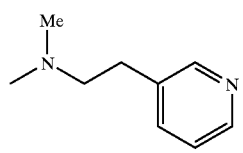 |

TABLE 1-continued

| Compound No | X | R1 | R2 | R3 | R4 | R5 |
|---|---|---|---|---|---|---|
| 687 | H | Me | cyclopentyl | Me | Me | -NH-CH2-CH2-(4-pyridyl) |
| 688 | H | Me | cyclopentyl | Me | Me | -N(Me)-CH2-CH2-(4-pyridyl) |
| 689 | H | Me | cyclopentyl | Me | Me | -O-CH2-(pyridazin-3-yl) |
| 690 | H | Me | cyclopentyl | Me | Me | -O-CH2-(pyrazin-2-yl) |
| 691 | H | Me | cyclopentyl | Me | Me | -O-CH2-(pyrazin-2-yl N-oxide) |
| 692 | H | Me | cyclopentyl | Me | Me | -NH-CH2-(pyridazin-3-yl) |
| 693 | H | Me | cyclopentyl | Me | Me | -O-CH2-(furan-3-yl) |
| 694 | H | Me | cyclopentyl | Me | Me | -O-CH2-(thiophen-3-yl) |
| 695 | H | Me | cyclopentyl | Me | Me | -O-CH2-(imidazol-4-yl) |
| 696 | H | Me | cyclopentyl | Me | Me | -NH-CH2-(furan-2-yl) |
| 697 | H | Me | cyclopentyl | Me | Me | -NH-CH2-(thiophen-2-yl) |
| 698 | H | Me | cyclopentyl | Me | Me | -NH-CH2-(pyrrol-2-yl) |
| 699 | H | Me | cyclopentyl | Me | Me | -NH-CH2-(1-methyl-pyrrol-2-yl) |

TABLE 1-continued
| Compound No | X | R1 | R2 | R3 | R4 | R5 |
|---|---|---|---|---|---|---|
| 700 | H | Me |  | Me | Me | 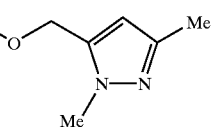 |
| 701 | H | Me |  | Me | Et | H |
| 702 | H | Me |  | Me | Et | OMe |
| 703 | H | Me |  | Me | Et | F |
| 704 | H | Me |  | Me | Et | Cl |
| 705 | H | Me |  | Me | Et | Br |
| 706 | H | Me |  | Me | Et | I |
| 707 | H | Me |  | Me | Et | 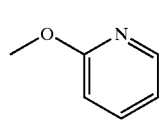 |
| 708 | H | Me |  | Me | Et | 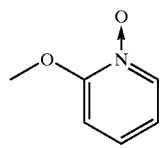 |
| 709 | H | Me |  | Me | Et | 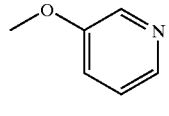 |
| 710 | H | Me |  | Me | Et | 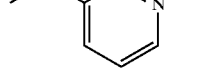 |
| 711 | H | Me |  | Me | Et | 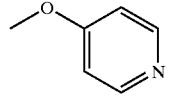 |
| 712 | H | Me |  | Me | Et | 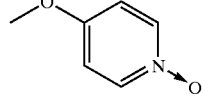 |

TABLE 1-continued
| Compound No | X | R1 | R2 | R3 | R4 | R5 |
|---|---|---|---|---|---|---|
| 713 | H | Me |  | Me | Et | 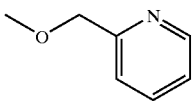 |
| 714 | H | Me |  | Me | Et | 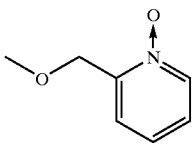 |
| 715 | H | Me |  | Me | Et | 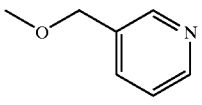 |
| 716 | H | Me |  | Me | Et | 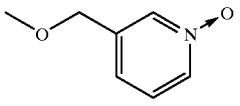 |
| 717 | H | Me |  | Me | Et | 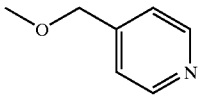 |
| 718 | H | Me |  | Me | Et | 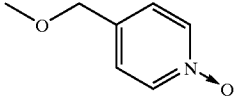 |
| 719 | H | Me |  | Me | Et | 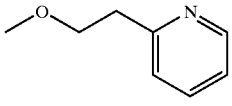 |
| 720 | H | Me |  | Me | Et | 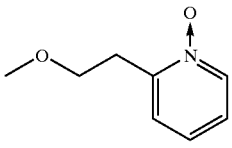 |
| 721 | H | Me |  | Me | Et | 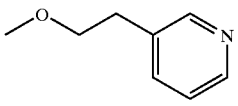 |
| 722 | H | Me |  | Me | Et | 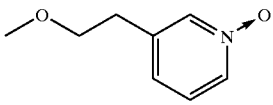 |
| 723 | H | Me |  | Me | Et | 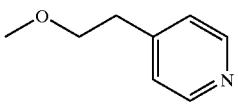 |
| 724 | H | Me |  | Me | Et | 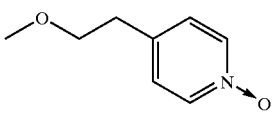 |

TABLE 1-continued

| Compound No | X | R1 | R2 | R3 | R4 | R5 |
|---|---|---|---|---|---|---|
| 725 | H | Me | cyclopentyl | Me | Et | 3-(2-pyridyl)propyl methyl ether |
| 726 | H | Me | cyclopentyl | Me | Et | 3-(2-pyridyl N-oxide)propyl methyl ether |
| 727 | H | Me | cyclopentyl | Me | Et | 3-(3-pyridyl)propyl methyl ether |
| 728 | H | Me | cyclopentyl | Me | Et | 3-(3-pyridyl N-oxide)propyl methyl ether |
| 729 | H | Me | cyclopentyl | Me | Et | 3-(4-pyridyl)propyl methyl ether |
| 730 | H | Me | cyclopentyl | Me | Et | 3-(4-pyridyl N-oxide)propyl methyl ether |
| 731 | H | Me | cyclopentyl | Me | Et | N-methyl-2-phenylethylamine |
| 732 | H | Me | cyclopentyl | Me | Et | N,N-dimethyl-2-phenylethylamine |
| 733 | H | Me | cyclopentyl | Me | Et | N-methyl-2-(2-pyridyl)ethylamine |
| 734 | H | Me | cyclopentyl | Me | Et | N,N-dimethyl-2-(2-pyridyl)ethylamine |
| 735 | H | Me | cyclopentyl | Me | Et | N-methyl-2-(3-pyridyl)ethylamine |

TABLE 1-continued

| Compound No | X | R1 | R2 | R3 | R4 | R5 |
|---|---|---|---|---|---|---|
| 736 | H | Me | cyclopentyl | Me | Et | CH₂CH₂-(pyridin-3-yl) with N(Me) |
| 737 | H | Me | cyclopentyl | Me | Et | NH-CH₂CH₂-(pyridin-4-yl) |
| 738 | H | Me | cyclopentyl | Me | Et | N(Me)-CH₂CH₂-(pyridin-4-yl) |
| 739 | H | Me | cyclopentyl | Me | Et | OCH₂-(pyridazin-3-yl) |
| 740 | H | Me | cyclopentyl | Me | Et | OCH₂-(pyrazin-2-yl) |
| 741 | H | Me | cyclopentyl | Me | Et | OCH₂-(pyrimidin-4-yl N-oxide) |
| 742 | H | Me | cyclopentyl | Me | Et | NH-CH₂-(pyridazin-3-yl) |
| 743 | H | Me | cyclopentyl | Me | Et | OCH₂-(furan-3-yl) |
| 744 | H | Me | cyclopentyl | Me | Et | OCH₂-(thiophen-3-yl) |
| 745 | H | Me | cyclopentyl | Me | Et | OCH₂-(imidazol-4-yl) |
| 746 | H | Me | cyclopentyl | Me | Et | NH-CH₂-(furan-2-yl) |
| 747 | H | Me | cyclopentyl | Me | Et | NH-CH₂-(thiophen-2-yl) |
| 748 | H | Me | cyclopentyl | Me | Et | NH-CH₂-(pyrrol-2-yl) |

TABLE 1-continued
| Compound No | X | R1 | R2 | R3 | R4 | R5 |
|---|---|---|---|---|---|---|
| 749 | H | Me |  | Me | Et | 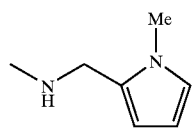 |
| 750 | H | Me |  | Me | Et | 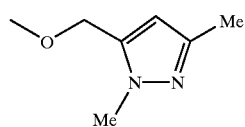 |
| 751 | H | Me |  | Me | OMe | H |
| 752 | H | Me |  | Me | OMe | OMe |
| 753 | H | Me |  | Me | OMe | F |
| 754 | H | Me |  | Me | OMe | Cl |
| 755 | H | Me |  | Me | OMe | Br |
| 756 | H | Me |  | Me | OMe | I |
| 757 | H | Me |  | Me | OMe | 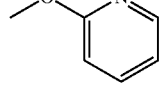 |
| 758 | H | Me |  | Me | OMe | 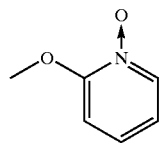 |
| 759 | H | Me |  | Me | OMe | 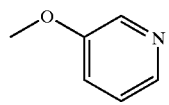 |
| 760 | H | Me |  | Me | OMe | 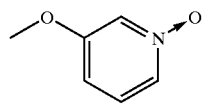 |
| 761 | H | Me |  | Me | OMe | 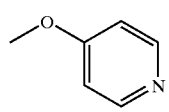 |

TABLE 1-continued

| Compound No | X | R1 | R2 | R3 | R4 | R5 |
|---|---|---|---|---|---|---|
| 762 | H | Me | cyclopentyl | Me | OMe | 4-methoxypyridine N-oxide-methoxy |
| 763 | H | Me | cyclopentyl | Me | OMe | 2-(methoxymethyl)pyridine |
| 764 | H | Me | cyclopentyl | Me | OMe | 2-(methoxymethyl)pyridine N-oxide |
| 765 | H | Me | cyclopentyl | Me | OMe | 3-(methoxymethyl)pyridine |
| 766 | H | Me | cyclopentyl | Me | OMe | 3-(methoxymethyl)pyridine N-oxide |
| 767 | H | Me | cyclopentyl | Me | OMe | 4-(methoxymethyl)pyridine |
| 768 | H | Me | cyclopentyl | Me | OMe | 4-(methoxymethyl)pyridine N-oxide |
| 769 | H | Me | cyclopentyl | Me | OMe | 2-(2-methoxyethyl)pyridine |
| 770 | H | Me | cyclopentyl | Me | OMe | 2-(2-methoxyethyl)pyridine N-oxide |
| 771 | H | Me | cyclopentyl | Me | OMe | 3-(2-methoxyethyl)pyridine |
| 772 | H | Me | cyclopentyl | Me | OMe | 3-(2-methoxyethyl)pyridine N-oxide |
| 773 | H | Me | cyclopentyl | Me | OMe | 4-(2-methoxyethyl)pyridine |

TABLE 1-continued

| Compound No | X | R1 | R2 | R3 | R4 | R5 |
|---|---|---|---|---|---|---|
| 774 | H | Me | cyclopentyl | Me | OMe | 2-(4-pyridyl N-oxide)ethyl methyl ether |
| 775 | H | Me | cyclopentyl | Me | OMe | 3-(2-pyridyl)propyl methyl ether |
| 776 | H | Me | cyclopentyl | Me | OMe | 3-(2-pyridyl N-oxide)propyl methyl ether |
| 777 | H | Me | cyclopentyl | Me | OMe | 3-(3-pyridyl)propyl methyl ether |
| 778 | H | Me | cyclopentyl | Me | OMe | 3-(3-pyridyl N-oxide)propyl methyl ether |
| 779 | H | Me | cyclopentyl | Me | OMe | 3-(4-pyridyl)propyl methyl ether |
| 780 | H | Me | cyclopentyl | Me | OMe | 3-(4-pyridyl N-oxide)propyl methyl ether |
| 781 | H | Me | cyclopentyl | Me | OMe | N-methyl-2-phenylethylamine |
| 782 | H | Me | cyclopentyl | Me | OMe | N,N-dimethyl-2-phenylethylamine |
| 783 | H | Me | cyclopentyl | Me | OMe | N-methyl-2-(2-pyridyl)ethylamine |
| 784 | H | Me | cyclopentyl | Me | OMe | N,N-dimethyl-2-(2-pyridyl)ethylamine |

TABLE 1-continued

| Compound No | X | R1 | R2 | R3 | R4 | R5 |
|---|---|---|---|---|---|---|
| 785 | H | Me | cyclopentyl | Me | OMe | -NH(Me)-CH2CH2-(pyridin-3-yl) |
| 786 | H | Me | cyclopentyl | Me | OMe | -N(Me)2-CH2CH2-(pyridin-3-yl) |
| 787 | H | Me | cyclopentyl | Me | OMe | -NH(Me)-CH2CH2-(pyridin-4-yl) |
| 788 | H | Me | cyclopentyl | Me | OMe | -N(Me)2-CH2CH2-(pyridin-4-yl) |
| 789 | H | Me | cyclopentyl | Me | OMe | -O-CH2-(pyridazin-3-yl) |
| 790 | H | Me | cyclopentyl | Me | OMe | -O-CH2-(pyrazin-2-yl) |
| 791 | H | Me | cyclopentyl | Me | OMe | -O-CH2-(pyrazin-2-yl N-oxide) |
| 792 | H | Me | cyclopentyl | Me | OMe | -NH-CH2-(pyridazin-3-yl) |
| 793 | H | Me | cyclopentyl | Me | OMe | -O-CH2-(furan-3-yl) |
| 794 | H | Me | cyclopentyl | Me | OMe | -O-CH2-(thiophen-3-yl) |
| 795 | H | Me | cyclopentyl | Me | OMe | -O-CH2-(imidazol-4-yl) |
| 796 | H | Me | cyclopentyl | Me | OMe | -NH-CH2-(furan-2-yl) |
| 797 | H | Me | cyclopentyl | Me | OMe | -NH-CH2-(thiophen-2-yl) |

TABLE 1-continued

| Compound No | X | R1 | R2 | R3 | R4 | R5 |
|---|---|---|---|---|---|---|
| 798 | H | Me | cyclopentyl | Me | OMe | CH2-NH-(1H-pyrrol-2-yl) |
| 799 | H | Me | cyclopentyl | Me | OMe | CH2-NH-(1-methyl-pyrrol-2-yl) |
| 800 | H | Me | cyclopentyl | Me | OMe | 5-(methoxymethyl)-1,3-dimethyl-pyrazole |
| 801 | H | Me | cyclopentyl | Me | NH2 | H |
| 802 | H | Me | cyclopentyl | Me | NH2 | OMe |
| 803 | H | Me | cyclopentyl | Me | NH2 | F |
| 804 | H | Me | cyclopentyl | Me | NH2 | Cl |
| 805 | H | Me | cyclopentyl | Me | NH2 | Br |
| 806 | H | Me | cyclopentyl | Me | NH2 | I |
| 807 | H | Me | cyclopentyl | Me | NH2 | 2-methoxypyridin-3-yl |
| 808 | H | Me | cyclopentyl | Me | NH2 | 2-methoxypyridin-3-yl N-oxide |
| 809 | H | Me | cyclopentyl | Me | NH2 | 3-methoxypyridin-5-yl |
| 810 | H | Me | cyclopentyl | Me | NH2 | 3-methoxypyridin-5-yl N-oxide |

TABLE 1-continued
| Compound No | X | R1 | R2 | R3 | R4 | R5 |
|---|---|---|---|---|---|---|
| 811 | H | Me |  | Me | NH$_2$ | 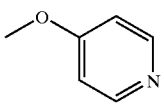 |
| 812 | H | Me |  | Me | NH$_2$ | 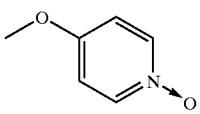 |
| 813 | H | Me |  | Me | NH$_2$ | 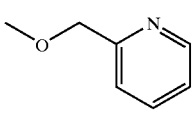 |
| 814 | H | Me |  | Me | NH$_2$ | 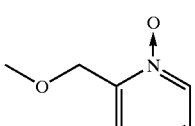 |
| 815 | H | Me |  | Me | NH$_2$ | 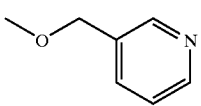 |
| 816 | H | Me |  | Me | NH$_2$ | 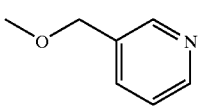 |
| 817 | H | Me |  | Me | NH$_2$ | 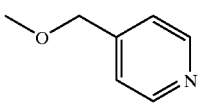 |
| 818 | H | Me |  | Me | NH$_2$ | 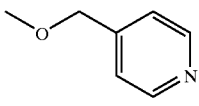 |
| 819 | H | Me |  | Me | NH$_2$ | 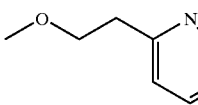 |
| 820 | H | Me |  | Me | NH$_2$ | 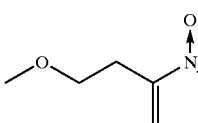 |
| 821 | H | Me |  | Me | NH$_2$ | 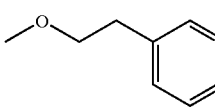 |
| 822 | H | Me |  | Me | NH$_2$ | 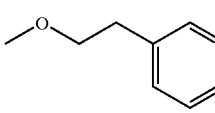 |

TABLE 1-continued

| Compound No | X | R1 | R2 | R3 | R4 | R5 |
|---|---|---|---|---|---|---|
| 823 | H | Me | cyclopentyl | Me | NH$_2$ | methoxyethyl-pyridin-4-yl |
| 824 | H | Me | cyclopentyl | Me | NH$_2$ | methoxyethyl-pyridin-4-yl N-oxide |
| 825 | H | Me | cyclopentyl | Me | NH$_2$ | methoxypropyl-pyridin-2-yl |
| 826 | H | Me | cyclopentyl | Me | NH$_2$ | methoxypropyl-pyridin-2-yl N-oxide |
| 827 | H | Me | cyclopentyl | Me | NH$_2$ | methoxypropyl-pyridin-3-yl |
| 828 | H | Me | cyclopentyl | Me | NH$_2$ | methoxypropyl-pyridin-3-yl N-oxide |
| 829 | H | Me | cyclopentyl | Me | NH$_2$ | methoxypropyl-pyridin-4-yl |
| 830 | H | Me | cyclopentyl | Me | NH$_2$ | methoxypropyl-pyridin-4-yl N-oxide |
| 831 | H | Me | cyclopentyl | Me | NH$_2$ | N-methyl-phenethylamine |
| 832 | H | Me | cyclopentyl | Me | NH$_2$ | N,N-dimethyl-phenethylamine |
| 833 | H | Me | cyclopentyl | Me | NH$_2$ | N-methyl-2-(pyridin-2-yl)ethylamine |

TABLE 1-continued

| Compound No | X | R1 | R2 | R3 | R4 | R5 |
|---|---|---|---|---|---|---|
| 834 | H | Me | cyclopentyl | Me | NH₂ | N(Me)CH₂CH₂-(pyridin-2-yl) |
| 835 | H | Me | cyclopentyl | Me | NH₂ | NH-CH₂CH₂-(pyridin-3-yl) |
| 836 | H | Me | cyclopentyl | Me | NH₂ | N(Me)CH₂CH₂-(pyridin-3-yl) |
| 837 | H | Me | cyclopentyl | Me | NH₂ | NH-CH₂CH₂-(pyridin-4-yl) |
| 838 | H | Me | cyclopentyl | Me | NH₂ | N(Me)CH₂CH₂-(pyridin-4-yl) |
| 839 | H | Me | cyclopentyl | Me | NH₂ | O-CH₂-(pyridazin-3-yl) |
| 840 | H | Me | cyclopentyl | Me | NH₂ | O-CH₂-(pyrazin-2-yl) |
| 841 | H | Me | cyclopentyl | Me | NH₂ | O-CH₂-(pyrimidin-4-yl N-oxide) |
| 842 | H | Me | cyclopentyl | Me | NH₂ | NH-CH₂-(pyridazin-3-yl) |
| 843 | H | Me | cyclopentyl | Me | NH₂ | O-CH₂-(furan-3-yl) |
| 844 | H | Me | cyclopentyl | Me | NH₂ | O-CH₂-(thiophen-3-yl) |
| 845 | H | Me | cyclopentyl | Me | NH₂ | O-CH₂-(1H-imidazol-4-yl) |

TABLE 1-continued
| Compound No | X | R1 | R2 | R3 | R4 | R5 |
|---|---|---|---|---|---|---|
| 846 | H | Me |  | Me | NH₂ | 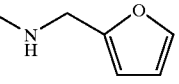 |
| 847 | H | Me |  | Me | NH₂ | 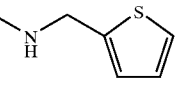 |
| 848 | H | Me |  | Me | NH₂ | 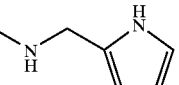 |
| 849 | H | Me |  | Me | NH₂ | 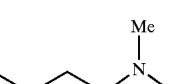 |
| 850 | H | Me |  | Me | NH₂ | 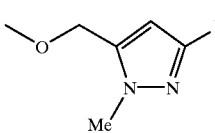 |
| 851 | H | Me |  | Me | NHMe | H |
| 852 | H | Me |  | Me | NHMe | OMe |
| 853 | H | Me |  | Me | NHMe | F |
| 854 | H | Me |  | Me | NHMe | Cl |
| 855 | H | Me |  | Me | NHMe | Br |
| 856 | H | Me |  | Me | NHMe | I |
| 857 | H | Me |  | Me | NHMe | 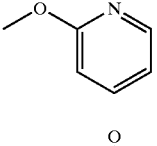 |
| 858 | H | Me |  | Me | NHMe | 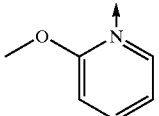 |
| 859 | H | Me |  | Me | NHMe | 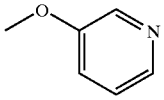 |

TABLE 1-continued

| Compound No | X | R1 | R2 | R3 | R4 | R5 |
|---|---|---|---|---|---|---|
| 860 | H | Me | cyclopentyl | Me | NHMe | 3-methoxypyridine N-oxide |
| 861 | H | Me | cyclopentyl | Me | NHMe | 4-methoxypyridine |
| 862 | H | Me | cyclopentyl | Me | NHMe | 4-methoxypyridine N-oxide |
| 863 | H | Me | cyclopentyl | Me | NHMe | 2-(methoxymethyl)pyridine |
| 864 | H | Me | cyclopentyl | Me | NHMe | 2-(methoxymethyl)pyridine N-oxide |
| 865 | H | Me | cyclopentyl | Me | NHMe | 3-(methoxymethyl)pyridine |
| 866 | H | Me | cyclopentyl | Me | NHMe | 3-(methoxymethyl)pyridine N-oxide |
| 867 | H | Me | cyclopentyl | Me | NHMe | 4-(methoxymethyl)pyridine |
| 868 | H | Me | cyclopentyl | Me | NHMe | 4-(methoxymethyl)pyridine N-oxide |
| 869 | H | Me | cyclopentyl | Me | NHMe | 2-(2-methoxyethyl)pyridine |
| 870 | H | Me | cyclopentyl | Me | NHMe | 2-(2-methoxyethyl)pyridine N-oxide |
| 871 | H | Me | cyclopentyl | Me | NHMe | 3-(2-methoxyethyl)pyridine |

TABLE 1-continued
| Compound No | X | R1 | R2 | R3 | R4 | R5 |
|---|---|---|---|---|---|---|
| 872 | H | Me |  | Me | NHMe | 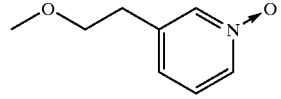 |
| 873 | H | Me |  | Me | NHMe | 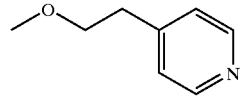 |
| 874 | H | Me |  | Me | NHMe | 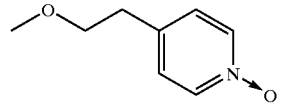 |
| 875 | H | Me |  | Me | NHMe | 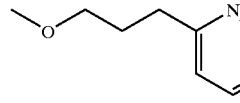 |
| 876 | H | Me |  | Me | NHMe | 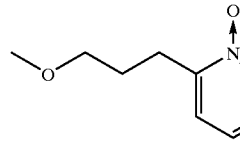 |
| 877 | H | Me |  | Me | NHMe | 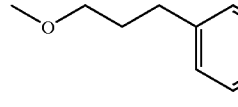 |
| 878 | H | Me |  | Me | NHMe | 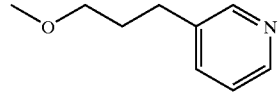 |
| 879 | H | Me |  | Me | NHMe | 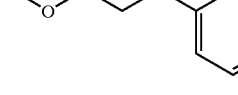 |
| 880 | H | Me |  | Me | NHMe | 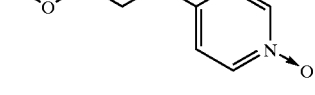 |
| 881 | H | Me |  | Me | NHMe | 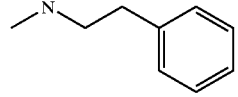 |
| 882 | H | Me |  | Me | NHMe | 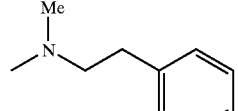 |
| 883 | H | Me |  | Me | NHMe | 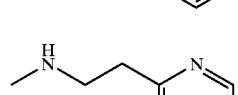 |

TABLE 1-continued

| Compound No | X | R1 | R2 | R3 | R4 | R5 |
|---|---|---|---|---|---|---|
| 884 | H | Me | cyclopentyl | Me | NHMe | -N(Me)CH2CH2-(pyridin-2-yl) |
| 885 | H | Me | cyclopentyl | Me | NHMe | -NH-CH2CH2-(pyridin-3-yl) |
| 886 | H | Me | cyclopentyl | Me | NHMe | -N(Me)CH2CH2-(pyridin-3-yl) |
| 887 | H | Me | cyclopentyl | Me | NHMe | -NH-CH2CH2-(pyridin-4-yl) |
| 888 | H | Me | cyclopentyl | Me | NHMe | -N(Me)CH2CH2-(pyridin-4-yl) |
| 889 | H | Me | cyclopentyl | Me | NHMe | -OCH2-(pyridazin-3-yl) |
| 890 | H | Me | cyclopentyl | Me | NHMe | -OCH2-(pyrazin-2-yl) |
| 891 | H | Me | cyclopentyl | Me | NHMe | -OCH2-(pyrimidin-4-yl N-oxide) |
| 892 | H | Me | cyclopentyl | Me | NHMe | -NH-CH2-(pyridazin-3-yl) |
| 893 | H | Me | cyclopentyl | Me | NHMe | -OCH2-(furan-3-yl) |
| 894 | H | Me | cyclopentyl | Me | NHMe | -OCH2-(thiophen-3-yl) |
| 895 | H | Me | cyclopentyl | Me | NHMe | -OCH2-(1H-imidazol-4-yl) |

TABLE 1-continued
| Compound No | X | R1 | R2 | R3 | R4 | R5 |
|---|---|---|---|---|---|---|
| 896 | H | Me |  | Me | NHMe | 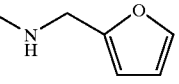 |
| 897 | H | Me |  | Me | NHMe | 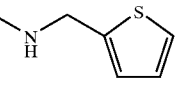 |
| 898 | H | Me |  | Me | NHMe | 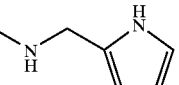 |
| 899 | H | Me |  | Me | NHMe | 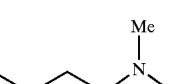 |
| 900 | H | Me |  | Me | NHMe | 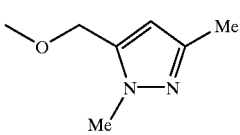 |
| 901 | H | Me |  | Me | NHEt | H |
| 902 | H | Me |  | Me | NHEt | OMe |
| 903 | H | Me |  | Me | NHEt | F |
| 904 | H | Me |  | Me | NHEt | Cl |
| 905 | H | Me |  | Me | NHEt | Br |
| 906 | H | Me |  | Me | NHEt | I |
| 907 | H | Me |  | Me | NHEt | 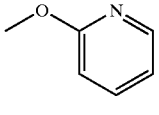 |
| 908 | H | Me |  | Me | NHEt | 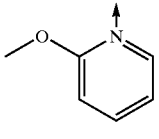 |
| 909 | H | Me |  | Me | NHEt | 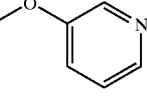 |

TABLE 1-continued
| Compound No | X | R1 | R2 | R3 | R4 | R5 |
|---|---|---|---|---|---|---|
| 910 | H | Me |  | Me | NHEt | 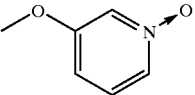 |
| 911 | H | Me |  | Me | NHEt | 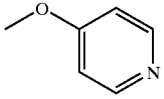 |
| 912 | H | Me |  | Me | NHEt | 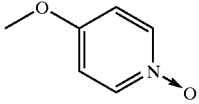 |
| 913 | H | Me |  | Me | NHEt | 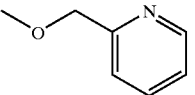 |
| 914 | H | Me |  | Me | NHEt | 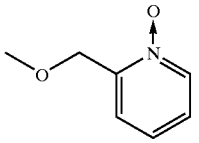 |
| 915 | H | Me |  | Me | NHEt | 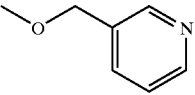 |
| 916 | H | Me |  | Me | NHEt | 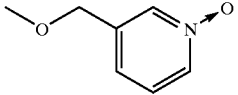 |
| 917 | H | Me |  | Me | NHEt | 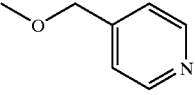 |
| 918 | H | Me |  | Me | NHEt | 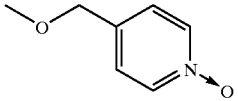 |
| 919 | H | Me |  | Me | NHEt | 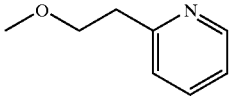 |
| 920 | H | Me |  | Me | NHEt | 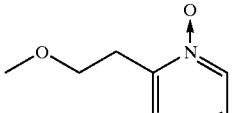 |
| 921 | H | Me |  | Me | NHEt | 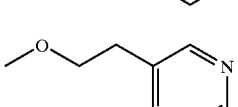 |

TABLE 1-continued
| Compound No | X | R1 | R2 | R3 | R4 | R5 |
|---|---|---|---|---|---|---|
| 922 | H | Me |  | Me | NHEt | 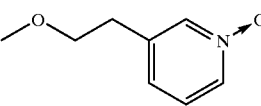 |
| 923 | H | Me |  | Me | NHEt | 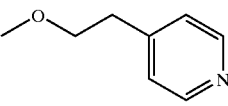 |
| 924 | H | Me |  | Me | NHEt | 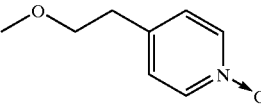 |
| 925 | H | Me |  | Me | NHEt | 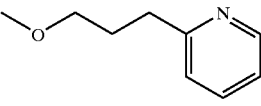 |
| 926 | H | Me |  | Me | NHEt | 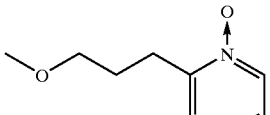 |
| 927 | H | Me |  | Me | NHEt | 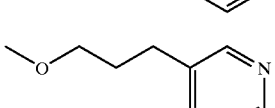 |
| 928 | H | Me |  | Me | NHEt | 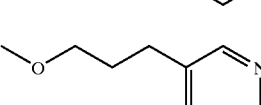 |
| 929 | H | Me |  | Me | NHEt | 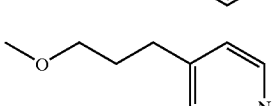 |
| 930 | H | Me |  | Me | NHEt | 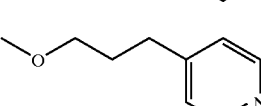 |
| 931 | H | Me |  | Me | NHEt | 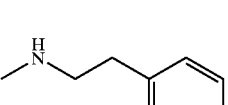 |
| 932 | H | Me |  | Me | NHEt | 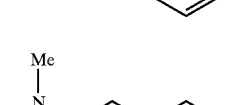 |
| 933 | H | Me |  | Me | NHEt | 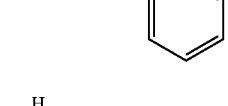 |

TABLE 1-continued
| Compound No | X | R1 | R2 | R3 | R4 | R5 |
|---|---|---|---|---|---|---|
| 934 | H | Me |  | Me | NHEt | 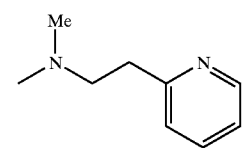 |
| 935 | H | Me |  | Me | NHEt | 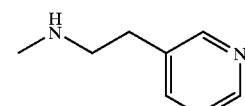 |
| 936 | H | Me |  | Me | NHEt | 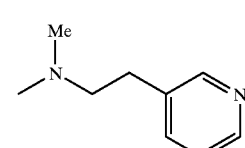 |
| 937 | H | Me |  | Me | NHEt | 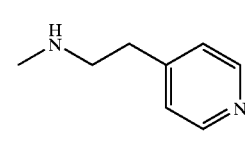 |
| 938 | H | Me |  | Me | NHEt | 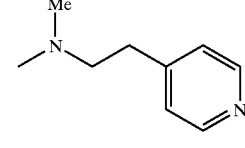 |
| 939 | H | Me |  | Me | NHEt | 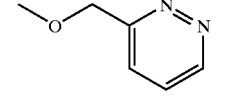 |
| 940 | H | Me |  | Me | NHEt | 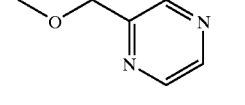 |
| 941 | H | Me |  | Me | NHEt | 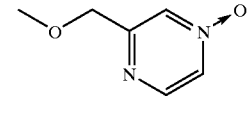 |
| 942 | H | Me |  | Me | NHEt | 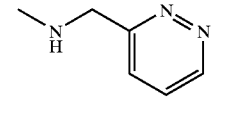 |
| 943 | H | Me |  | Me | NHEt | 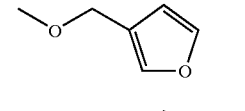 |
| 944 | H | Me |  | Me | NHEt | 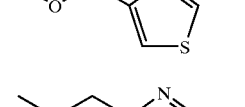 |
| 945 | H | Me |  | Me | NHEt | 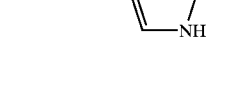 |

TABLE 1-continued
| Compound No | X | R1 | R2 | R3 | R4 | R5 |
|---|---|---|---|---|---|---|
| 946 | H | Me |  | Me | NHEt | 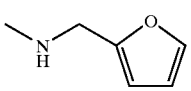 |
| 947 | H | Me |  | Me | NHEt | 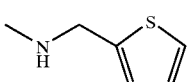 |
| 948 | H | Me |  | Me | NHEt | 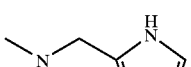 |
| 949 | H | Me |  | Me | NHEt |  |
| 950 | H | Me |  | Me | NHEt |  |
| 951 | H | Me |  | Me | NHn-Pr | H |
| 952 | H | Me |  | Me | NHn-Pr | OMe |
| 953 | H | Me |  | Me | NHn-Pr | F |
| 954 | H | Me |  | Me | NHn-Pr | Cl |
| 955 | H | Me |  | Me | NHn-Pr | Br |
| 956 | H | Me |  | Me | NHn-Pr | I |
| 957 | H | Me |  | Me | NHn-Pr |  |
| 958 | H | Me |  | Me | NHn-Pr | 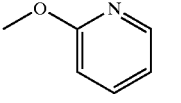 |
| 959 | H | Me |  | Me | NHn-Pr | 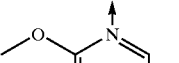 |

TABLE 1-continued

| Compound No | X | R1 | R2 | R3 | R4 | R5 |
|---|---|---|---|---|---|---|
| 960 | H | Me | cyclopentyl | Me | NHn-Pr | 3-methoxypyridine N-oxide |
| 961 | H | Me | cyclopentyl | Me | NHn-Pr | 4-methoxypyridine |
| 962 | H | Me | cyclopentyl | Me | NHn-Pr | 4-methoxypyridine N-oxide |
| 963 | H | Me | cyclopentyl | Me | NHn-Pr | 2-(methoxymethyl)pyridine |
| 964 | H | Me | cyclopentyl | Me | NHn-Pr | 2-(methoxymethyl)pyridine N-oxide |
| 965 | H | Me | cyclopentyl | Me | NHn-Pr | 3-(methoxymethyl)pyridine |
| 966 | H | Me | cyclopentyl | Me | NHn-Pr | 3-(methoxymethyl)pyridine N-oxide |
| 967 | H | Me | cyclopentyl | Me | NHn-Pr | 4-(methoxymethyl)pyridine |
| 968 | H | Me | cyclopentyl | Me | NHn-Pr | 4-(methoxymethyl)pyridine N-oxide |
| 969 | H | Me | cyclopentyl | Me | NHn-Pr | 2-(2-methoxyethyl)pyridine |
| 970 | H | Me | cyclopentyl | Me | NHn-Pr | 2-(2-methoxyethyl)pyridine N-oxide |
| 971 | H | Me | cyclopentyl | Me | NHn-Pr | 3-(2-methoxyethyl)pyridine |

TABLE 1-continued
| Compound No | X | R1 | R2 | R3 | R4 | R5 |
|---|---|---|---|---|---|---|
| 972 | H | Me |  | Me | NHn-Pr | 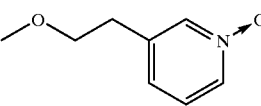 |
| 973 | H | Me |  | Me | NHn-Pr | 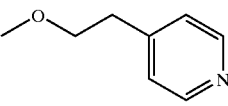 |
| 974 | H | Me |  | Me | NHn-Pr | 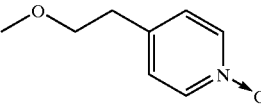 |
| 975 | H | Me |  | Me | NHn-Pr | 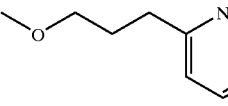 |
| 976 | H | Me |  | Me | NHn-Pr | 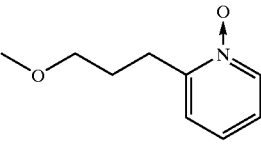 |
| 977 | H | Me |  | Me | NHn-Pr | 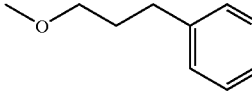 |
| 978 | H | Me |  | Me | NHn-Pr | 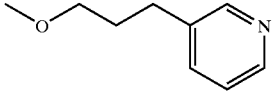 |
| 979 | H | Me |  | Me | NHn-Pr | 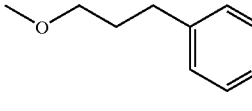 |
| 980 | H | Me |  | Me | NHn-Pr | 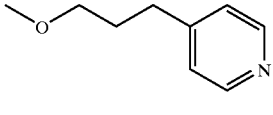 |
| 981 | H | Me |  | Me | NHn-Pr | 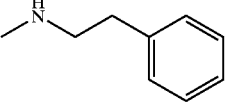 |
| 982 | H | Me |  | Me | NHn-Pr | 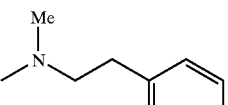 |
| 983 | H | Me |  | Me | NHn-Pr | 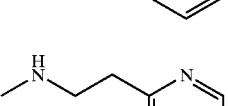 |

TABLE 1-continued
| Compound No | X | R1 | R2 | R3 | R4 | R5 |
|---|---|---|---|---|---|---|
| 984 | H | Me |  | Me | NHn-Pr | 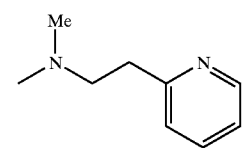 |
| 985 | H | Me |  | Me | NHn-Pr | 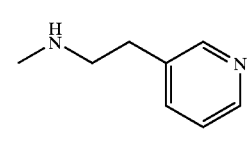 |
| 986 | H | Me |  | Me | NHn-Pr | 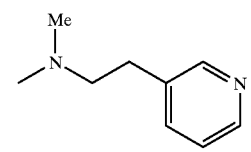 |
| 987 | H | Me |  | Me | NHn-Pr | 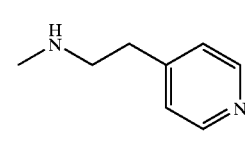 |
| 988 | H | Me |  | Me | NHn-Pr | 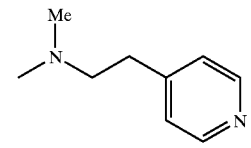 |
| 989 | H | Me |  | Me | NHn-Pr | 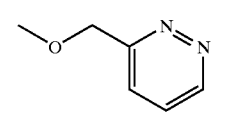 |
| 990 | H | Me |  | Me | NHn-Pr | 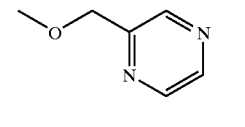 |
| 991 | H | Me |  | Me | NHn-Pr | 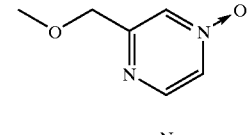 |
| 992 | H | Me |  | Me | NHn-Pr | 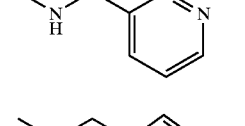 |
| 993 | H | Me |  | Me | NHn-Pr | 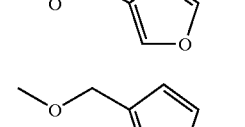 |
| 994 | H | Me |  | Me | NHn-Pr | 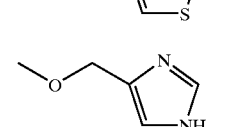 |
| 995 | H | Me |  | Me | NHn-Pr | 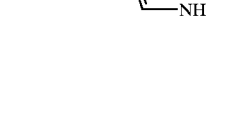 |

TABLE 1-continued
| Compound No | X | R1 | R2 | R3 | R4 | R5 |
|---|---|---|---|---|---|---|
| 996 | H | Me |  | Me | NHn-Pr | 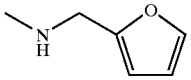 |
| 997 | H | Me |  | Me | NHn-Pr | 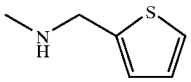 |
| 998 | H | Me |  | Me | NHn-Pr | 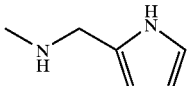 |
| 999 | H | Me |  | Me | NHn-Pr |  |
| 1000 | H | Me |  | Me | NHn-Pr |  |
| 1001 | H | Me |  | Me | NMe$_2$ | H |
| 1002 | H | Me |  | Me | NMe$_2$ | OMe |
| 1003 | H | Me |  | Me | NMe$_2$ | F |
| 1004 | H | Me |  | Me | NMe$_2$ | Cl |
| 1005 | H | Me |  | Me | NMe$_2$ | Br |
| 1006 | H | Me |  | Me | NMe$_2$ | I |
| 1007 | H | Me |  | Me | NMe$_2$ | 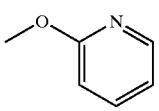 |
| 1008 | H | Me |  | Me | NMe$_2$ | 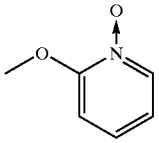 |
| 1009 | H | Me |  | Me | NMe$_2$ | 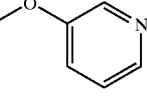 |

TABLE 1-continued

| Compound No | X | R1 | R2 | R3 | R4 | R5 |
|---|---|---|---|---|---|---|
| 1010 | H | Me | cyclopentyl | Me | NMe₂ | 3-methoxy pyridine N-oxide |
| 1011 | H | Me | cyclopentyl | Me | NMe₂ | 4-methoxy pyridine |
| 1012 | H | Me | cyclopentyl | Me | NMe₂ | 4-methoxy pyridine N-oxide |
| 1013 | H | Me | cyclopentyl | Me | NMe₂ | 2-(methoxymethyl) pyridine |
| 1014 | H | Me | cyclopentyl | Me | NMe₂ | 2-(methoxymethyl) pyridine N-oxide |
| 1015 | H | Me | cyclopentyl | Me | NMe₂ | 3-(methoxymethyl) pyridine |
| 1016 | H | Me | cyclopentyl | Me | NMe₂ | 3-(methoxymethyl) pyridine N-oxide |
| 1017 | H | Me | cyclopentyl | Me | NMe₂ | 4-(methoxymethyl) pyridine |
| 1018 | H | Me | cyclopentyl | Me | NMe₂ | 4-(methoxymethyl) pyridine N-oxide |
| 1019 | H | Me | cyclopentyl | Me | NMe₂ | 2-(2-methoxyethyl) pyridine |
| 1020 | H | Me | cyclopentyl | Me | NMe₂ | 2-(2-methoxyethyl) pyridine N-oxide |
| 1021 | H | Me | cyclopentyl | Me | NMe₂ | 3-(2-methoxyethyl) pyridine |

TABLE 1-continued
| Compound No | X | R1 | R2 | R3 | R4 | R5 |
|---|---|---|---|---|---|---|
| 1022 | H | Me |  | Me | NMe$_2$ | 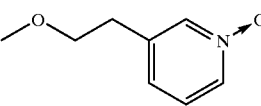 |
| 1023 | H | Me |  | Me | NMe$_2$ | 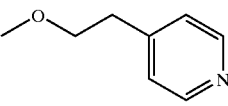 |
| 1024 | H | Me |  | Me | NMe$_2$ | 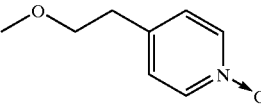 |
| 1025 | H | Me |  | Me | NMe$_2$ | 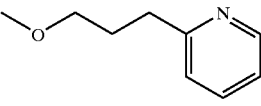 |
| 1026 | H | Me |  | Me | NMe$_2$ | 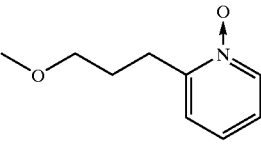 |
| 1027 | H | Me |  | Me | NMe$_2$ | 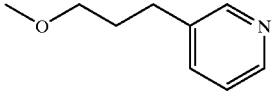 |
| 1028 | H | Me |  | Me | NMe$_2$ | 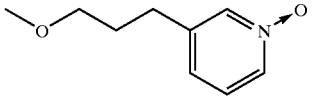 |
| 1029 | H | Me |  | Me | NMe$_2$ | 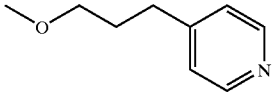 |
| 1030 | H | Me |  | Me | NMe$_2$ | 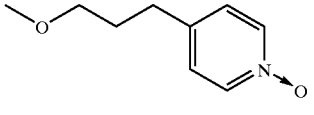 |
| 1031 | H | Me |  | Me | NMe$_2$ | 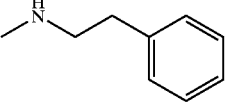 |
| 1032 | H | Me |  | Me | NMe$_2$ | 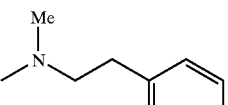 |
| 1033 | H | Me |  | Me | NMe$_2$ | 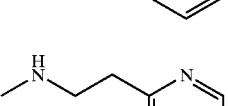 |

TABLE 1-continued
| Compound No | X | R1 | R2 | R3 | R4 | R5 |
|---|---|---|---|---|---|---|
| 1034 | H | Me |  | Me | NMe₂ | 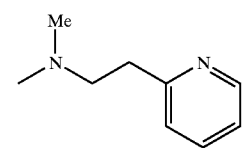 |
| 1035 | H | Me |  | Me | NMe₂ | 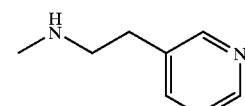 |
| 1036 | H | Me |  | Me | NMe₂ | 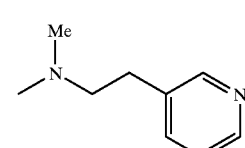 |
| 1037 | H | Me |  | Me | NMe₂ | 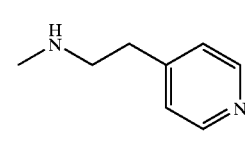 |
| 1038 | H | Me |  | Me | NMe₂ | 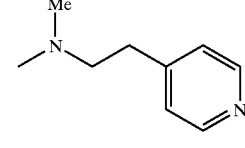 |
| 1039 | H | Me |  | Me | NMe₂ | 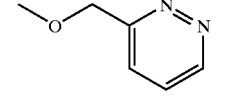 |
| 1040 | H | Me |  | Me | NMe₂ | 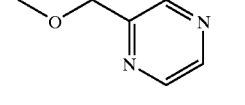 |
| 1041 | H | Me |  | Me | NMe₂ | 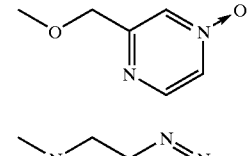 |
| 1042 | H | Me |  | Me | NMe₂ | 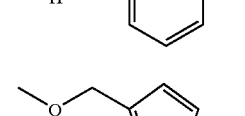 |
| 1043 | H | Me |  | Me | NMe₂ | 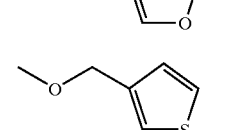 |
| 1044 | H | Me |  | Me | NMe₂ | 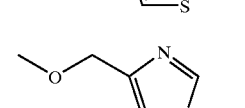 |
| 1045 | H | Me |  | Me | NMe₂ | 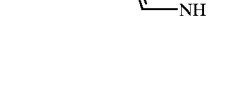 |

TABLE 1-continued

| Compound No | X | R1 | R2 | R3 | R4 | R5 |
|---|---|---|---|---|---|---|
| 1046 | H | Me | cyclopentyl | Me | NMe₂ | NH-CH₂-furan |
| 1047 | H | Me | cyclopentyl | Me | NMe₂ | NH-CH₂-thiophene |
| 1048 | H | Me | cyclopentyl | Me | NMe₂ | NH-CH₂-(1H-pyrrole) |
| 1049 | H | Me | cyclopentyl | Me | NMe₂ | NH-CH₂-(1-Me-pyrrole) |
| 1050 | H | Me | cyclopentyl | Me | NMe₂ | MeO-CH₂-(1,3-diMe-pyrazole) |
| 1051 | H | Me | cyclopentyl | Me | Cl | H |
| 1052 | H | Me | cyclopentyl | Me | Cl | OMe |
| 1053 | H | Me | cyclopentyl | Me | Cl | F |
| 1054 | H | Me | cyclopentyl | Me | Cl | Cl |
| 1055 | H | Me | cyclopentyl | Me | Cl | Br |
| 1056 | H | Me | cyclopentyl | Me | Cl | I |
| 1057 | H | Me | cyclopentyl | Me | Cl | 2-methoxypyridine |
| 1058 | H | Me | cyclopentyl | Me | Cl | 2-methoxypyridine N-oxide |
| 1059 | H | Me | cyclopentyl | Me | Cl | 3-methoxypyridine |

TABLE 1-continued
| Compound No | X | R1 | R2 | R3 | R4 | R5 |
|---|---|---|---|---|---|---|
| 1060 | H | Me |  | Me | Cl | 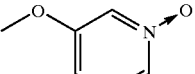 |
| 1061 | H | Me |  | Me | Cl | 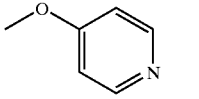 |
| 1062 | H | Me |  | Me | Cl | 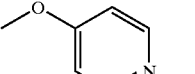 |
| 1063 | H | Me |  | Me | Cl | 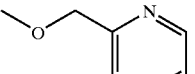 |
| 1064 | H | Me |  | Me | Cl | 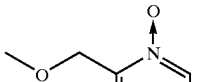 |
| 1065 | H | Me |  | Me | Cl | 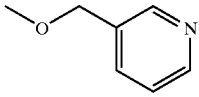 |
| 1066 | H | Me |  | Me | Cl | 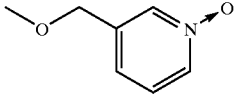 |
| 1067 | H | Me |  | Me | Cl | 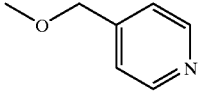 |
| 1068 | H | Me |  | Me | Cl | 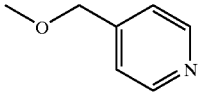 |
| 1069 | H | Me |  | Me | Cl | 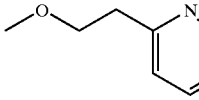 |
| 1070 | H | Me |  | Me | Cl | 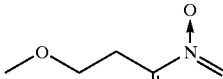 |
| 1071 | H | Me |  | Me | Cl | 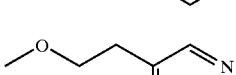 |

TABLE 1-continued
| Compound No | X | R1 | R2 | R3 | R4 | R5 |
|---|---|---|---|---|---|---|
| 1072 | H | Me |  | Me | Cl | 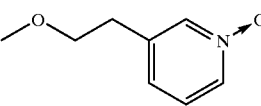 |
| 1073 | H | Me |  | Me | Cl | 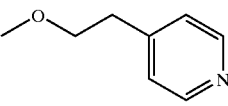 |
| 1074 | H | Me |  | Me | Cl | 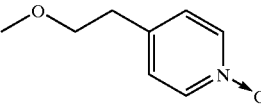 |
| 1075 | H | Me |  | Me | Cl | 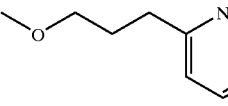 |
| 1076 | H | Me |  | Me | Cl | 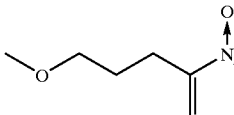 |
| 1077 | H | Me |  | Me | Cl | 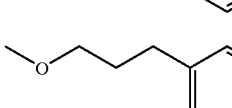 |
| 1078 | H | Me |  | Me | Cl | 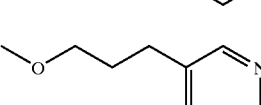 |
| 1079 | H | Me |  | Me | Cl | 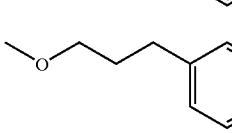 |
| 1080 | H | Me |  | Me | Cl | 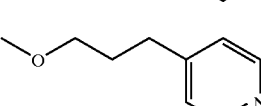 |
| 1081 | H | Me |  | Me | Cl | 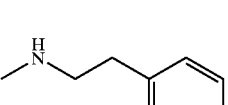 |
| 1082 | H | Me |  | Me | Cl | 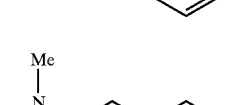 |
| 1083 | H | Me |  | Me | Cl | 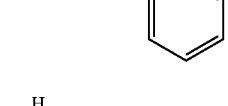 |

TABLE 1-continued
| Compound No | X | R1 | R2 | R3 | R4 | R5 |
|---|---|---|---|---|---|---|
| 1084 | H | Me |  | Me | Cl | 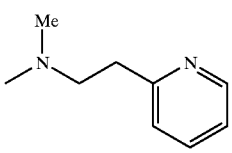 |
| 1085 | H | Me |  | Me | Cl | 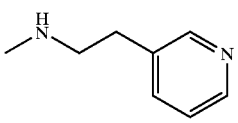 |
| 1086 | H | Me |  | Me | Cl | 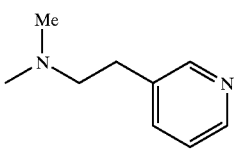 |
| 1087 | H | Me |  | Me | Cl | 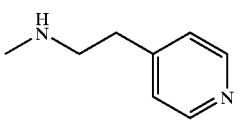 |
| 1088 | H | Me |  | Me | Cl | 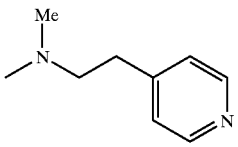 |
| 1089 | H | Me |  | Me | Cl | 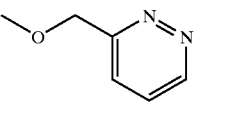 |
| 1090 | H | Me |  | Me | Cl | 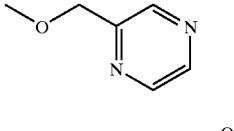 |
| 1091 | H | Me |  | Me | Cl | 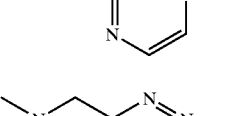 |
| 1092 | H | Me |  | Me | Cl | 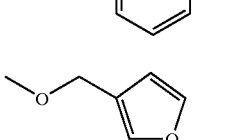 |
| 1093 | H | Me |  | Me | Cl | 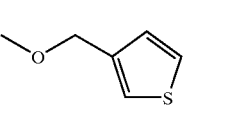 |
| 1094 | H | Me |  | Me | Cl | 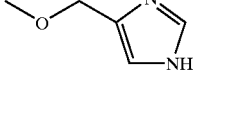 |
| 1095 | H | Me |  | Me | Cl |  |

TABLE 1-continued
| Compound No | X | R1 | R2 | R3 | R4 | R5 |
|---|---|---|---|---|---|---|
| 1096 | H | Me |  | Me | Cl | 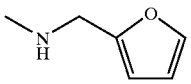 |
| 1097 | H | Me |  | Me | Cl | 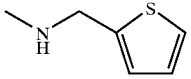 |
| 1098 | H | Me |  | Me | Cl | 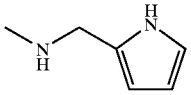 |
| 1099 | H | Me |  | Me | Cl | 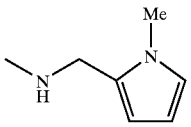 |
| 1100 | H | Me |  | Me | Cl | 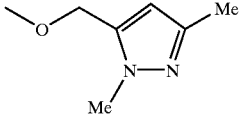 |
| 1101 | H | Me |  | Me |  | H |
| 1102 | H | Me |  | Me |  | OMe |
| 1103 | H | Me |  | Me |  | F |
| 1104 | H | Me |  | Me |  | Cl |
| 1105 | H | Me |  | Me |  | Br |
| 1106 | H | Me |  | Me |  | I |
| 1107 | H | Me |  | Me |  | 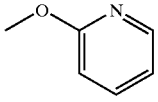 |
| 1108 | H | Me |  | Me |  | 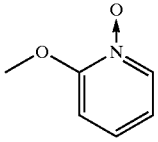 |

TABLE 1-continued

| Compound No | X | R1 | R2 | R3 | R4 | R5 |
|---|---|---|---|---|---|---|
| 1109 | H | Me | cyclopentyl | Me | pyrrolidinyl | 3-methoxypyridine |
| 1110 | H | Me | cyclopentyl | Me | pyrrolidinyl | 3-methoxypyridine N-oxide |
| 1111 | H | Me | cyclopentyl | Me | pyrrolidinyl | 4-methoxypyridine |
| 1112 | H | Me | cyclopentyl | Me | pyrrolidinyl | 4-methoxypyridine N-oxide |
| 1113 | H | Me | cyclopentyl | Me | pyrrolidinyl | 2-(methoxymethyl)pyridine |
| 1114 | H | Me | cyclopentyl | Me | pyrrolidinyl | 2-(methoxymethyl)pyridine N-oxide |
| 1115 | H | Me | cyclopentyl | Me | pyrrolidinyl | 3-(methoxymethyl)pyridine |
| 1116 | H | Me | cyclopentyl | Me | pyrrolidinyl | 3-(methoxymethyl)pyridine N-oxide |
| 1117 | H | Me | cyclopentyl | Me | pyrrolidinyl | 4-(methoxymethyl)pyridine |
| 1118 | H | Me | cyclopentyl | Me | pyrrolidinyl | 4-(methoxymethyl)pyridine N-oxide |
| 1119 | H | Me | cyclopentyl | Me | pyrrolidinyl | 2-(2-methoxyethyl)pyridine |
| 1120 | H | Me | cyclopentyl | Me | pyrrolidinyl | 2-(2-methoxyethyl)pyridine N-oxide |

TABLE 1-continued
| Compound No | X | R1 | R2 | R3 | R4 | R5 |
|---|---|---|---|---|---|---|
| 1121 | H | Me | 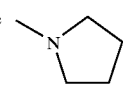 | Me | 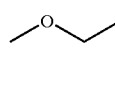 | 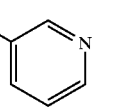 |
| 1122 | H | Me | 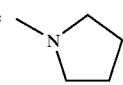 | Me | 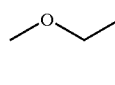 | 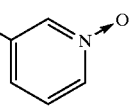 |
| 1123 | H | Me |  | Me | 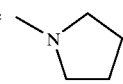 | 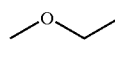 |
| 1124 | H | Me | 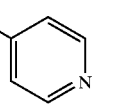 | Me | 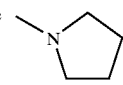 | 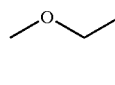 |
| 1125 | H | Me | 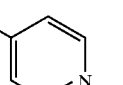 | Me |  | 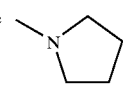 |
| 1126 | H | Me | 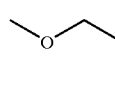 | Me | 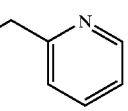 | 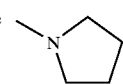 |
| 1127 | H | Me | 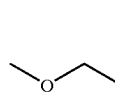 | Me | 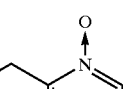 |  |
| 1128 | H | Me | 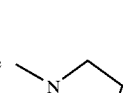 | Me | 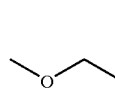 | 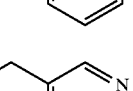 |
| 1129 | H | Me | 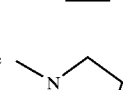 | Me | 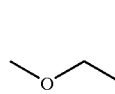 | 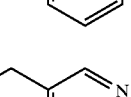 |
| 1130 | H | Me |  | Me | 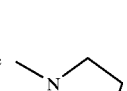 | 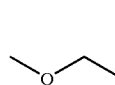 |
| 1131 | H | Me | 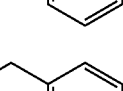 | Me | 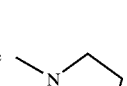 | 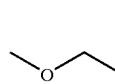 |
| 1132 | H | Me | 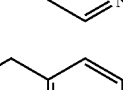 | Me |  | 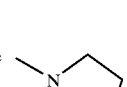 |

TABLE 1-continued
| Compound No | X | R1 | R2 | R3 | R4 | R5 |
|---|---|---|---|---|---|---|
| 1133 | H | Me | 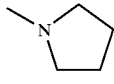 | Me | 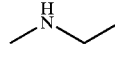 | 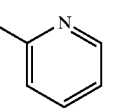 |
| 1134 | H | Me | 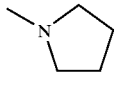 | Me | 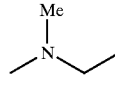 | 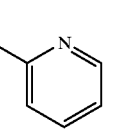 |
| 1135 | H | Me | 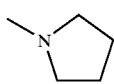 | Me | 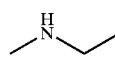 | 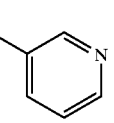 |
| 1136 | H | Me | 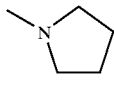 | Me | 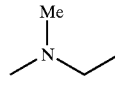 | 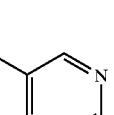 |
| 1137 | H | Me | 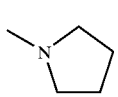 | Me | 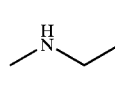 | 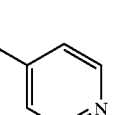 |
| 1138 | H | Me | 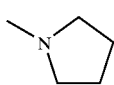 | Me | 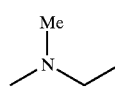 | 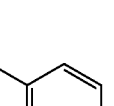 |
| 1139 | H | Me | 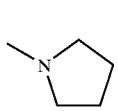 | Me | 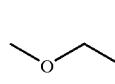 | 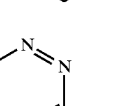 |
| 1140 | H | Me | 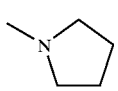 | Me | 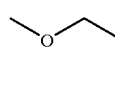 | 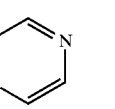 |
| 1141 | H | Me | 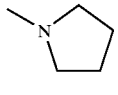 | Me | 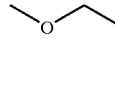 | 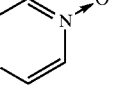 |
| 1142 | H | Me | 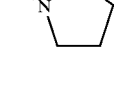 | Me | 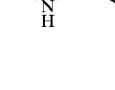 | 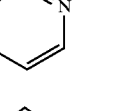 |
| 1143 | H | Me | 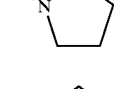 | Me | 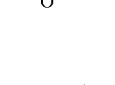 | 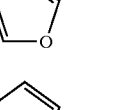 |
| 1144 | H | Me | 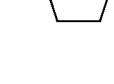 | Me |  | 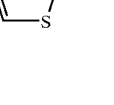 |

TABLE 1-continued
| Compound No | X | R1 | R2 | R3 | R4 | R5 |
|---|---|---|---|---|---|---|
| 1145 | H | Me | 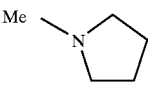 | Me |  | 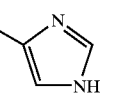 |
| 1146 | H | Me | 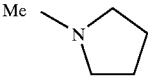 | Me |  | 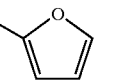 |
| 1147 | H | Me | 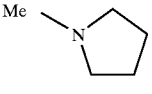 | Me |  | 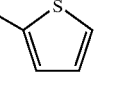 |
| 1148 | H | Me | 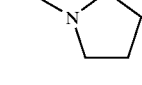 | Me |  | 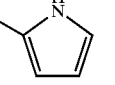 |
| 1149 | H | Me | 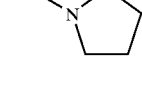 | Me |  | 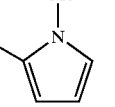 |
| 1150 | H | Me | 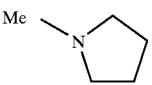 | Me |  | 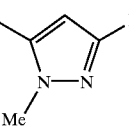 |
| 1151 | H | Me | 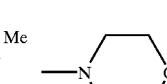 | Me |  | H |
| 1152 | H | Me |  | Me | 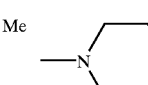 | OMe |
| 1153 | H | Me |  | Me |  | F |
| 1154 | H | Me | 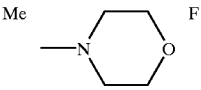 | Me |  | Cl |
| 1155 | H | Me |  | Me | 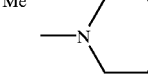 | Br |
| 1156 | H | Me |  | Me |  | I |
| 1157 | H | Me | 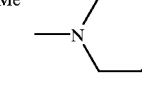 | Me |  |  |

TABLE 1-continued
| Compound No | X | R1 | R2 | R3 | R4 | R5 |
|---|---|---|---|---|---|---|
| 1158 | H | Me |  | Me |  | 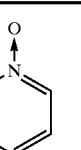 |
| 1159 | H | Me |  | Me |  | 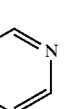 |
| 1160 | H | Me |  | Me |  | 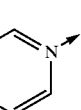 |
| 1161 | H | Me |  | Me |  | 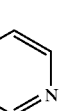 |
| 1162 | H | Me |  | Me |  | 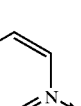 |
| 1163 | H | Me |  | Me |  | 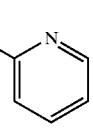 |
| 1164 | H | Me |  | Me |  | 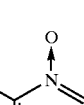 |
| 1165 | H | Me |  | Me |  | 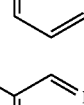 |
| 1166 | H | Me |  | Me |  | 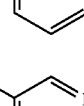 |
| 1167 | H | Me |  | Me |  | 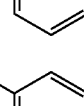 |
| 1168 | H | Me |  | Me |  | 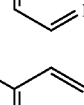 |
| 1169 | H | Me |  | Me |  | 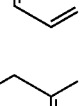 |

TABLE 1-continued

| Compound No | X | R1 | R2 | R3 | R4 | R5 |
|---|---|---|---|---|---|---|
| 1170 | H | Me | cyclopentyl | Me | N-morpholinyl | 2-(2-methoxyethyl)pyridine N-oxide |
| 1171 | H | Me | cyclopentyl | Me | N-morpholinyl | 3-(2-ethoxy)pyridine |
| 1172 | H | Me | cyclopentyl | Me | N-morpholinyl | 3-(2-ethoxy)pyridine N-oxide |
| 1173 | H | Me | cyclopentyl | Me | N-morpholinyl | 4-(2-ethoxy)pyridine |
| 1174 | H | Me | cyclopentyl | Me | N-morpholinyl | 4-(2-ethoxy)pyridine N-oxide |
| 1175 | H | Me | cyclopentyl | Me | N-morpholinyl | 2-(3-propoxy)pyridine |
| 1176 | H | Me | cyclopentyl | Me | N-morpholinyl | 2-(3-propoxy)pyridine N-oxide |
| 1177 | H | Me | cyclopentyl | Me | N-morpholinyl | 3-(3-propoxy)pyridine |
| 1178 | H | Me | cyclopentyl | Me | N-morpholinyl | 3-(3-propoxy)pyridine N-oxide |
| 1179 | H | Me | cyclopentyl | Me | N-morpholinyl | 4-(3-propoxy)pyridine |
| 1180 | H | Me | cyclopentyl | Me | N-morpholinyl | 4-(3-propoxy)pyridine N-oxide |
| 1181 | H | Me | cyclopentyl | Me | N-morpholinyl | N-(2-phenylethyl)amino |

TABLE 1-continued

| Compound No | X | R1 | R2 | R3 | R4 | R5 |
|---|---|---|---|---|---|---|
| 1182 | H | Me | cyclopentyl | Me | morpholinyl | N(Me)CH2CH2-phenyl |
| 1183 | H | Me | cyclopentyl | Me | morpholinyl | NHCH2CH2-(2-pyridyl) |
| 1184 | H | Me | cyclopentyl | Me | morpholinyl | N(Me)CH2CH2-(2-pyridyl) |
| 1185 | H | Me | cyclopentyl | Me | morpholinyl | NHCH2CH2-(3-pyridyl) |
| 1186 | H | Me | cyclopentyl | Me | morpholinyl | N(Me)CH2CH2-(3-pyridyl) |
| 1187 | H | Me | cyclopentyl | Me | morpholinyl | NHCH2CH2-(4-pyridyl) |
| 1188 | H | Me | cyclopentyl | Me | morpholinyl | N(Me)CH2CH2-(4-pyridyl) |
| 1189 | H | Me | cyclopentyl | Me | morpholinyl | OCH2-(pyridazin-3-yl) |
| 1190 | H | Me | cyclopentyl | Me | morpholinyl | OCH2-(pyrazin-2-yl) |
| 1191 | H | Me | cyclopentyl | Me | morpholinyl | OCH2-(pyrazin-2-yl N-oxide) |
| 1192 | H | Me | cyclopentyl | Me | morpholinyl | NHCH2-(pyridazin-3-yl) |

TABLE 1-continued

| Compound No | X | R1 | R2 | R3 R4 | R5 |
|---|---|---|---|---|---|
| 1193 | H | Me |  |  | 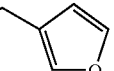 |
| 1194 | H | Me |  |  | 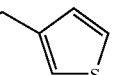 |
| 1195 | H | Me |  |  | 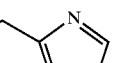 |
| 1196 | H | Me |  |  | 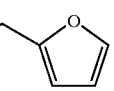 |
| 1197 | H | Me |  |  | 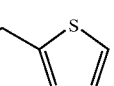 |
| 1198 | H | Me |  |  | 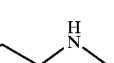 |
| 1199 | H | Me |  |  | 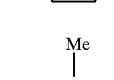 |
| 1200 | H | Me |  |  | 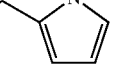 |

Examples of particularly preferred compounds of the present invention include the following compounds. However, the compounds of the present invention are not limited to these examples.

2-chloro-9-[(3-cyclopentyloxy-4-methoxy)benzyl]-6,8-dimethylpurine;
9-[(3-cyclopentyloxy-4-methoxy)benzyl]-6,8-dimethyl-2-methoxypurine;
9-[(3-cyclopentyloxy-4-methoxy)benzyl]-6,8-dimethyl-2-(pyridazinylmethyloxy)purine;
9-[(3-cyclopentyloxy-4-methoxy)benzyl]-6,8-dimethyl-2-[4-pyridylmethyloxy]purine;
4-[[9-[(3-cyclopentyloxy-4-methoxy)benzyl]-6,8dimethylpurin]-2-yl-oxymethyl]-pyridine N-oxide;
9-[(3-cyclopentyloxy-4-methoxy)benzyl]-6,8-dimethyl-2-[2-(4-pyridyl)ethyloxy]purine;
4-[[9-[(3-cyclopentyloxy-4-methoxy)benzyl]-6,8-dimethylpurin]-2-yl-2-oxyethyl]-pyridine N-oxide;
9-[(3-cyclopentyloxy-4-methoxy)benzyl]-6-methylamino-2-(3-pyridazinylmethyloxy)purine;
9-[(3-cyclopentyloxy-4-methoxy)benzyl]-6,8-dimethyl-2-[2-(4-pyridyl)ethylamino]-purine;
9-[(3-cyclopentyloxy-4-methoxy)benzyl]-6,8-dimethyl-2-[(4-pyridyl)methylamino]purine;
9-[(3-cyclopentyloxy-4-methoxy)benzyl]-6,8-dimethyl-2-[3-(4-pyridyl)propyloxy]purine; and
4-[[9-[(3-cyclopentyloxy-4-methoxy)benzyl]-6,8-dimethylpurin]-2-yl-3-oxypropyl]-pyridine N-oxide.

As the salts of the compounds represented by the aforementioned formula (I), physiologically acceptable salts are preferred. Examples include, for example, inorganic acid salts such as hydrochlorides, hydrobromides, hydroiodides, sulfates and phosphates, and organic acid salts such as oxalates, maleates, fumarates, lactates, malates, citrates, tartrates, benzoates, methanesulfonates and p-toluenesulfonates. The compounds of the formula (I), N-oxide derivatives, and salts thereof may exist in the forms of hydrates or solvates, and such hydrates and solvates are also fall within the scope of the present invention. As solvents constituting such solvates, examples include, for example, methanol, ethanol, isopropanol, acetone, ethyl acetate, methylene chloride.

Among the compounds of the present invention, those wherein $R^2$ represents tetrahydrofuranyl group or bicyclo[2,2,1]hept-2-yl group may exist as optical enantiomers. Moreover, depending on the types of substituents, they may have one or more asymmetric carbons, and hence stereoisomers such as optical enantiomers and diastereoisomers based on the asymmetric carbon(s) may exist. Any stereoisomers in a pure form, any mixtures thereof, any racemates thereof and the like fall within the scope of the present invention.

According to the present invention, there are provided the compound represented by the aforementioned formulas (A) and (B). These compounds are useful as synthetic intermediates for the preparation of the aforementioned purine derivatives represented by formula (I). In the compounds represented by the formulas (A) and (B), $R^1$, $R^2$ and $R^4$ have the same meanings as $R^1$, $R^2$ and $R^4$ defined for the compounds of the aforementioned formula (I). $R^1$ is preferably a $C_1$–$C_4$ alkyl group, more preferably a $C_1$–$C_3$ alkyl group, further preferably methyl group or ethyl group, and most preferably methyl group. $R^2$ is preferably tetrahydrofuranyl group, a $C_1$–$C_6$ alkyl group, a $C_1$–$C_3$ haloalkyl group, or a $C_3$–$C_8$ cycloalkyl group, more preferably a $C_3$–$C_8$ cycloalkyl group, further preferably a $C_4$–$C_6$ cycloalkyl group, and most preferably cyclopentyl group. $R^4$ is preferably hydrogen atom, a halogen atom, a $C_1$–$C_4$ alkyl group, a $C_1$–$C_4$ alkoxyl group, a $C_1$–$C_4$ alkylamino group, or a $C_2$–$C_8$ dialkylamino group, and more preferably a $C_1$–$C_3$ alkyl group, a $C_1$–$C_3$ alkoxyl group, or a $C_1$–$C_3$ alkylamino group. $X^2$ represents a halogen atom, and preferably chlorine atom.

Examples of particularly preferred compounds represented by the formula (A) include the following compounds.

4(3-cyclopentyloxy-4-methoxybenzylamino)-2-fluoro-5-nitro-6-methylpyrimidine;

2-chloro-4-(3-cyclopentyloxy-4-methoxybenzylamino)-5-nitro-6-methylpyrimidine;

2-bromo-4-(3-cyclopentyloxy-4-methoxybenzylamino)-5-nitro-6-methylpyrimidine; and 4-(3-cyclopentyloxy-4-methoxybenzylamino)-2-iodide-5-nitro-6-methylpyrimidine.

Examples of particularly preferred compounds represented by the formula (B) include the following compounds.

5-amino-4-(3-cyclopentyloxy-4-methoxybenzylamino)-2-fluoro-6-methylpyrimidine;

5-amino-2chloro-4-(3-cyclopentyloxy-4-methoxybenzylamino)-6-methylpyrimidine;

5-amino-2-bromo-4-(3-cyclopentyloxy-4-methoxybenzylamino)-6-methylpyrimidine; and 5-amino-4-(3-cyclopentyloxy-4-methoxybenzylamino)-2-iodide-6-methylpyrimidine.

Methods for preparing the compounds of the present invention are not particularly limited. For example, they can be prepared by the following methods.

When A is a group represented by the following formula:

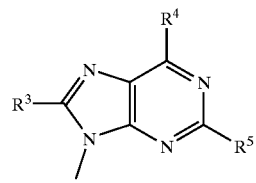

a compound of the following formula (III) can be prepared by the following-preparing method 1 or 2.

<Preparation Method 1>

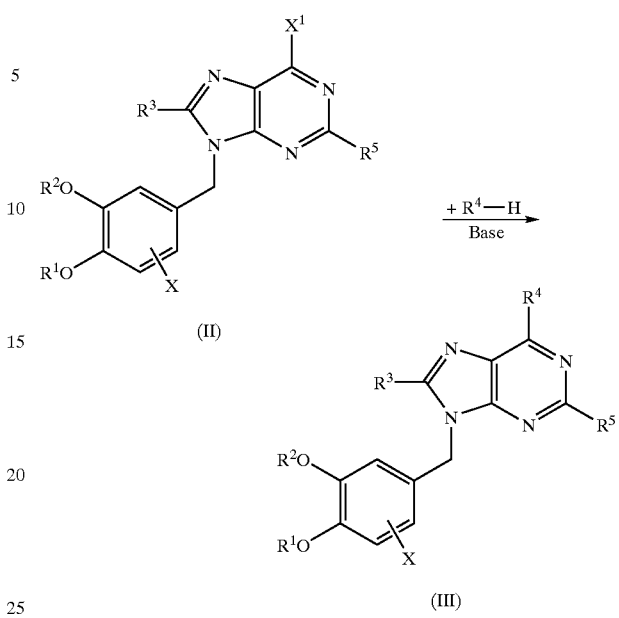

In the scheme, $R^1$, $R^2$, $R^3$, $R^4$, $R^5$, and X have the same meanings as those defined above, and $X^1$ represents a halogen atom.

The above reaction is performed at a temperature within the range of from 0 to 150° C. without a solvent or in a suitable solvent such as N,N-dimethylformamide or tetrahydrofuran, and in the presence or absence of an organic base such as triethylamine, pyridine, and N,N-diethylaniline, or an inorganic base such as sodium carbonate and sodium hydride.

A compound of the aforementioned formula (II) as the starting material of the above reaction can be prepared according to the following scheme.

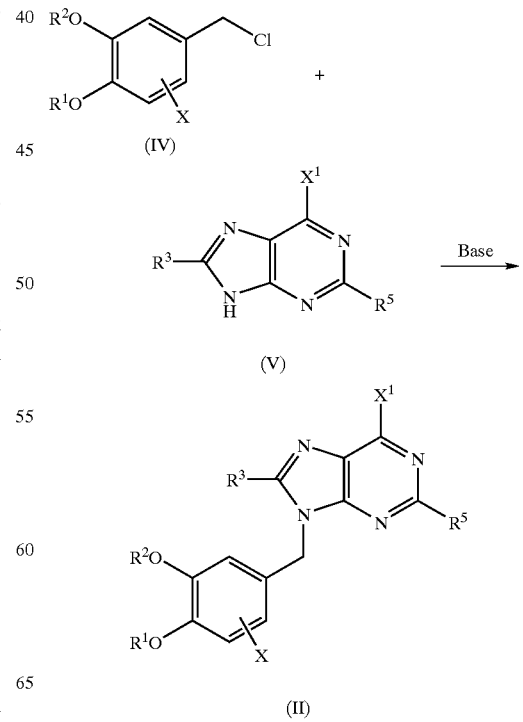

-continued

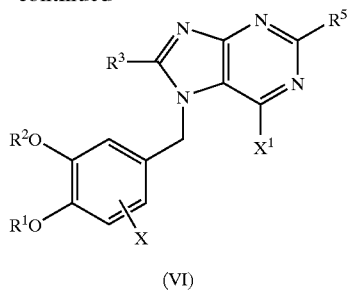

(VI)

In the scheme, $R^1, R^2, R^3, R^4, R^5, X$ and $X^1$ have the same meanings as already defined above.

<Preparation Method 2>

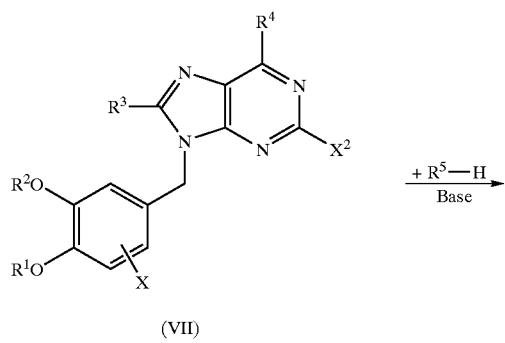

(VII)

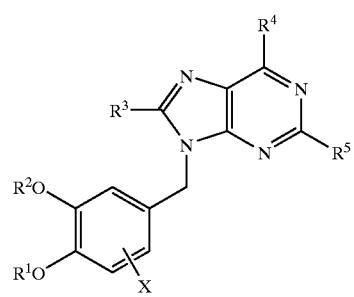

(III)

In the scheme, $R^1$, $R^2$, $R^3$, $R^4$, $R^5$, and X have the same meanings as those defined above, and $X^2$ represents a halogen atom.

A compound of the formula (III) can be prepared by carrying out condensation of a compound of the formula (VII) and a compound represented by $R^5$—H according to the aforementioned reaction. A compound represented by $R^5$—H is added to a suitable solvent such as N,N-dimethylformamide or tetrahydrofuran or a mixed solvent thereof, and the mixture is added with 1 to 5 equivalents of an organic base such as triethylamine, pyridine or N,N-diethylaniline, or an inorganic base such as sodium carbonate or sodium hydride. Then, the mixture is reacted with a compound of the formula (VII) to obtain the target compound of the formula (III). The reaction is usually performed at from −20 to 150° C. under a nitrogen or argon flow. A compound of the aforementioned formula (VII) as the starting material of the aforementioned reaction can be prepared by any one of the following three methods.

Preparation Method (1)

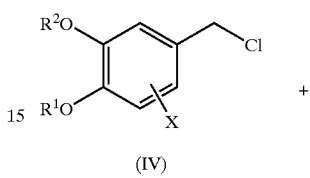

(IV)

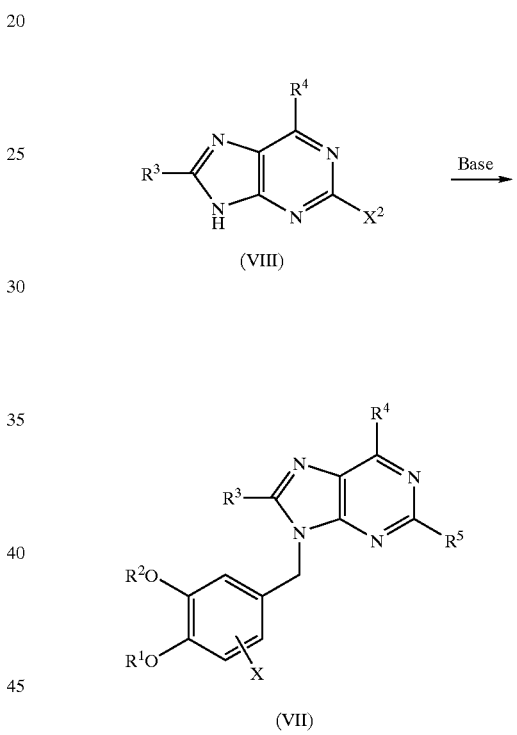

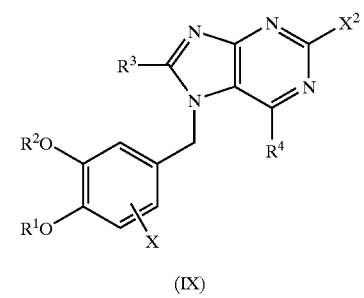

(IX)

In the scheme, $R^1$, $R^2$, $R^3$, $R^4$, $R^5$, X, and $X^2$ have the same meanings as those defined above.

Preparation Method (2)

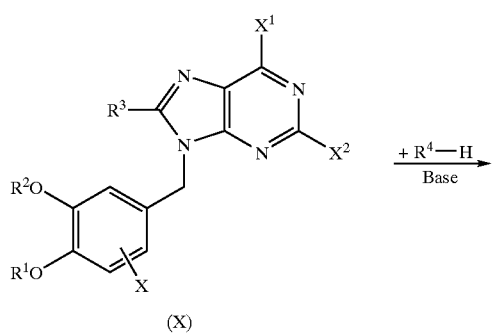

In the scheme, $R^1$, $R^2$, $R^3$, $R^4$, $R^5$, X, $X^1$, and $X^2$ have the same meanings as those defined above.

Preparation Method (3)

When $X^2$ is a halogen atom, a compound of the formula (VII) can also be prepared according to the following reaction formula.

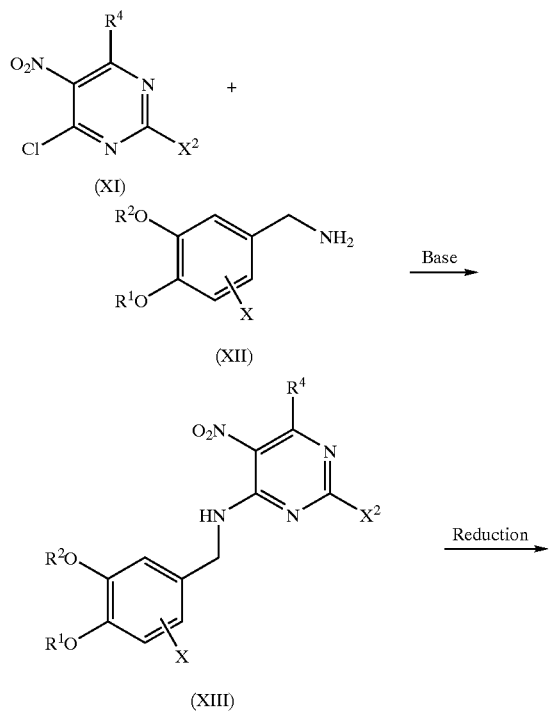

In the scheme, $R^1$, $R^2$, $R^3$, $R^4$, $R^5$, and X have the same meanings as those defined above, and $X^2$ represents a halogen atom.

In the above reaction, a compound of the formula (XI) and a compound of the formula (XII) are first condensed to prepare a compound of the formula (XIII). The compound of the formula (XI) and the compound of the formula (XII) are added to a suitable solvent such as N,N-dimethylformamide, tetrahydrofuran, methylene chloride or water, or a mixed solvent comprising a combination of these solvents, and the mixture is then added with 1 to 5 equivalents of an organic base such as triethylamine, pyridine or N,N-diethylaniline, or an inorganic base such as sodium carbonate or sodium hydride to obtain the target compound of the formula (XIII). The reaction is usually performed at −20 to 150° C. under a nitrogen or argon flow.

Then, a compound of the formula (XIV) can be obtained by reducing the compound of the formula (XIII). The reduction can be performed by dissolving the compound of the formula (XIII) in a solvent such as methanol, ethanol or tetrahydrofuran, or a mixed solvent comprising a combination of such solvents, adding 10 to 100% by weight of a catalyst such as Raney Nickel, palladium/carbon, hydroxylated palladium/carbon or platinum to the solution, and then performing the reaction at a temperature of from room temperature to 60° C. under a hydrogen flow or under pressure. A compound of the formula (VII) can be obtained by allowing a compound of the formula (XIV) to react with 1 to 5 equivalents of a regent such as triethyl orthoformate or triethyl orthoacetate in the absence of a solvent or in the presence of 1 to 5 equivalents of an organic acid such as acetic acid, trifluoroacetic acid or p-toluenesulfonic acid, or an inorganic acid such as hydrochloric acid. The reaction can generally be performed at a temperature of from room temperature to 250° C. The compounds of the formula (A) and the formula (B), useful as synthetic intermediates of the compounds of the formula (I), correspond to the compounds of the formula (XIII) and formula (XIV) wherein X is hydrogen atom, respectively.

<Preparation Method 3>

When A is a group represented by the following formula:

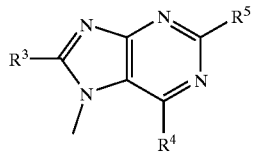

a compound of the following formula (XV) can be prepared by a method similar to Preparation Methods 1 and 2 using a compound of the aforementioned formula (VI) or a compound of the formula (IX).

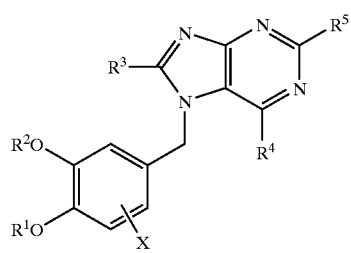

(XV)

In the formula, $R^1$, $R^2$, $R^3$, $R^4$, $R^5$, and X have the same meanings as those defined above.

N-oxide compounds can be prepared by oxidizing a starting material by an ordinarily used method.

When the compounds of present invention are used as active ingredients of the medicaments, the compounds, per se, may be administered, or they may be administered as pharmaceutical compositions which are prepared by using pharmaceutically acceptable additives for pharmaceutical preparations. The composition of the pharmaceutical compositions may be chosen depending on solubility and chemical properties of the aforementioned compounds as active ingredients, as well as administration route and schedule. For example, the composition may be orally administered in the forms of granules, powders, tablets, hard capsules, soft capsules, syrups, emulsions, suspensions, solutions and the like, or intravenously, intramuscularly or subcutaneously administered as injections. The composition may be prepared as powders for injection, and administered as injection prepared just before use.

For the manufacture of pharmaceutical compositions suitable for oral, enteral, parenteral, or topical administration, organic or inorganic pharmaceutical additives can be used. These additives may be a solid or liquid, and examples include carriers and diluents for pharmaceutical formulations and the like. As excipients used for the manufacture of solid pharmaceutical compositions, for example, lactose, sucrose, starch, talc, cellulose, dextrin and the like can be used. For the manufacture of liquid pharmaceutical compositions for oral administration such as emulsions, syrups, suspensions and solutions, commonly used inactive diluents, for example, water, vegetable oils and the like can be used. The pharmaceutical compositions may contain, for example, wetting agents, suspension aids, sweeteners, aromatics, colorants, preservatives and the like as auxiliaries, as well as inactive diluents. A liquid preparation may be prepared and filled in capsules made of a material that can be disintegrated in body such as gelatin. As solvents or suspending agents used for the manufacture pharmaceutical compositions for parenteral administration such as injections, examples include water, propylene glycol, polyethylene glycol, benzyl alcohol, ethyl oleate, lecitin and the like. Method for preparing the pharmaceutical compositions are not particularly limited, and any methods for preparing formulations available in the art can be utilized.

The medicaments of the present invention can be used as, for example, antiasthmatic agents for therapeutic and/or preventive treatment of asthma. Doses of the medicaments of the present invention for oral administration are generally 0.01 to 1000 mg (as a weight of an active ingredient), preferably 0.01 to 100 mg, per day for an adult. Preferably, the aforementioned doses are suitably increased or decreased depending on various conditions including the age, conditions and symptoms of a patient, and the presence or absence of a medicament simultaneously administered and the like. The aforementioned daily dose may be administered once a day or twice or three times a day as divided portions with suitable intervals, or intermittently administered every several days. When the medicaments are used as injections or drip infusions, they are preferably administered continuously or intermittently in a dose of from 0.001 to 100 mg (a weight of an active ingredient) per day for an adult.

EXAMPLES

The present invention will be explained more specifically with reference to examples and test examples. However, the scope of present invention is not limited by the examples and test examples.

Example 1

Synthesis of 2-Chloro-4-(3-cyclopentyloxy-4-methoxybenzylamino)-5-nitro-6-methylpyrimidine 2,4-Dichloro-5-nitro-6-methylpyrimidine (2.0 g) was dissolved in tetrahydro-furan (14 ml) and added with a solution of 3-cyclopentyloxy-4-methoxybenzylamine (2.25 g) dissolved in tetrahydrofuran (7 ml) with stirring and cooling on a salt-ice bath (−10° C.). Then, the mixture was added dropwise with triethylamine (1.4 ml), and stirred for 30 minutes on a salt-ice bath (−10° C.). The reaction mixture was further added with saturated brine, and then extracted with ethyl acetate. The organic layer was dried over anhydrous sodium sulfate and concentrated under reduced pressure, and the resulting residue was suspended and washed in a mixed solvent of ether and hexane (50:50) to obtain 3.11 g of the title compound.

$^1$H-NMR (CDCl$_3$) δ ppm: 1.59–1.64 (m, 2H), 1.80–1.96 (m, 6H), 2.73 (s, 3H), 3.84 (s, 3H), 4.70 (d, 2H, J=5.4 Hz), 4.74–4.79 (m, 1H), 6.83–6.91 (m, 3H), 8.36 (bs, 1H).

Example 2

Synthesis of 5-Amino-4-(3-cyclopentyloxy-4-methoxybenzylamino)-2-chloro-6-methylpyrimidine 2-Chloro-4-(3cyclopentyloxy-4-methoxybenzyl)-5-nitro-6-methylpyrimidine (2.0 g) was dissolved in tetrahydrofuran (14 ml), and the solution was added with methanol (14 ml) and further added with Raney Nickel (1.8 g) under nitrogen atmosphere. The mixture was stirred at room temperature under hydrogen gas atmosphere for 4.5 hours. After the reaction was completed, the reaction suspension was filtered through Celite under nitrogen atmosphere while washing with methanol. The resulting organic layer was concentrated under reduced pressure, and the residue was recrystallized from ether to obtain 1.65 g of the title compound.

$^1$H-NMR (CDCl$_3$) δ ppm: 1.57–1.66 (m, 2H), 1.78–1.97 (m, 6H), 2.31 (s, 3H), 2.90 (bs, 2H), 3.83 (s, 3H), 4.54 (d, 2H, J=5.4 Hz), 4.71–4.77 (m, 1H), 5.30 (bs, 1H), 6.79–6.93 (m, 3H).

Example 3

Synthesis of 2-Chloro-9-[(3-cyclopentyloxy-4-methoxy)benzyl]-6,8-dimethylpurine (Compound No. 131 in Table 2)

5-Amino-4-(3-cyclopentyloxy-4-methoxybenzyl)-2-chloro-6-methylpyrimidine (20.0 g) was added with triethyl orthoacetate (8.9 g) and acetic acid (3.3 g), and the mixture was heated for 3 hours with stirring under heating at 100° C., while ethanol generated during the reaction was removed from the reaction system. After the reaction was completed, the reaction mixture was cooled to room temperature and diluted by adding methylene chloride. The mixture was washed with saturated aqueous sodium hydrogencarbonate, and then with saturated brine. The organic layer was dried over anhydrous magnesium sulfate, and concentrated under reduced pressure. The residue was purified by silica gel column chromatography (chloroform:ethyl acetate=80:20) to obtain 18.9 of the title compound.

$^1$H-NMR (CDCl$_3$) δ ppm: 1.59–1.63 (m, 2H), 1.76–1.90 (m, 6H), 2.58 (s, 3H), 2.80 (s, 3H), 3.81 (s, 3H), 4.64–4.68 (m, 1H), 5.28 (s, 2H), 6.70 (dd, 1H, J=8.2, 2.0 Hz), 6.78 (d, 1H, J=8.2 Hz), 6.88 (d, 1H, J=2.0 Hz).

Example 4

Synthesis of 9-[(3-Cyclopentyloxy-4-methoxy)benzyl]-6,8-dimethyl-2-[3-(4-pyridyl)propyloxy]purine (Compound No. 100 in Table 2)

4-Pyridinepropanol (29.91 g) was dissolved in tetrahydrofuran (560 ml), andt the solution was added with 60% sodium hydride (8.72 g) and stirred at room temperature for 15 minutes. The mixture was added portionwise with 2-chloro-9-[(3-cyclopentyloxy-4-methoxy)benzyl]-6,8-dimethylpurine (59.10 g) and refluxed by heating for 2 hours. The reaction mixture was cooled and concentrated under reduced pressure, and then the mixture was added with water and extracted with ethyl acetate. The organic layer was washed with saturated brine, dried over anhydrous magnesium sulfate, and then concentrated under reduced pressure. The residue was purified by silica gel column chromatography (chloroform:methanol=90:10) to obtain 68.19 g of the title compound.

$^1$H-NMR (CDCl$_3$) δ ppm: 1.54–1.81 (m, 8H), 2.15–2.22 (m, 2H), 2.86 (t, 2H, J=6.9 Hz), 3.80 (s, 3H), 4.43 (t, 2H, J=6.9 Hz), 4.62–4.64 (m, 1H), 5.23 (s, 2H), 6.67–6.79 (m, 3H), 7.16 (d, 2H, J=6.7 Hz), 8.48 (d, 2H, J=6.7 Hz).

Example 5

Synthesis of 4-[[9-[(3-Cyclopentyloxy-4-methoxy)benzyl]-6,8-dimethylpurin]-2-yl-3-oxypropyl]pyridine N-oxide (Compound No. 120 in Table 2)

9-[(3-Cyclopentyloxy-4-methoxy)benzyl]-6,8-dimethyl-2-[3-(4-pyridyl)propoxy]purine (3 g) was dissolved in methylene chloride (30 ml), and the solution was added with MMPP (magnesium monoperoxyphthalate hexahydrate, 3.85 g) dissolved in distilled water (30 ml) with ice cooling, and then the mixture was stirred at room temperature for 3 hours. After complete consumption of the starting material was observed by TLC, the reaction mixture was poured into 5% aqueous solution of sodium sulfate with ice cooling, and the mixture was stirred at room temperature to decompose excessive MMPP. The reaction mixture was extracted with methylene chloride, washed with saturated aqueous sodium hydrogencarbonate, and further washed with saturated brine. The resulting organic layer was dried over anhydrous sodium sulfate, and concentrated under reduced pressure. The residue was purified by silica gel column chromatography (chloroform:methanol=90:10), and the resulting compound was recrystallized from THF-heptane to obtain 2.22 g of the title compound.

$^1$H-NMR (CDCl$_3$) δ ppm: 1.56–1.81 (m, 8H), 2.10–2.19 (m, 2H), 2.51 (s, 3H), 2.75 (s, 3H), 2.85–2.90 (m, 2H), 3.81 (s, 3H), 4.40–4.44 (m, 2H), 4.63–4.64 (m, 1H), 5.24 (s, 2H), 6.65–6.79 (m, 3H), 7.14 (d, 2H, J=6.7 Hz), 8.13 (d, 2H, J=6.7 Hz).

Example 6

Synthesis of 2-Chloro-9-[(3-cyclopentyloxy-4-methoxy)benzyl]-6-methylaminopurine (Compound No. 136 in Table 2)

9-[(3-Cyclopentyloxy-4-methoxy)benzyl]-2,6-dichloropurine (8.07 g) was dissolved in tetrahydrofuran (80 ml), added dropwise with methylamine (40% solution in methanol, 8.0 g) with stirring and cooling on an ice bath, and the mixture was stirred at room temperature for 1 hour. The reaction mixture was concentrated under reduced pressure, and the residue was added with water and extracted with ethyl acetate. The organic layer was washed with saturated brine, dried over anhydrous magnesium sulfate, and then concentrated under reduced pressure to obtain 7.81 g of the title compound.

Example 7

Synthesis of 9-[(3-Cyclopentyloxy-4-methoxy)benzyl]-6-methylamino-2-(3-pyridazinylmethyloxy)purine (Compound No. 79 in Table 2)

3-Pyridazinylmethanol (4.41 g) was dissolved in N,N-dimethylformamide (100 ml), added with 60% sodium hydride (1.60 g), and stirred at room temperature for 30 minutes. The reaction mixture was added portionwise with 2-chloro-9-[(3-cyclo-pentyloxy-4-methoxy)benzyl]-6-methylaminopurine (7.76 g), and then the mixture was stirred at 85° C. for 2 hours with heating. The reaction mixture was cooled, and concentrated under reduced pressure. The residue was added with water, and extracted with ethyl acetate. The organic layer was washed with saturated brine, dried over anhydrous magnesium sulfate, and then concentrated under reduced pressure. The residue was purified by silica gel column chromatography to obtain 3.23 g of the title compound.

Example 8

According to the methods of Examples 1 to 7, compounds shown in Table 2 and Table 3 below were obtained (in the tables, melting points are indicated as ° C.).

TABLE 2
| Compound No | X | R1 | R2 | R3 | R4 | R5 | Physicochemical property |
|---|---|---|---|---|---|---|---|
| 1 | H | Me | 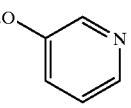 | H |  | H | amorphous solid |
| 2 | H | Me | 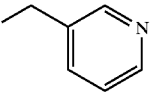 | H |  | H | oil |
| 3 | H | Me | 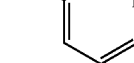 | H | 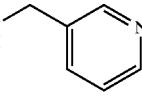 | H | mp 138–140 |
| 4 | Br | Me | Me | H |  | H | mp 185–186 |
| 5 | H | Me | 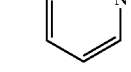 | H | 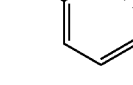 | H | mp 76–83 |
| 6 | Br | Me | Me | H | 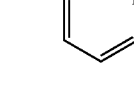 | H | mp 80–82 |
| 7 | H | Me | Me | H | 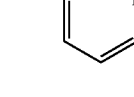 | H | oil |
| 8 | H | Me | i-Pr | H |  | H | oil |
| 9 | H | Me | 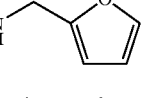 | H |  | H | mp 142–144 |
| 10 | H | Me | 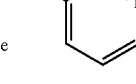 | H | 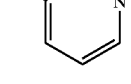 | H | oil |
| 11 | Br | Me | Me | H | 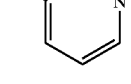 | H | mp 152–154 |

TABLE 2-continued

| Compound No | X | R1 | R2 | R3 | R4 | R5 | Physicochemical property |
|---|---|---|---|---|---|---|---|
| 12 | H | Me | cyclopentyl | H | —NH-CH2-benzimidazole | H | mp 219–223 |
| 13 | H | Me | cyclopentyl | H | NH-CH2CH2-(3-pyridyl) | H | mp 113–116 |
| 14 | H | Me | cyclopentyl | H | NH-CH2CH2-(2-pyridyl) | H | oil |
| 15 | H | Me | cyclopentyl | H | NH-CH2-pyrazinyl | H | oil |
| 16 | H | Me | cyclopentyl | H | H | OCH2-(3-pyridyl) | mp 114–115 |
| 17 | H | Me | cyclopentyl | H | H | OCH2-(2-pyridyl) | mp 129–130 |
| 18 | H | Me | cyclopentyl | H | H | OCH2-(4-pyridyl) | mp 105 |
| 19 | H | Me | cyclopentyl | H | H | OCH2-(4-pyridyl N-oxide) | mp 105–106 |
| 20 | H | Me | cyclopentyl | H | H | O-(3-methoxypyridyl) | amorphous solid |
| 21 | H | Me | cyclopentyl | H | H | OCH2-(2-pyridyl N-oxide) | mp 132 |

TABLE 2-continued
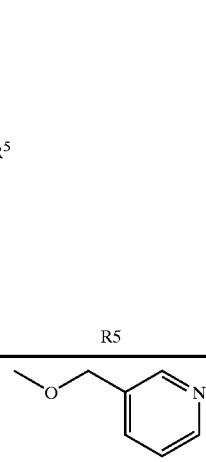
| Compound No | X | R1 | R2 | R3 | R4 | R5 | Physicochemical property |
|---|---|---|---|---|---|---|---|
| 22 | H | Me | i-Pr | H | H |  | mp 85–88 |
| 23 | H | Me | 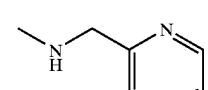 | H | H |  | mp 122–123 |
| 24 | H | Me | 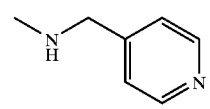 | H | H |  | mp 157–158 |
| 25 | H | Me | 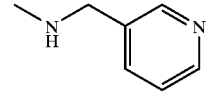 | H | H |  | mp 123–124 |
| 26 | H | Me | 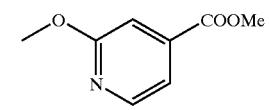 | H | H |  | mp 130–131 |
| 27 | H | Me | 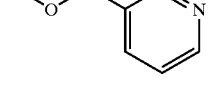 | H | H |  | mp 114–118 |
| 28 | H | Me | 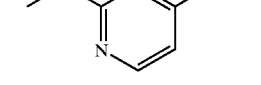 | H | H |  | amorphous solid |
| 29 | H | Me | 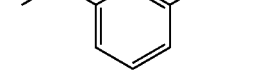 | H | H |  | mp 122–123 |
| 30 | H | Me | 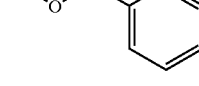 | OH | H |  | mp 167–169 |
| 31 | H | Me | 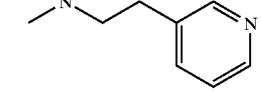 | H | H |  | mp 110 |
| 32 | H | Me | 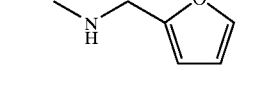 | H | H |  | mp 159 |

TABLE 2-continued

| Compound No | X | R1 | R2 | R3 | R4 | R5 | Physicochemical property |
|---|---|---|---|---|---|---|---|
| 33 | H | Me | cyclopentyl | OH | H | OCH2-(3-pyridyl) | mp 91–93 |
| 34 | H | Me | cyclopentyl | H | H | NHMe-CH2CH2-(2-pyridyl) | mp 116–117 |
| 35 | H | Me | cyclopentyl | H | H | NHMe-CH2CH2-(4-pyridyl) | mp 108–109 |
| 36 | H | Me | cyclopentyl | Me | H | OCH2-(3-pyridyl) with OMe | oil |
| 37 | H | Me | cyclopentyl | Me | H | NHMe-CH2-(3-pyridyl) | oil |
| 38 | H | Me | cyclopentyl | Me | H | NHMe-CH2-(4-pyridyl) | mp 181–183 |
| 39 | H | Me | cyclopentyl | Me | H | NHMe-CH2-(2-pyridyl) | mp 77–79 |
| 40 | H | Me | cyclopentyl | Me | H | NHMe-CH2CH2-(4-pyridyl) | mp 110–112 |
| 41 | H | Me | cyclopentyl | H | H | NHMe-CH2-(2-thienyl) | mp 141–142 |
| 42 | H | Me | cyclopentyl | H | H | NHMe-CH2CH2-(1-methylpyrrol-2-yl) | mp 120–121 |

TABLE 2-continued
| Compound No | X | R1 | R2 | R3 | R4 | R5 | Physicochemical property |
|---|---|---|---|---|---|---|---|
| 43 | H | Me | 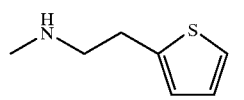 | H | H |  | mp 112–113 |
| 44 | H | Me | 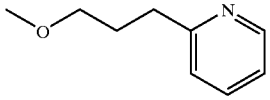 | H | H |  | oil |
| 45 | H | Me | 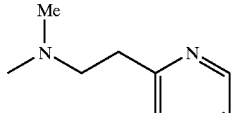 | H | H |  | oil |
| 46 | H | Me | 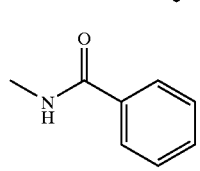 | H | H |  | amorphous solid |
| 47 | H | Me | 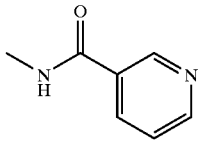 | H | H |  | mp 255 (dec.) |
| 48 | H | Me | 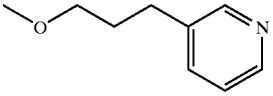 | H | H |  | mp 77–78 |
| 49 | H | Me | 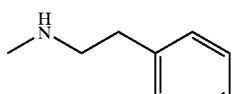 | H | H |  | mp 110–111 |
| 50 | H | Me | 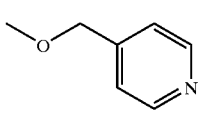 | Me | H |  | mp 114–116 |
| 51 | H | Me | 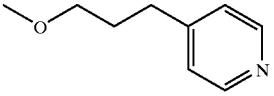 | H | H |  | mp 97–98 |
| 52 | H | Me | 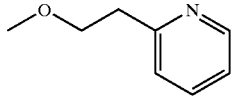 | H | H | | oil |

TABLE 2-continued
| Compound No | X | R1 | R2 | R3 | R4 | R5 | Physicochemical property |
|---|---|---|---|---|---|---|---|
| 53 | H | Me | 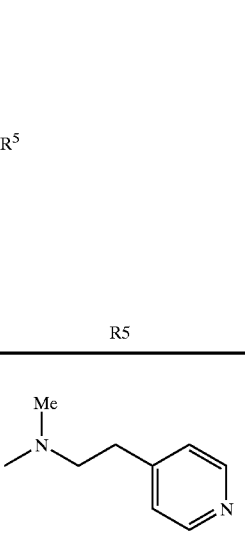 | H | H |  | oil |
| 54 | H | Me | 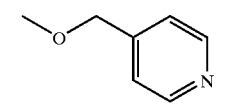 | H | H |  | mp 116–118 |
| 55 | H | Me | 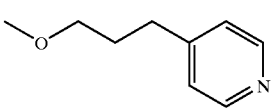 | H | H |  | mp 128–130 |
| 56 | H | Me | 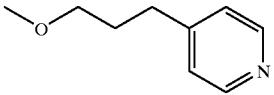 | Me | H | 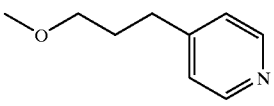 | mp 115–117 |
| 57 | H | Me | i-Pr | Me | H | 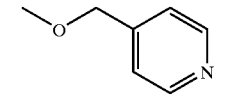 | mp 129–132 |
| 58 | H | Me | i-Pr | Me | H |  | mp 142–144 |
| 59 | H | Me | 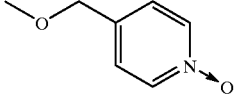 | Me | H |  | mp 183–185 |
| 60 | H | Me | 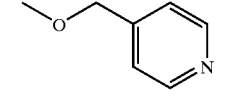 | MeO | MeO |  | amorphous solid |
| 61 | H | Me | 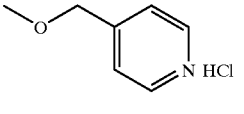 | Me | H |  | mp 154–156 |
| 62 | H | Me | 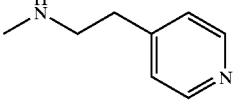 | Me | H | | amorphous solid |

TABLE 2-continued
| Compound No | X | R1 | R2 | R3 | R4 | R5 | Physicochemical property |
|---|---|---|---|---|---|---|---|
| 63 | H | Me | 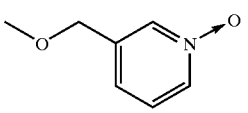 | H | H |  | mp 161–162 |
| 64 | H | Me | 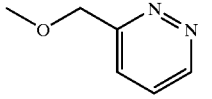 | Me | H |  | mp 82–84 |
| 65 | H | Me | 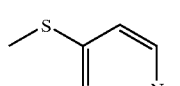 | H | H |  | mp 216–217 |
| 66 | H | Me | 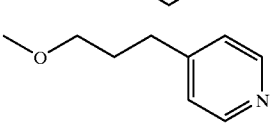 | H | NH$_2$ |  | mp 152–153 |
| 67 | H | Me | 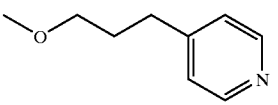 | H | Me |  | mp 102 |
| 68 | H | Me | 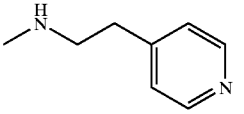 | H | MeNH |  | mp 131–132 |
| 69 | H | Me | 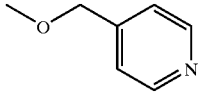 | H | Me |  | mp 138–139 |
| 70 | H | Me | 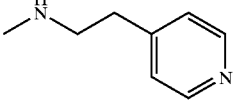 | H | Me |  | mp 105–106 |
| 71 | H | Me | 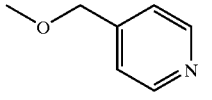 | H | MeNH |  | mp 152–153 |
| 72 | H | Me | 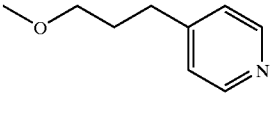 | H | MeNH |  | mp 138–140 |
| 73 | H | Me | 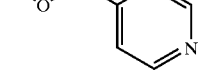 | H | MeO |  | mp 144 |

TABLE 2-continued

| Compound No | X | R1 | R2 | R3 | R4 | R5 | Physicochemical property |
|---|---|---|---|---|---|---|---|
| 74 | H | Me | cyclopentyl | H | MeO | 3-(4-pyridyl)propyl methyl ether | oil |
| 75 | H | Me | cyclopentyl | H | MeO | N-methyl-2-(4-pyridyl)ethylamine | oil |
| 76 | H | Me | cyclopentyl | H | Me | 3-(methoxymethyl)pyridazine | oil |
| 77 | H | Me | cyclopentyl | Me | H | N-methyl-[6-(2,2,2-trifluoroethoxy)pyridin-3-yl]methylamine | mp 125–127 |
| 78 | H | Me | cyclopentyl | Me | H | 5-(methoxymethyl)-2-(2,2,2-trifluoroethoxy)pyridine | mp 99–100 |
| 79 | H | Me | cyclopentyl | H | MeNH | 3-(methoxymethyl)pyridazine | mp 176–177 |
| 80 | H | Me | cyclopentyl | H | MeO | 3-(methoxymethyl)pyridazine | mp 147–149 |
| 81 | H | Me | cyclopentyl | H | Me | N-methyl-(furan-2-yl)methylamine | mp 141–142 |
| 82 | H | Me | cyclopentyl | H | Me₂N | 3-(4-pyridyl)propyl methyl ether | mp 78–80 |
| 83 | H | Me | cyclopentyl | H | EtNH | 3-(4-pyridyl)propyl methyl ether | mp 127–128 |

TABLE 2-continued
| Compound No | X | R1 | R2 | R3 | R4 | R5 | Physicochemical property |
|---|---|---|---|---|---|---|---|
| 84 | H | Me | 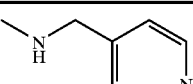 | H | Me |  | mp 137–138 |
| 85 | H | Me | 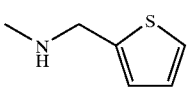 | H | Me |  | mp 155 |
| 86 | H | Me |  | H | 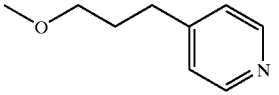 |  | mp 131–132 |
| 87 | H | Me | 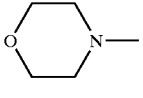 | H | 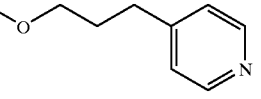 |  | mp 121 |
| 88 | H | Me | 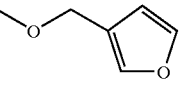 | H | Me$_2$N |  | mp 92–93 |
| 89 | H | Me | 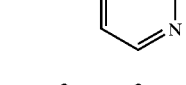 | H | Me$_2$N |  | mp 88–89 |
| 90 | H | Me | 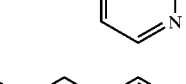 | Et | H | 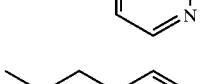 | mp 134–136 |
| 91 | H | Me | CF$_3$CH$_2$ | Me | H |  | mp 129–130 |
| 92 | H | Me | 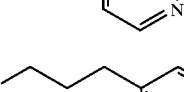 | H | Et |  | mp 104–106 |
| 93 | H | Me | 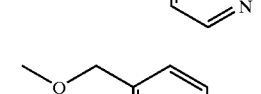 | H | n-PrNH | 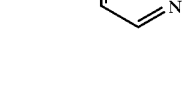 | mp 130–131 |
| 94 | H | Me | n-Bu | Me | H |  | mp 94–97 |

TABLE 2-continued
| Compound No | X | R1 | R2 | R3 | R4 | R5 | Physicochemical property |
|---|---|---|---|---|---|---|---|
| 95 | H | Me | 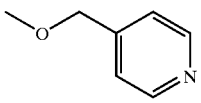 | Me | Me |  | mp 125–126 |
| 96 | H | Me | 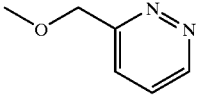 | H | EtNH | 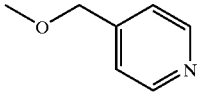 | mp 121–122 |
| 97 | H | Me | t-Bu | Me | H |  | mp 162–163 |
| 98 | H | Me | 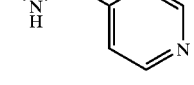 | Me | Me |  | mp 138–139 |
| 99 | H | Me | 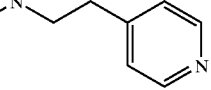 | Me | Me |  | oil |
| 100 | H | Me | 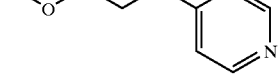 | Me | Me |  | mp 105–106 |
| 101 | H | Me | 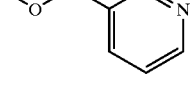 | Me | Me |  | amorphous solid |
| 102 | H | Me | 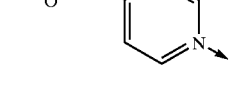 | Me | Me |  | mp 157–158 |
| 103 | H | Me | 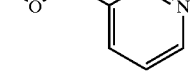 | H | Me$_2$N |  | amorphous solid |
| 104 | H | Me | 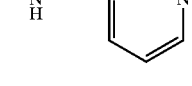 | H | Me$_2$N |  | mp 112–114 |
| 105 | H | Me | 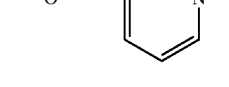 | Me | Me |  | mp 130–131 |

TABLE 2-continued

| Compound No | X | R1 | R2 | R3 | R4 | R5 | Physicochemical property |
|---|---|---|---|---|---|---|---|
| 106 | H | Me | n-Bu | H | MeNH | 3-(methoxymethyl)pyridazine | mp 165–166 |
| 107 | H | Me | n-Bu | H | Me₂N | 4-(methoxymethyl)pyridine | mp 105–107 |
| 108 | H | Me | cyclopentyl | H | Et | N-methyl-2-(pyridin-4-yl)ethylamine | mp 127–129 |
| 109 | H | Me | cyclopentyl | Me | Me | 3-(methoxymethyl)pyrazine | oil |
| 110 | H | Me | cyclopentyl | H | NH₂ | 3-(methoxymethyl)pyridazine | mp 141–142 |
| 111 | H | Me | cyclopentyl | Me | Me | 3-(methoxymethyl)pyrazine N-oxide | mp 139–140 |
| 112 | H | Me | cyclopentyl | Me | Me | 5-(methoxymethyl)-1,3-dimethylpyrazole | mp 112–123 |
| 113 | H | Me | cyclopentyl | Me | Me | N-methyl-(pyridazin-3-yl)methylamine | mp 164–166 |
| 114 | H | Me | cyclopentyl | H | Me | 4-(methoxymethyl)pyridine N-oxide | mp 142–143 |
| 115 | H | Me | cyclopentyl | Me | Me | 4-(methoxymethyl)-1H-imidazole | amorphous solid |

TABLE 2-continued
| Compound No | X | R1 | R2 | R3 | R4 | R5 | Physicochemical property |
|---|---|---|---|---|---|---|---|
| 116 | H | Me | 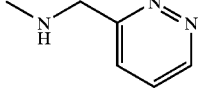 | H | MeNH |  | mp 149–152 |
| 117 | H | Me | 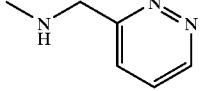 | H | Me |  | mp 161–163 |
| 118 | H | Me | 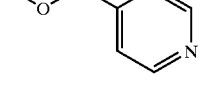 | H | EtNH |  | mp 129–130 |
| 119 | H | Me | 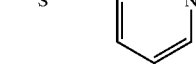 | Me | Me |  | mp 116–117 |
| 120 | H | Me | 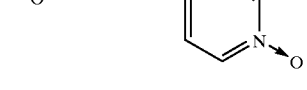 | Me | Me |  | mp 135–138 |
| 121 | H | Me | 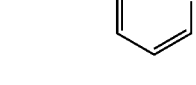 | Me | Me |  | mp 94–95 |
| 122 | H | Me | 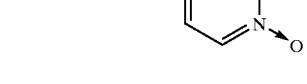 | H | EtNH |  | mp 85–88 |
| 123 | H | Me | 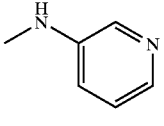 | H |  | H | mp 181–183 |
| 124 | H | Me | 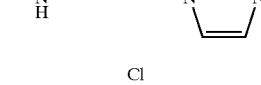 | H | H |  | mp 60–61 |
| 125 | H | Me | 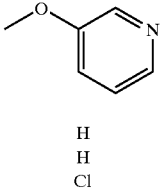 | Cl |  | Cl | mp 146–149 |
| 126 | MeO | Me | Me | H | H | H | mp 119–120 |
| 127 | Br | Me | Me | H | H | H | mp 161–163 |
| 128 | Br | Me | Me | H | Cl | H | mp 172–173 |

TABLE 2-continued
| Compound No | X | R1 | R2 | R3 | R4 | R5 | Physicochemical property |
|---|---|---|---|---|---|---|---|
| 129 | Br | Me |  | H | H | H | mp 122–124 |
| 130 | NO$_2$ | Me | Me | H | H | H | mp 184–186 |
| 131 | H | Me |  | Me | Me | Cl | mp 120–122 |
| 132 | H | Me |  | Me | Me | MeO | oil |
| 133 | H | Me |  | H | Cl | Cl | mp 133–134 |
| 134 | H | Me |  | H | NHEt | Cl | mp 129–131 |
| 135 | H | Me |  | H | Me | Cl | mp 131–132 |
| 136 | H | Me | 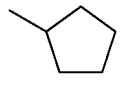 | H | NHMe | Cl | mp 155–156 |
TABLE 3
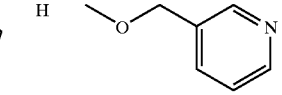
| Compound No | X | R1 | R2 | R3 | R4 | R5 | Physicochemical property |
|---|---|---|---|---|---|---|---|
| 137 | H | Me |  | H |  | H | mp 143–145 |

TABLE 3-continued

| Compound No | X | R1 | R2 | R3 | R4 | R5 | Physicochemical property |
|---|---|---|---|---|---|---|---|
| 138 | H | Me | cyclopentyl | H | -NH-CH2-(3-pyridyl) | H | mp 149–150 |
| 139 | H | Me | cyclopentyl | H | -O-(3-methoxypyridyl) | H | mp 134–135 |
| 140 | Br | Me | Me | H | -O-(3-methoxypyridyl) | H | mp 172–176 |
| 141 | H | Me | Me | H | -OCH2-(3-pyridyl) | H | mp 137–138 |
| 142 | H | Me | i-Pr | H | -OCH2-(3-pyridyl) | H | mp 138–142 |
| 143 | Br | Me | Me | H | Cl | H | mp 171–174 |
| 144 | NO2 | Me | Me | H | H | H | mp 162–164 |
| 145 | Br | Me | Me | H | -OCH2-(3-pyridyl) | H | mp 159–161 |
| 146 | Br | Me | cyclopentyl | H | H | H | mp 167–169 |
| 147 | H | Me | cyclopentyl | Me | H | -OCH2-(4-pyridyl) | mp 185–187 |
| 148 | Br | Me | Me | H | H | H | amorphous solid |

NMR data are shown below for the following compounds (compound numbers are those shown in Tables 2 and 3).

No. 1
$^1$H-NMR (CDCl$_3$) δ ppm: 1.51–1.69 (m, 2H), 1.71–1.98 (m, 6H), 3.84 (s, 3H), 4.65–4.75 (m, 1H), 5.37 (s, 2H), 6.79–6.94 (m, 3H), 7.42 (dd, 1H), 7.64–7.72 (m, 1H), 8.02 (s, 1H), 8.53–8.58 (m, 1H), 8.54 (s, 1H), 8.65 (d, 1H).

No. 2
$^1$H-NMR (CDCl$_3$) δ ppm: 1.50–1.69 (m, 2H), 1.70–1.95 (m, 6H), 3.82 (s, 3H), 4.65–4.73 (m, 1H), 5.32 (s, 2H), 5.70 (s, 2H), 6.78–6.88 (m, 3H), 7.30 (dd, 1H), 7.88 (s, 1H), 7.87–7.94 (m, 1H), 8.55–8.60 (m, 1H), 8.58 (s, 1H), 8.80 (d, 1H).

No. 7
$^1$H-NMR (CDCl$_3$) δ ppm: 3.83 (s, 3H), 3.87 (s, 3H), 5.35 (s, 2H), 5.70 (s, 2H), 6.80–6.90 (m, 3H), 7.30 (dd, 1H), 7.89 (s, 1H), 7.87–7.94 (m, 1H), 8.55–8.60 (m, 1H), 8.59 (s, 1H), 8.80 (d, 1H).

No. 8
$^1$H-NMR (CDCl$_3$) δ ppm: 1.32 (d, 6H), 3.83 (s, 3H), 4.47 (m, 1H), 5.32 (s, 2H), 5.70 (s, 2H), 6.80–6.90 (m, 3H), 7.30 (dd, 1H) 7.89 (s, 1H), 7.87–7.94 (m, 1H), 8.55–8.60 (m, 1H), 8.58 (s, 1H), 8.80 (d, 1H).

No. 10
$^1$H-NMR (CDCl$_3$) δ ppm: 1.5–1.7 (m, 2H), 1.70–1.95 (m, 6H), 3.50 (br, 3H), 3.82 (s, 3H), 4.65–4.75 (m, 1H), 5.28 (s, 2H), 5.40 (br, 2H), 6.75–6.95 (m, 3H), 7.20–7.30 (m, 1H), 7.60–7.70 (m, 1H), 7.70 (s, 1H), 8.43 (s, 1H), 8.51 (m, 1H), 8.59 (s, 1H).
No. 14
$^1$H-NMR (CDCl$_3$) δ ppm: 1.59 (m, 2H), 1.81–1.93 (m, 6H), 3.02 (t, 2H), 3.83 (s, 3H), 3.97 (m, 2H), 4.68–4.71 (m, 1H), 5.27 (s, 2H), 5.84 (m, 1H), 6.80–6.90 (m, 3H), 7.20 (d, 2H), 7.68 (s, 1H), 8.45 (s, 1H), 8.52 (d, 2H).
No. 15
$^1$H-NMR (CDCl$_3$) δ ppm: 1.50–1.70 (m, 2H), 1.70–1.95 (m, 6H), 3.83 (s, 3H), 4.65–4.73 (m, H), 5.34 (s, 2H), 5.84 (s, 2H), 6.80–6.95 (m, 3H), 7.91 (s, 1H), 8.50–8.60 (m, 3H), 8.85 (s, 1H).
No. 20
$^1$H-NMR (CDCl$_3$) δ ppm: 1.58–1.60 (m, 2H), 1.80–1.87 (m, 6H), 3.83 (s, 3H), 4.65–4.75 (m, 1H), 5.22 (s, 2H), 6.83–6.84 (m, 3H), 7.39 (dd, 1H), 7.60 (ddd, 1H), 7.94 (s, 1H), 8.52 (dd, 1H), 8.62 (d, 1H), 8.89 (s, 1H).
No. 28
$^1$H-NMR (DMSO-d$_6$) δ ppm: 1.51–1.77 (m, 8H), 3.70 (s, 3H), 4.44 (s, 2H), 4.68 (m, 1H), 6.50 (d, 1H), 6.86–6.93 (m, 4H), 7.84 (s, 1H), 8.33 (s, 2H).
No. 36
$^1$H-NMR (CDCl$_3$) δ ppm: 1.53–1.61 (m, 2H), 1.70–1.81 (m, 6H), 2.52 (s, 3H), 3.81 (s, 3H), 4.61–4.65 (m, 1H), 5.27 (s, 2H), 5.52 (s, 2H), 6.66–6.84 (m, 3H), 7.27–7.32 (m, 1H), 7.84–7.88 (m, 1H), 8.53–8.60 (m, 1H), 8.74–8.77 (m, 2H).
No. 37
$^1$H-NMR (CDCl$_3$) δ ppm: 1.53–1.59 (m, 2H), 1.75–1.90 (m, 6H), 2.46 (s, 3H), 3.81 (s, 3H), 4.59–4.63 (m, 1H), 4.68 (d, 2H, J=6.0 Hz) 5.15 (m, 2H), 6.15–6.25 (m, 1H), 6.62–6.78 (m, 3H), 7.19 (dd, 1H, J=4.6, 7.8 Hz), 7.70 (ddd, 1H, J=1.9, 1.9, 7.8 Hz), 8.45 (dd, 1H, J=1.9, 4.6 Hz), 8.53 (s, 1H), 8.63(d, 1H, J=1.9 Hz).
No. 44
$^1$H-NMR (CDCl$_3$) δ ppm: 1.56–1.59 (m, 2H), 1.80–1.84 (m, 6H), 2.30–2.35 (m, 2H), 3.04 (t, 2H), 3.82 (s, 3H), 4.52 (t, 2H), 4.68–4.70 (m, 1H), 5.26 (s, 2H), 6.81–6.88 (m, 3H), 7.10–7.13 (m, 1H), 7.20 (d, 1H), 7.58 (m, 1H), 7.86 (s, 1H), 8.54 (dd, 1H), 8.86 (s, 1H).
No. 45
$^1$H-NMR (CDCl$_3$) δ ppm: 1.54–1.56 (m, 2H), 1.80–1.81 (m, 6H), 3.15 (t, 2H), 3.17 (s, 3H), 3.81 (s, 3H), 4.08 (t, 2H), 4.68 (m, 1H), 5.17 (s, 2H), 6.79–6.89 (m, 3H), 7.10–7.16 (m, 2H), 7.55 (m, H), 7.67 (s, 1H), 8.55 (m, 1H), 8.73 (s, 1H).
No. 46
$^1$H-NMR (CDCl$_3$) δ ppm: 1.48–1.65 (m, 2H), 6.93 (dd, 1H), 8.99 (s, 1H), 1.68–1.98 (m, 6H), 7.00 (d, 1H), 3.83 (s, 3H), 4.70–4.80 (m, 1H), 5.34 (s, 2H), 6.84 (d, 1H), 7.48–7.64 (m, 3H), 7.94 (s, 1H), 7.94–8.01 (m, 2H), 8.79 (brs, 1H).
No. 52
$^1$H-NMR (CDCl$_3$) δ ppm: 1.55–1.58 (m, 2H), 1.76–1.83 (m, 6H), 3.36 (t, 2H), 3.82 (s, 3H), 4.68–4.70 (m, 1H), 4.85 (t, 2H), 5.25 (s, 2H), 6.80–6.87 (m, 3H), 7.12–7.16 (m, 1H), 7.31 (d, 1H), 7.62 (ddd, 1H), 7.84 (s, 1H), 8.56 (d, 1H), 8.86 (s, 1H).
No. 53
$^1$H-NMR (CDCl$_3$) δ ppm: 1.56 (m, 2H), 1.81 (m, 6H), 2.95 (t, 2H), 3.18 (s, 3H), 3.81 (s, 3H), 3.94 (t, 2H), 4.68 (m, 1H), 5.18 (s, 2H), 6.80–6.87 (m, 3H), 7.16 (d, 2H), 7.67 (s, 1H), 8.49 (s, 1H), 8.74 (s, 1H).
No. 60
$^1$H-NMR (CDCl$_3$) δ ppm: 1.47–1.67 (m, 2H), 1.71–2.01 (m, 6H), 3.80 (s, 3H), 4.09 (s, 3H), 4.17 (s, 3H), 4.63–4.75 (m, 1H), 5.03 (s, 2H), 5.47 (s, 2H), 6.70 (d, 1H), 6.75 (dd, 1H), 6.93 (d, 1H), 7.38 (d, 2H), 8.59 (d, 2H).
No. 62
$^1$H-NMR (CDCl$_3$) δ ppm: 2.00–2.15 (m, 2H), 2.46 (s, 3H), 2.96 (t, 2H), 3.70–4.03 (m, 6H), 3.82 (s, 3H), 4.78–4.85 (m, 1H), 5.19 (s, 2H), 5.20 (brs, 1H), 6.70–6.85 (m, 3H), 7.17 (d, 2H), 8.51 (d, 2H), 8.57 (s, 1H).
No. 74
$^1$H-NMR (CDCl$_3$) δ ppm: 1.56–1.58 (m, 2H), 1.76–1.84 (m, 6H), 2.17–2.22 (m, 2H), 2.85 (t, 2H), 3.82 (s, 3H), 4.16 (s, 3H), 4.45 (t, 2H), 4.67–4.68 (m, 1H), 5.20 (s, 2H), 6.81–6.82 (m, 3H), 7.16 (d, 2H), 7.68 (s, 1H), 8.50 (d, 2H).
No. 75
$^1$H-NMR (CDCl$_3$) δ ppm: 1.56 (m, 2H), 1.81 (m, 6H), 2.96 (t, 2H), 3.74 (q, 2H), 3.81 (s, 3H), 4.07 (s, 3H), 4.66–4.68 (m, 1H), 5.07 (t, 1H), 5.15 (s, 2H), 6.81 (m, 3H), 7.16 (d, 2H), 7.54 (s, 1H), 8.52 (d, 2H).
No. 76
$^1$H-NMR (CDCl$_3$) δ ppm: 1.59 (m, 2H), 1.80–1.83 (m, 6H), 2.79 (s, 3H), 3.83 (s, 3H), 4.70 (m, 1H), 5.22 (s, 2H), 5.88 (s, 2H), 6.82 (m, 3H), 7.48 (dd, 1H), 7.79 (d, 2H), 7.83 (s, 1H), 9.15 (d, 1H).
No. 99
$^1$H-NMR (CDCl$_3$) δ ppm: 1.50–1.85 (m, 8H), 2.46–2.52 (m, 3H), 2.63–2.75 (m, 3H), 2.88–2.97 (m, 2H), 3.54–3.58 (m, 2H), 3.81 (s, 3H), 4.54–4.58 (m, 1H), 4.63 (brs, 1H), 5.16–5.24 (m, 2H), 6.67–6.79 (m, 3H), 7.14–7.18 (m, 2H), 8.49–8.52 (m, 2H).
No. 101
$^1$H-NMR (CDCl$_3$) δ ppm: 1.50–1.60 (m, 2H), 1.75–1.90 (m, 6H), 2.54 (s, 3H), 2.76 (s, 3H), 3.81 (s, 3H), 4.60–4.70 (m, 1H), 5.23 (s, 2H), 5.86 (s, 2H), 6.64–6.78 (m, 3H), 7.48 (dd, 1H, J=4.9, 8.5 Hz), 7.79 (dd, 1H, J=1.5, 8.5 Hz), 9.14 (dd, 1H, J=1.5, 4.9 Hz).
No. 103
$^1$H-NMR (CDCl$_3$) δ ppm: 1.50–1.64 (m, 2H), 5.81 (s, 2H), 1.70–1.94 (m, 6H), 6.70–6.90 (m, 3H), 3.40 (brs, 6H), 3.82 (s, 3H), 4.64–4.72 (m, 1H), 5.15 (s, 2H), 7.44 (dd, 1H), 7.53 (s, 1H), 7.72 (dd, 1H), 9.11 (dd, 1H).
No. 109
$^1$H-NMR (CDCl$_3$) δ ppm: 1.50–1.60 (m, 2H), 1.70–1.90 (m, 6H), 2.52 (s, 3H), 2.76 (s, 3H), 3.81 (s, 3H), 4.60–4.70 (m, 1H), 5.22 (s, 2H), 5.66 (s, 2H), 6.63–6.83 (m, 3H), 8.52–8.55 (m, 2H), 8.86 (s, 1H).
No. 115
$^1$H-NMR (CDCl$_3$) δ ppm: 1.50–1.60 (m, 2H), 1.60–1.90 (m, 6H), 2.59 (s, 3H), 2.82 (s, 3H), 3.81 (s, 3H), 4.60–4.65 (m, 2H), 4.69 (s, 1H), 5.31 (s, 2H), 6.72–6.82 (m, 3H), 7.94 (d, 1H, J=1.2 Hz), 8.65 (d, 1H, J=1.2 Hz).
No. 120
$^1$H-NMR (CDCl$_3$) δ ppm: 1.56–1.81 (m, 8H), 2.10–2.19 (m, 2H), 2.51 (s, 3H), 2.75 (s, 3H), 2.85–2.90 (m, 2H), 3.81 (s, 3H), 4.40–4.44 (m, 2H), 4.63–4.64 (m, 1H), 5.24 (s, 2H), 6.65–6.79 (m, 3H), 7.14 (d, 2H, J=6.7 Hz), 8.13 (d, 2H, J=6.7 Hz).
No. 132
$^1$H-NMR (CDCl$_3$) δ ppm: 1.50–1.90 (m, 8H), 2.52 (s, 3H), 2.74 (s, 3H), 3.81 (s, 3H), 4.05 (s, 3H), 4.62–4.64 (m, 1H), 5.25 (s, 3H), 6.70–6.79 (m, 3H).
No. 148
$^1$H-NMR (CDCl$_3$) δ ppm: 3.80 (s, 3H), 3.90 (s, 3H), 5.46 (s, 2H), 6.72 (s, 1H), 7.10 (s, 1H), 8.29 (s, 1H), 8.85 (s, 1H), 9.15 (s, 1H).

Example 9

Manufacture of Tablets

Well pulverized 9-[(3-cyclopentyloxy-4-methoxy)benzyl]-6,8-dimethyl-2-[3-(4-pyridyl)propyloxy]purine (Compound No. 100 in Table 2, 1000 g), lactose (5900 g), crystalline cellulose (2000 g), low substituted hydroxypropylcellulose (1000 g) and magnesium stearate (100 g) were well mixed, and made into plain tablets containing 10 mg of the compound per one tablet of 100 mg by the direct compression method. These plain tablet were subjected to sugar coatings or film coatings to prepare sugar-coated tablets and film-coated tablets.

Example 10

Manufacture of Capsules

Well-pulverized 9-[(3-cyclopentyloxy-4-methoxy)benzyl]-6-methylamino-2-[(3-pyridazinyl)methyloxy]purine (Compound No. 79 in Table 2, 1000 g), corn starch (3000 g), lactose (6900 g), crystalline cellulose (1000 g) and magnesium stearate (100 g) were mixed to prepare capsules containing 10 m of the compound per each 120 mg capsule.

Example 11

Production of Inhalant

Well-pulverized 9-[(3-cyclopentyloxy-4-methoxy)benzyl]-6-ethylamino-2-[(3-pyridazinyl)methyloxy]purine (Compound No. 96 in Table 2, 5 g), medium chain saturated fatty acid triglyceride (10 g) and sorbitan monooleate (0.2 g) were well mixed, and 15.2 mg of the mixture was weighed and placed in a 5-ml aluminum container for aerosol. 84.8 mg of Freon 12/114 (1:1 mixture) was charged at a low temperature into the container, and the container was equipped with a constant volume adapter of 10.0 μl per one spraying to obtain an inhalant for constant volume spraying containing 5 mg of the compound per one container of 5 ml.

Test Example

PDE IV inhibitory activity of the compounds of the present invention was examined. Rolipram used as control is a compound disclosed in Japanese Patent Unexamined Publication (Kokai) No. 50-157360/1975, of which structure is shown in the section of related art of the present specification. Adv. Second Messenger Phosphoprotein Res., 22, 1, (1988) and other articles disclose that this compound has specific inhibitory activity against PDE IV.

Test Example 1

Effect on Enzymatic Activity of Type IV Phosphodiesterase (PDE IV)

The crude enzyme was purified from a cytoplasmic fraction of human monocyte-like cell strain U937 by using a Q-Sepharose column according to the method of Nicholson et al. [Br. J. Pharmacol., 97, 889 (1989)]. The enzymatic activity was determined by performing a reaction using 0.4 mM $^3$H-cAMP as the substrate in 50 mM Tris buffer (pH 8.0) containing 0.1 mg/ml BSA, 1 ml of EDTA and 5 mM $MgCl_2$ at 30° C. for 15 minutes, and then separating the produced 3H-5'-AMP using a cation exchange column and measuring its radioactivity according to the method of Hidaka et al. [Biochem. Med., 10, 301 (1974)]. After a test compound was added, the reaction mixture was incubated at 30° C. for 15 minutes, and then added with the substrate. Inhibitory ratio at each concentration was obtained based on the reaction performed with no addition of a test compound which was taken as 100%, and a concentration for 50% inhibition ($IC_{50}$) was calculated by the plot analysis. The results are shown in Table 4.

TABLE 4

| Compound No # | PDE IV Inhibitory Activity: $IC^{50}$ (M) |
|---|---|
| 2 | $8.9 \times 10^{-9}$ |
| 32 | $1.2 \times 10^{-9}$ |
| 36 | $2.6 \times 10^{-9}$ |
| 37 | $1.0 \times 10^{-9}$ |
| 39 | $1.4 \times 10^{-9}$ |
| 41 | $4.7 \times 10^{-10}$ |
| 55 | $4.5 \times 10^{-9}$ |
| 56 | $1.3 \times 10^{-9}$ |
| 57 | $4.6 \times 10^{-9}$ |
| 66 | $1.4 \times 10^{-9}$ |
| 72 | $7.5 \times 10^{-10}$ |
| 77 | $8.3 \times 10^{-10}$ |
| 78 | $1.3 \times 10^{-9}$ |
| 79 | $4.7 \times 10^{-9}$ |
| 81 | $3.5 \times 10^{-10}$ |
| 82 | $8.2 \times 10^{-10}$ |
| 83 | $6.9 \times 10^{-10}$ |
| 84 | $1.9 \times 10^{-9}$ |
| 85 | $1.3 \times 10^{-10}$ |
| 88 | $2.0 \times 10^{-10}$ |
| 93 | $4.4 \times 10^{-10}$ |
| 95 | $1.7 \times 10^{-9}$ |
| 96 | $3.8 \times 10^{-9}$ |
| 98 | $1.0 \times 10^{-9}$ |
| 100 | $5.5 \times 10^{-10}$ |
| 101 | $6.1 \times 10^{-9}$ |
| 102 | $1.5 \times 10^{-8}$ |
| 104 | $1.1 \times 10^{-9}$ |
| 112 | $2.2 \times 10^{-10}$ |
| 113 | $2.4 \times 10^{-8}$ |
| 119 | $6.4 \times 10^{-10}$ |
| 120 | $2.0 \times 10^{-9}$ |
| 122 | $1.5 \times 10^{-8}$ |
| 131 | $6.7 \times 10^{-9}$ |
| 134 | $4.1 \times 10^{-8}$ |
| 136 | $7.4 \times 10^{-8}$ |
| 137 | $6.4 \times 10^{-8}$ |
| 139 | $5.4 \times 10^{-8}$ |
| Rolipram | $3.0 \times 10^{-7}$ |

INDUSTRIAL APPLICABILITY

The compounds of the present invention represented by the formula (I) have excellent PDE IV inhibitory activity, and are useful as active ingredients of medicaments for therapeutic and/or preventive treatment of asthma and the like. The compounds represented by the formulas (A) and (B) are useful as synthetic intermediates for preparation of the compounds represented by the aforementioned formula (I).

What is claimed is:

1. A purine derivative represented by the following formula (I), a salt thereof, or an N-oxide thereof, or a hydrate thereof or a solvate thereof:

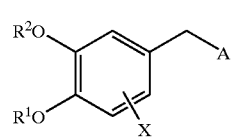

(I)

wherein $R^1$ represents a $C_1$–$C_4$ alkyl group or difluoromethyl group; $R^2$ represents tetrahydrofuranyl group, a $C_1$–$C_7$ alkyl group, a $C_1$–$C_7$ haloalkyl group, a $C_2$–$C_7$ alkenyl group, bicyclo[2,2,1]hept-2-yl group, or a $C_3$–$C_8$ cycloalkyl group; X represents hydrogen atom, a halogen atom, or nitro group; and A represents a group represented by the following formula:

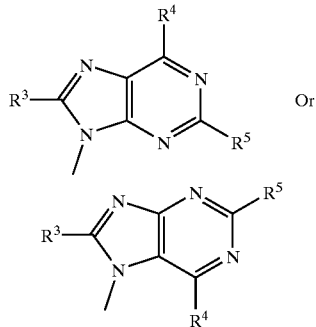

wherein $R^3$ represents hydrogen atom, a halogen atom, hydroxyl group, a $C_1$–$C_4$ alkyl group, a $C_1$–$C_4$ alkoxyl group, amino group, a $C_1$–$C_4$ alkylamino group, or a $C_2$–$C_8$ dialkylamino group; $R^4$ and $R^5$ each independently represent hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, a $C_2$–$C_8$ dialkylamino group, or a group represented by —Y—$(CH_2)_n$—B {Y represents —O—, —S—, —NHCO—, or —N($R^6$)— ($R^6$ represents hydrogen atom or a $C_1$–$C_4$ alkyl group), n represents an integer of from 0 to 4, and B represents a phenyl group, a naphthyl group, or a heterocyclic residue, each of which may be substituted}, provided that either $R^4$ or $R^5$ represents —Y—$(CH_2)_n$—B {Y represents —O—, —S—, —NHCO—, or —N($R^6$)— ($R^6$ represents hydrogen atom or a $C_1$–$C_4$ alkyl group)} when X represents hydrogen atom, and
(i) n represents an integer of from 0 to 4, and B represents a phenyl group, a naphthyl group, or a heterocyclic residue, each of which may be substituted when Y represents —O—, —S—, or —NHCO—, or
(ii) n represents an integer of from 1 to 4, and B represents a heterocyclic residue when Y represents —N($R^6$)—.

2. The purine derivative, a salt thereof, or an N-oxide thereof, or a hydrate thereof or a solvate thereof according to claim 1, wherein A is a group represented by the following formula:

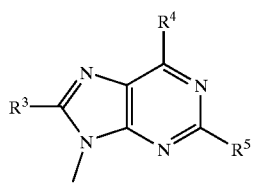

wherein $R^3$ is hydrogen atom, a halogen atom, hydroxyl group, a $C_1$–$C_4$ alkyl group, a $C_1$–$C_4$ alkoxyl group, amino group, a $C_1$–$C_4$ alkylamino group, or a $C_2$–$C_8$ dialkylamino group; one of $R^4$ and $R^5$ is hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, or a $C_2$–$C_8$ dialkylamino group, and the other is —Y—$(CH_2)_n$—B (Y is —O—, —S—, —NHCO—, or —N($R^6$)— ($R^6$ represents hydrogen atom or a $C_1$–$C_4$ alkyl group), n is an integer of from 0 to 4, and B represents a phenyl group, a naphthyl group or a heterocyclic residue, each of which may be substituted).

3. The purine derivative, a salt thereof, or an N-oxide thereof, or a hydrate thereof or a solvate thereof according to claim 1, wherein $R^1$ is a $C_1$–$C_4$ alkyl group; $R^2$ is tetrahydrofuranyl group, a $C_1$–$C_6$ alkyl group, a $C_1$–$C_3$ haloalkyl group, or a $C_3$–$C_8$ cycloalkyl group, and A is a group represented by the following formula:

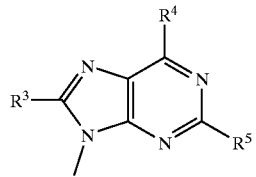

wherein $R^3$ is hydrogen atom, a halogen atom, hydroxyl group, a $C_1$–$C_4$ alkyl group or a $C_1$–$C_4$ alkoxyl group; $R^4$ is hydrogen atom, a halogen atom, a $C_1$–$C_4$ alkyl group, a $C_1$–$C_4$ alkoxyl group, a $C_1$–$C_4$ alkylamino group, or a $C_2$–$C_8$ dialkylamino group, $R^5$ is —Y—$(CH_2)_n$—B (Y is —O—, —S—, or —NHCO—, n is an integer of from 1 to 4, and B represents a heterocyclic residue which may be substituted).

4. The purine derivative, a salt thereof, or an N-oxide thereof, or a hydrate thereof or a solvate thereof according to claim 1, wherein $R^1$ is a $C_1$–$C_3$ alkyl group; $R^2$ is a $C_3$–$C_8$ cycloalkyl group, and A is a group represented by the following formula:

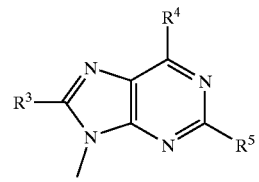

wherein $R^3$ is hydrogen atom, a $C_1$–$C_3$ alkyl group or a $C_1$–$C_3$ alkoxyl group; $R^4$ is a $C_1$–$C_3$ alkyl group, a $C_1$–$C_3$ alkoxyl group or a $C_1$–$C_3$ alkylamino group; $R^5$ is —Y—$(CH_2)_n$—B (Y is —O—, n is an integer of from 1 to 4, and B is a heterocyclic residue which may be substituted).

5. 2-Chloro-9-[(3-cyclopentyloxy-4-methoxy)benzyl]-6,8-dimethylpurine or a salt thereof, or a hydrate thereof or a solvate thereof.

6. 9-[(3-Cyclopentyloxy-4-methoxy)benzyl]-6,8-dimethyl-2-methoxypurine or a salt thereof, or a hydrate thereof or a solvate thereof.

7. 9-[(3-Cyclopentyloxy-4-methoxy)benzyl]-6,8-dimethyl-2-(pyridazinylmethyloxy)purine or a salt thereof, or a hydrate thereof or a solvate thereof.

8. 9-[(3-Cyclopentyloxy-4-methoxy)benzyl]-6,8-dimethyl-2-[4-pyridylmethyl-oxy]purine or a salt thereof, or a hydrate thereof or a solvate thereof.

9. 4-[[9-[(3-Cyclopentyloxy-4-methoxy)benzyl]-6,8-dimethylpurin]-2-yl-oxy-methyl]pyridine N-oxide or a salt thereof, or a hydrate thereof or a solvate thereof.

10. 9-[(3-Cyclopentyloxy-4-methoxy)benzyl]-6,8-dimethyl-2-[2-(4-pyridyl)-ethyloxy]purine or a salt thereof, or a hydrate thereof or a solvate thereof.

11. 4-[[9-[(3-Cyclopentyloxy-4-methoxy)benzyl]-6,8-dimethylpurin]-2-yl-2-oxy-ethyl]pyridine N-oxide or a salt thereof, or a hydrate thereof or a solvate thereof.

12. 9-[(3-Cyclopentyloxy-4-methoxy)benzyl]-6-methylamino-2-(3-pyridazinyl-methyloxy)purine or a salt thereof, or a hydrate or a solvate thereof.

13. 9-[(3-Cyclopentyloxy-4-methoxy)benzyl]-6,8-dimethyl-2-[2-(4-pyridyl)-ethylamino]purine or a salt thereof, or a hydrate thereof or a solvate thereof.

14. 9-[(3-Cyclopentyloxy-4-methoxy)benzyl]-6,8-dimethyl-2-[(4-pyridyl)-methylamino]purine or a salt thereof, or a hydrate thereof or a solvate thereof.

15. 9-[(3-Cyclopentyloxy-4-methoxy)benzyl]-6,8-dimethyl-2-[3-(4-pyridyl)-propyloxy]purine or a salt thereof, or a hydrate thereof or a solvate thereof.

16. 4-[[9-[(3-Cyclopentyloxy-4-methoxy)benzyl]-6,8-dimethylpurin]-2-yl-3-oxy-propyl]pyridine N-oxide or a salt thereof, or a hydrate thereof or a solvate thereof.

17. A medicament which comprises a substance selected from the group consisting of the purine derivative, a salt thereof, and an N-oxide compound thereof, and a hydrate thereof and a solvate thereof according to claim 1 as an active ingredient and at least one pharmaceutically acceptable additive.

18. A method of treating asthma comprising administering a therapeutically effective amount of a medicament according to claim 17 to a subject in need thereof.

19. A compound represented by the following formula (A):

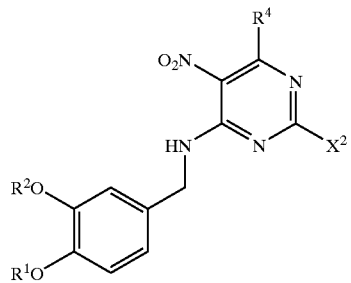

(A)

wherein $R^1$ represents a $C_1$–$C_4$ alkyl group or difluoromethyl group; $R^2$ represents tetrahydrofuranyl group, a $C_1$–$C_7$ alkyl group, a $C_1$–$C_7$ haloalkyl group, a $C_2$–$C_7$ alkenyl group, bicyclo[2,2,1]hept-2-yl group, or a $C_3$–$C_8$ cycloalkyl group; $R^4$ represents hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, a $C_2$–$C_8$ dialkylamino group, or —Y—$(CH_2)_n$—B {Y represents —O—, —S—, —NHCO—, or —N($R^6$)— ($R^6$ represents hydrogen atom or a $C_1$–$C_4$ alkyl group), n represents an integer of from 0 to 4, B represents a phenyl group, a naphthyl group, or a heterocyclic residue, each of which may be substituted, and $X^2$ represents a halogen atom}.

20. The compound according to claim 19, wherein $R^1$ is a $C_1$–$C_4$ alkyl group, $R^2$ is tetrahydrofuranyl group, a $C_1$–$C_6$ alkyl group, a $C_1$–$C_3$ haloalkyl group, or a $C_3$–$C_8$ cycloalkyl group, $R^4$ is hydrogen atom, a halogen atom, a $C_1$–$C_4$ alkyl group, a $C_1$–$C_4$ alkoxyl group, a $C_1$–$C_4$ alkylamino group, or a $C_2$–$C_8$ dialkylamino group.

21. A compound represented by the following formula (B):

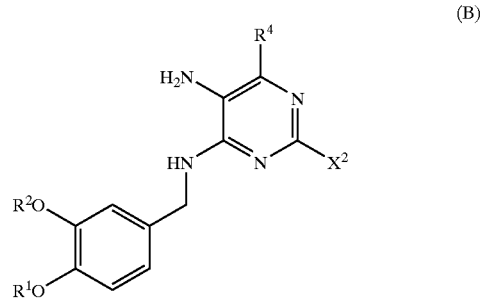

(B)

wherein $R^1$ represents a $C_1$–$C_4$ alkyl group or difluoromethyl group; $R^2$ represents tetrahydrofuranyl group, a $C_1$–$C_7$ alkyl group, a $C_1$–$C_7$ haloalkyl group, a $C_2$–$C_7$ alkenyl group, bicyclo[2,2,1]hept-2-yl group, or a $C_3$–$C_8$ cycloalkyl group; $R^4$ represents hydrogen atom, a halogen atom, a $C_1$–$C_4$ alkyl group, a $C_1$–$C_4$ alkoxyl group, amino group, a $C_1$–$C_4$ alkylamino group, pyrrolidinyl group, morpholino group, a $C_2$–$C_8$ dialkylamino group, or —Y—$(CH_2)_n$—B {Y represents —O—, —S—, —NHCO—, or —N($R^6$)— ($R^6$ represents hydrogen atom or a $C_1$–$C_4$ alkyl group), n represents an integer of from 0 to 4, B represents a phenyl group, a naphthyl group, or a heterocyclic residue, each of which may be substituted, and $X^2$ represents a halogen atom}.

22. The compound according to claim 21, wherein $R^1$ is a $C_1$–$C_4$ alkyl group, $R^2$ is tetrahydrofuranyl group, a $C_1$–$C_6$ alkyl group, a $C_1$–$C_3$ haloalkyl group, or a $C_3$–$C_8$ cycloalkyl group, $R^4$ is hydrogen atom, a halogen atom, a $C_1$–$C_4$ alkyl group, a $C_1$–$C_4$ alkoxyl group, a $C_1$–$C_4$ alkylamino group, or a $C_2$–$C_8$ dialkylamino group.

23. A method of treating asthma comprising administering a therapeutically effective amount of a purine derivative according to claim 1 to a subject in need thereof.

24. A method of treating asthma comprising administering a therapeutically effective amount of a medicament according to claim 16 to a subject in need thereof.

* * * * *